(12) United States Patent
Buon et al.

(10) Patent No.: US 9,598,409 B2
(45) Date of Patent: Mar. 21, 2017

(54) IMIDAZOPYRIDINE COMPOUNDS AND USES THEREOF

(71) Applicant: NEOMED INSTITUTE, Montréal, Québec (CA)

(72) Inventors: Christophe Buon, Montréal (CA); Louis-David Cantin, Montréal (CA); Yun-Jin Hu, Montréal (CA); Xuehong Luo, Montréal (CA); Miroslaw Jerzy Tomaszewski, Montréal (CA)

(73) Assignee: Neomed Institute, Montreal, Quebec (CA)

(*) Notice: Subject to any disclaimer, the term of this patent is extended or adjusted under 35 U.S.C. 154(b) by 32 days.

(21) Appl. No.: 14/764,404

(22) PCT Filed: Jan. 31, 2014

(86) PCT No.: PCT/CA2014/050062
§ 371 (c)(1),
(2) Date: Jul. 29, 2015

(87) PCT Pub. No.: WO2014/117274
PCT Pub. Date: Aug. 7, 2014

(65) Prior Publication Data
US 2015/0361078 A1    Dec. 17, 2015

Related U.S. Application Data

(60) Provisional application No. 61/759,123, filed on Jan. 31, 2013.

(51) Int. Cl.
*C07D 471/04* (2006.01)

(52) U.S. Cl.
CPC ................. *C07D 471/04* (2013.01)

(58) Field of Classification Search
CPC .................................................. C07D 471/04
See application file for complete search history.

(56) References Cited

U.S. PATENT DOCUMENTS

| 7,550,495 B2 | 6/2009 | Page et al. |
| 8,530,467 B2 | 9/2013 | Cantin et al. |
| 2006/0264490 A1 | 11/2006 | Page et al. |

FOREIGN PATENT DOCUMENTS

| CA | 2655780 A1 | 12/2007 |
| CA | 2777746 A1 | 5/2011 |
| EP | 0533266 A1 | 3/1993 |
| EP | 2501697 B1 | 10/2013 |
| WO | 9722596 A1 | 6/1997 |
| WO | 9730035 A1 | 8/1997 |
| WO | 9732856 A1 | 9/1997 |
| WO | 9813354 A1 | 4/1998 |
| WO | 9902166 A1 | 1/1999 |
| WO | 0040529 A1 | 7/2000 |
| WO | 0041669 A2 | 7/2000 |
| WO | 0047212 A1 | 8/2000 |
| WO | 0192224 A1 | 12/2001 |
| WO | 0204434 A1 | 1/2002 |
| WO | 0208213 A1 | 1/2002 |
| WO | 2007147478 A1 | 12/2007 |
| WO | 2008136756 A1 | 11/2008 |
| WO | 2011062550 A1 | 5/2011 |

OTHER PUBLICATIONS

Chen et al. "A P2X purinoceptor expressed by a subset of sensory neurons", Nature, 1995, pp. 428-431, vol. 377:6548.
Lewis et al. "Coexpression of P2X2 and P2X3 receptor subunits can account for ATP-gated currents in sensory neurons", Nature, 1995, pp. 432-435, vol. 377:6548.
Garcia-Guzman et al. "Molecular characterization and pharmacological properties of the human P2X3 purinoceptor", Mol. Brain Res., 1997, pp. 59-66, vol. 47:1-2.
Cockayne et al. "Urinary bladder hyporeflexia and reduced pain-related behaviour in P2X 3-deficient mice", Nature, 2000, pp. 1011-1015, vol. 407: 6807.
Zhong et al. "Bladder and cutaneous sensory neurons of the rat express different functional P2X receptors", Neuroscience, 2003, pp. 667-675, vol. 120:3.
Cantin et al. "Discovery of P2X3 Selective Antagonists for the Treatment of Chronic Pain", Bioorganic & Medicinal Chemistry Letters, 2012, pp. 2565-2571, vol. 22:7.

*Primary Examiner* — Rebecca Anderson
(74) *Attorney, Agent, or Firm* — Edward J. Baba; Bozicevic, Field & Francis LLP

(57) ABSTRACT

This invention generally relates to substituted imidazopyridine compounds, particularly substituted 4-(imidazo[1,2-a]pyridin-2-yl)benzamide compounds and salts thereof. This invention also relates to pharmaceutical compositions and kits comprising such a compound, uses of such a compound (including, for example, treatment methods and medicament preparations), processes for making such a compound, and intermediates used in such processes.

17 Claims, 1 Drawing Sheet

IMIDAZOPYRIDINE COMPOUNDS AND USES THEREOF

FIELD OF THE INVENTION

This invention generally relates to substituted imidazopyridine compounds, particularly substituted 4-(imidazo[1,2-a]pyridin-2-yl)benzamide compounds and salts thereof. This invention also relates to pharmaceutical compositions and kits comprising such a compound, uses of such a compound (including, for example, treatment methods and medicament preparations), processes for making such a compound, and intermediates used in such processes.

BACKGROUND

P2X purinoreceptors are a family of ion channels that are activated by extracellular adenosine triphosphate (ATP). Purinoreceptors have been implicated in a variety of biological functions, especially those related to pain sensitivity. The P2X3 receptor subunit is a member of this family. It was originally cloned from rat dorsal root ganglia. Chen et al., *Nature*, vol. 377, pp. 428-431 (1995). The nucleotide and amino acid sequences of both rat and human P2X3 are now known. Lewis, et al., *Nature*, vol. 377, pp. 432-435 (1995); and Garcia-Guzman, et al., *Brain Res. Mol. Brain Res.*, vol. 47, pp. 59-66 (1997).

P2X3 is reportedly involved in afferent pathways controlling urinary bladder volume reflexes. Consequently, inhibiting P2X3 may have therapeutic potential for treating disorders of urine storage and voiding, such as overactive bladder. Cockayne, et al., *Nature*, vol. 407, pp. 1011-1015 (2000).

P2X3 also is selectively expressed on nociceptive, small diameter sensory neurons (i.e., neurons that are stimulated by pain or injury), which is consistent with a role in pain sensitivity. And blocking P2X3 receptors has been reported to be analgesic in animal models of chronic inflammatory and neuropathic pain. Jarvis, et al., *PNAS*, 99, 17179-17184 (2002). It is, therefore, believed that a method for reducing the P2X3 level or activity would be useful for modulating pain sensation in a subject suffering from pain.

Various other disorders also have been discussed as being treatable using compounds having P2X3 activity. See, e.g., WO2008/136756.

P2X3 also is capable of forming P2X2/3 heterodimers with P2X2, which is another member of the P2X purinergic ligand-gated ion channel family. P2X2/3 is highly expressed on the terminals (central and peripheral) of sensory neurons. Chen, et al., Nature, vol. 377, pp. 428-431 (1995). Results from recent studies also suggest that P2X2/3 is predominantly expressed (over P2X3) in bladder sensory neurons, and are likely to play a role in sensing of urinary bladder filling and nociception. Zhong, et al., Neuroscience, vol. 120, pp. 667-675 (2003).

In view of the foregoing, there is a need for new P2X3 and/or P2X2/3 receptor ligands, particularly antagonists, that may be useful and safe for treating various disorders related to P2X3 and/or P2X2/3.

SUMMARY OF THE INVENTION

This invention comprises, inter alia, imidazopyridine compounds; treatment methods using the imidazopyridine compounds (e.g., use of the imidazopyridine to treat various disorders and as pharmacological tools); use of the imidazopyridine compounds to make medicaments; compositions comprising the imidazopyridine compounds (e.g., pharmaceutical compositions); methods for manufacturing the imidazopyridine compounds; and intermediates used in such manufacturing methods.

Briefly, this invention is directed, in part, to a compound of Formula I or a salt thereof. Formula I corresponds to:

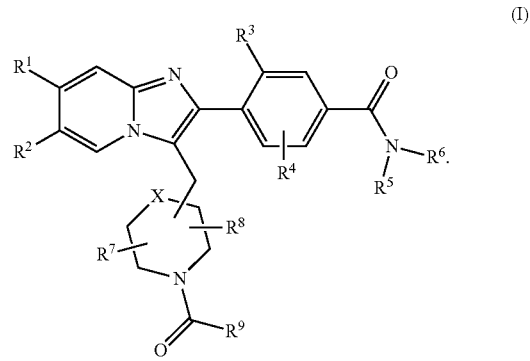

Here:

$R^1$ is selected from the group consisting of cyano, halogen, methyl, and ethyl.

$R^2$ is selected from the group consisting of hydrogen, halogen, methyl, and ethyl.

$R^3$ is selected from the group consisting of halogen, methyl, and ethyl.

$R^4$ is selected from the group consisting of hydrogen, halogen, methyl, ethyl, and methoxy.

$R^5$ and $R^6$ are independently selected from the group consisting of hydrogen, $C_1$-$C_6$-alkyl, and hydroxy-$C_1$-$C_6$-alkyl. Alternatively, $R^5$ and $R^6$, together with the nitrogen to which they are both attached, form a 5- or 6-member heterocycloalkyl. The heterocycloalkyl is optionally substituted with one or more substituents independently selected from the group consisting of halogen, hydroxyl, and $C_1$-$C_4$-alkyl.

$R^7$ and $R^8$ are independently selected from the group consisting of hydrogen and $C_1$-$C_4$-alkyl.

$R^9$ is selected from the group consisting of $C_1$-$C_6$-alkyl, $C_3$-$C_6$-cycloalkyl, $C_1$-$C_6$-alkyl-$C_3$-$C_6$-cycloalkyl, halo-$C_1$-$C_6$-alkyl, $C_1$-$C_6$-alkoxy, halo-$C_1$-$C_6$-alkoxy, and $C_1$-$C_6$-alkoxy-$C_1$-$C_6$-alkyl.

X is selected from a bond, $CH_2$, and O.

This invention also is directed, in part, to a pharmaceutical composition that comprises a compound of Formula I or pharmaceutically acceptable salt thereof. In general, the composition also comprises at least one pharmaceutically acceptable inert ingredient. Such inert ingredients are sometimes collectively identified in this patent as "carriers, diluents, or excipients." The composition may further comprise one or more additional active ingredients. For example, such a composition may comprise one or more additional compounds of Formula I and/or salts thereof. The composition also may, for example, alternatively or additionally comprise one or more active ingredients other than a compound of Formula I or salt thereof.

This invention also is directed, in part, to a compound of Formula I or a pharmaceutically acceptable salt thereof for use as a medicament.

This invention also is directed, in part, to a kit comprising a compound of Formula I or a pharmaceutically acceptable salt thereof.

This invention also is directed, in part, to the use of a compound of Formula I or a pharmaceutically acceptable salt thereof for manufacturing a pharmaceutical composition (or "medicament"). In general, the composition also comprises at least one pharmaceutically acceptable carrier, diluent, or excipient. Such a composition may further comprise one or more additional active ingredients. For example, such a composition may comprise one or more additional compounds of Formula I and/or pharmaceutically acceptable salts thereof. The composition also may, for example, alternatively or additionally comprise one or more active ingredients other than a compound of Formula I or salt thereof.

In some embodiments, the medicament is useful for treating a condition associated with P2X3 activity (particularly excessive activity) in an animal (e.g., a human).

In some embodiments, the medicament is useful for treating a condition associated with P2X2/3 activity (particularly excessive activity) in an animal (e.g., a human).

In some embodiments, the medicament is useful for treating pain in an animal (e.g., a human).

In some embodiments, the medicament is useful for treating a urinary tract disorder in an animal (e.g., a human).

This invention also is directed, in part, to methods for treating a disorder in an animal (e.g., a human) in need of such treatment. These methods comprise administering to the animal a compound of Formula I or pharmaceutically acceptable salt thereof. Such methods encompass the administration of a compound of Formula I or pharmaceutically acceptable salt thereof alone. They also encompass administering other ingredients as well. For example, a compound of Formula I or pharmaceutically acceptable salt thereof will typically be administered as part of a pharmaceutical composition that also comprises one or more carriers, diluents, or excipients. A compound of Formula I or pharmaceutically acceptable salt thereof also may be administered with one or more additional active ingredients. For example, one or more additional compounds of Formula I and/or pharmaceutically acceptable salts thereof may be administered. Alternatively or additionally, one or more active ingredients other than a compound of Formula I or pharmaceutically acceptable salt thereof may be administered.

In some embodiments, the disorder comprises a disorder associated with P2X3 activity (particularly excessive activity).

In some embodiments, the disorder comprises a disorder associated with P2X2/3 activity (particularly excessive activity).

In some embodiments the disorder comprises pain.

In some embodiments, the disorder comprises a urinary tract disorder.

In general, when a compound of Formula I or salt thereof is administered as the only active ingredient to treat a targeted disorder, the administered amount of a compound of Formula I or pharmaceutically acceptable salt thereof is therapeutically effective to treat the targeted disorder in the animal. When, in contrast, a compound of Formula I or pharmaceutically acceptable salt thereof is administered in combination with one or more other active ingredients, the amount of a compound of Formula I or salt thereof and the amount(s) of the other active ingredient(s) are, together, therapeutically effective to treat the targeted disorder in the mammal.

Further benefits of Applicants' invention will be apparent to one skilled in the art from reading this specification.

Figure 1:
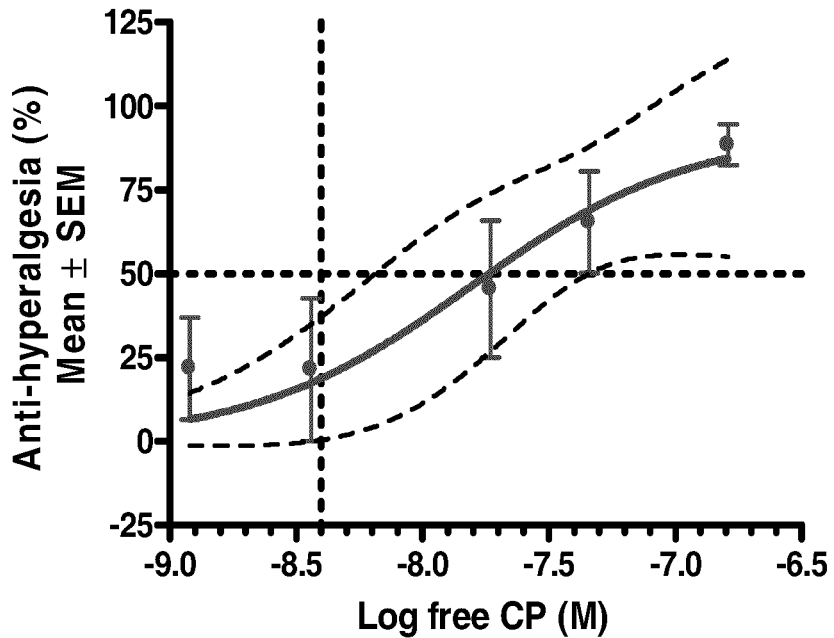
FIG. 1: Efficacy of Example 15 in rat FCA 96-hr model of inflammatory pain 30 minutes after p.o. dosing: Heat hyperalgesia (HH). Log free $C_P$=Logarithm of molar free drug concentration in plasma.

In the figures, the dotted curved line represents the 95% confidence interval of the best-fit curve. The dotted vertical line shows the in vitro IC50 of the compound at the rat P2X3 assessed in FLIPR. The dotted horizontal line shows the 50% reversal.

DESCRIPTION OF ILLUSTRATIVE EMBODIMENTS

This description of illustrative embodiments is intended only to acquaint others skilled in the art with Applicants' invention, its principles, and its practical application so that others skilled in the art may adapt and apply the invention in its numerous forms, as they may be best suited to the requirements of a particular use. This description and its specific examples, while indicating embodiments of this invention, are intended for purposes of illustration only. This invention, therefore, is not limited to the illustrative embodiments described in this specification, and may be variously modified.

As noted above, this invention is directed, in part, to a compound of Formula I or a salt thereof. Formula I corresponds to:

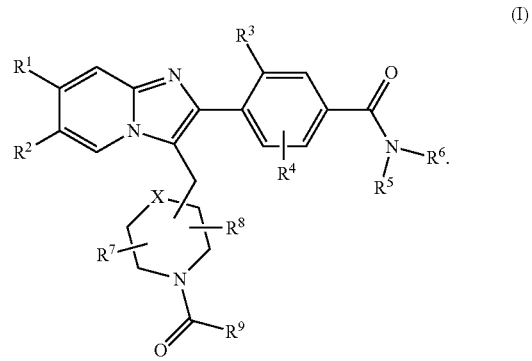

Here:

$R^1$ is selected from the group consisting of cyano, halogen, methyl, and ethyl.

In some embodiments, $R^1$ is chloro.
In some embodiments, $R^1$ is iodo.
In some embodiments, $R^1$ is fluoro.
In some embodiments, $R^1$ is bromo.
In some embodiments, $R^1$ is methyl.
In some embodiments, $R^1$ is ethyl.
In some embodiments, $R^1$ is cyano.

$R^2$ is selected from the group consisting of hydrogen, halogen, methyl, and ethyl.

In some embodiments, $R^2$ is hydrogen. In such embodiments, the compound corresponds in structure to Formula IA:

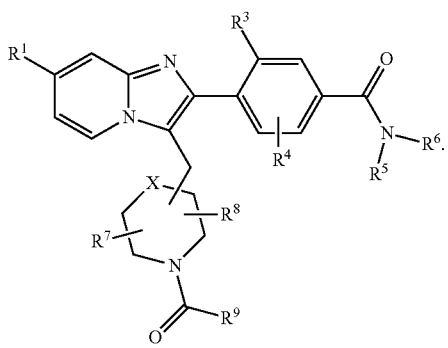

(IA)

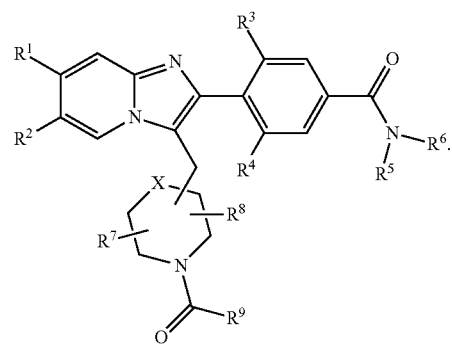

(IC)

In some embodiments, R¹ is chloro, and R² is hydrogen.
In some embodiments, R¹ is iodo, and R² is hydrogen.
In some embodiments, R¹ is fluoro, and R² is hydrogen.
In some embodiments, R¹ is methyl, and R² is hydrogen.
In some embodiments, R¹ is cyano, and R² is hydrogen.

R³ is selected from the group consisting of halogen, methyl, and ethyl.
In some embodiments, R³ is fluoro.
In some embodiments, R³ is chloro.
In some embodiments, R³ is iodo.
In some embodiments, R³ is bromo.
In some embodiments, R³ is methyl.
In some embodiments, R³ is ethyl.

R⁴ is selected from the group consisting of hydrogen, halogen, methyl, ethyl, and methoxy.

In some embodiments, R⁴ is hydrogen. In such embodiments, the compound corresponds in structure to Formula IB:

In other such embodiments, the compound corresponds in structure to Formula ID:

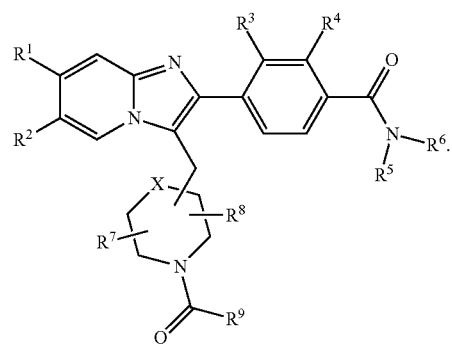

(ID)

And, in still other embodiments, the compound corresponds in structure to Formula IE:

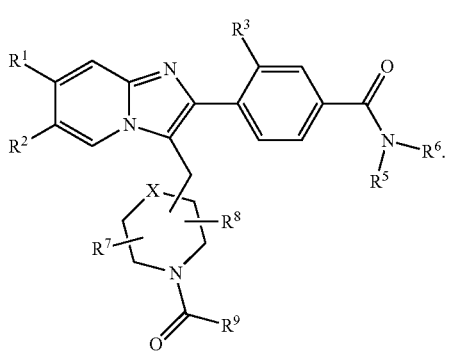

(IB)

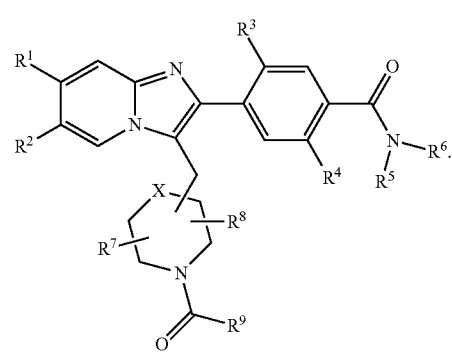

(IE)

In some embodiments, R⁴ is fluoro.
In some embodiments, R⁴ is chloro.
In some embodiments, R⁴ is iodo.
In some embodiments, R⁴ is bromo.
In some embodiments, R⁴ is methyl.
In some embodiments, R⁴ is ethyl.
In some embodiments, R⁴ is methoxy.

In some embodiments, R⁴ is selected from the group consisting of halogen, methyl, and ethyl. In some such embodiments, the compound corresponds in structure to Formula IC:

In some embodiments, R³ is fluoro, and R⁴ is hydrogen.
In some embodiments, R³ is chloro, and R⁴ is hydrogen.
In some embodiments, R³ is methyl, and R⁴ is hydrogen.
In some embodiments, R³ is fluoro, and R⁴ is fluoro.
In some embodiments, R³ is methyl, and R⁴ is fluoro.
In some embodiments, R³ is chloro, and R⁴ is chloro.
In some embodiments, R³ is methyl, and R⁴ is chloro.
In some embodiments, R³ is fluoro, and R⁴ is methyl.
In some embodiments, R³ is chloro, and R⁴ is methyl.
In some embodiments, R³ is methyl, and R⁴ is methyl.
In some embodiments, R⁵ and R⁶ are independently selected from the group consisting of hydrogen, $C_1$-$C_6$-alkyl, and hydroxy-$C_1$-$C_6$-alkyl.

In some embodiments, $R^5$ is hydrogen such that the compound corresponds in structure to Formula IF:

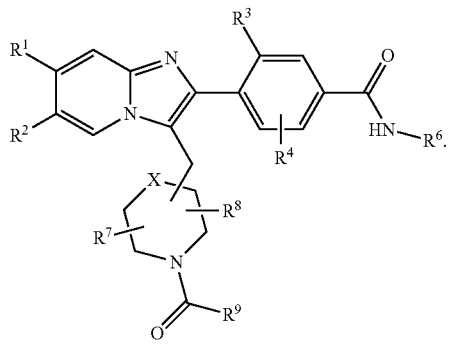

(IF)

In some embodiments, $R^5$ is $C_1$-$C_6$-alkyl.
In some embodiments, $R^5$ is methyl.
In some embodiments, $R^5$ is ethyl.
In some embodiments, $R^5$ is hydroxy-$C_1$-$C_6$-alkyl.
In some embodiments, $R^5$ is 2-hydroxyethyl. Such a substituent corresponds in structure to:

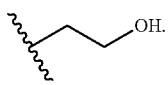 [SMILES: *CCO]

In some embodiments, $R^6$ is hydrogen.
In some embodiments, $R^6$ is $C_1$-$C_6$-alkyl.
In some embodiments, $R^6$ is methyl.
In some embodiments, $R^6$ is ethyl.
In some embodiments, $R^6$ is hydroxy-$C_1$-$C_6$-alkyl.
In some embodiments, each of $R^5$ and $R^6$ is hydrogen.
In some embodiments, each of $R^5$ and $R^6$ is methyl.
In some embodiments, each of $R^5$ and $R^6$ is ethyl.
In some embodiments, $R^5$ is hydrogen, and $R^6$ is methyl.
In some embodiments, $R^5$ is hydrogen, and $R^6$ is ethyl.
In some embodiments, $R^5$ is hydrogen, and $R^6$ is 2-hydroxyethyl. In such embodiments, the compound corresponds in structure to Formula IG:

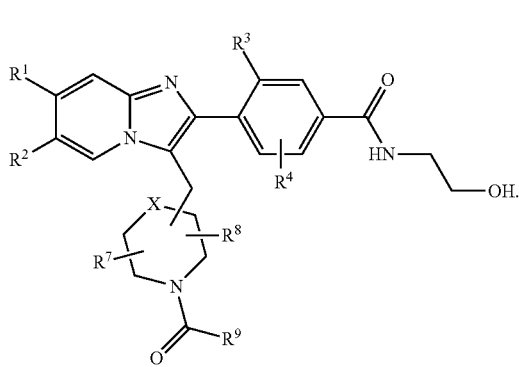

(IG)

In some embodiments, $R^5$ is methyl, and $R^6$ is ethyl.
In other embodiments, $R^5$ and $R^6$, together with the nitrogen to which they are both attached, form a 5- or 6-member heterocycloalkyl. The heterocycloalkyl is optionally substituted with one or more substituents independently selected from the group consisting of halogen, hydroxyl, and $C_1$-$C_4$-alkyl. This heterocycloalkyl comprises a saturated, single-ring structure with 5 or 6 ring atoms that include at least 3 carbon atoms; the nitrogen to which both $R^5$ and $R^6$ is attached; and, optionally, one additional heteroatom selected from the group consisting of nitrogen, sulfur, and oxygen. In some embodiments, the heterocycloalkyl is selected from the group consisting of pyrrolidinyl, piperidinyl, piperazinyl, morpholinyl, and thiomorpholinyl.

In some embodiments, $R^5$ and $R^6$, together with the nitrogen to which they are both attached, form an unsubstituted 5- or 6-member heterocycloalkyl.

In some embodiments, $R^5$ and $R^6$, together with the nitrogen to which they are both attached, form unsubstituted pyrrolidinyl.

In some embodiments, $R^5$ and $R^6$, together with the nitrogen to which they are both attached, form unsubstituted piperidinyl.

In some embodiments, $R^5$ and $R^6$, together with the nitrogen to which they are both attached, form unsubstituted morpholinyl.

In some embodiments, $R^5$ and $R^6$, together with the nitrogen to which they are both attached, form a 5- or 6-member heterocycloalkyl substituted with hydroxy.

In some embodiments, $R^5$ and $R^6$, together with the nitrogen to which they are both attached, form hydroxylpyrrolidinyl.

$R^7$ and $R^8$ are independently selected from the group consisting of hydrogen and $C_1$-$C_4$-alkyl.

In some embodiments, $R^7$ is hydrogen.
In some embodiments, $R^7$ is $C_1$-$C_4$-alkyl.
In some embodiments, $R^7$ is methyl.
In some embodiments, $R^8$ is hydrogen.
In some embodiments, $R^8$ is $C_1$-$C_4$-alkyl.
In some embodiments, $R^8$ is methyl.

In some embodiments, each of $R^7$ and $R^8$ is hydrogen. In such embodiments, the compound corresponds in structure to Formula IH:

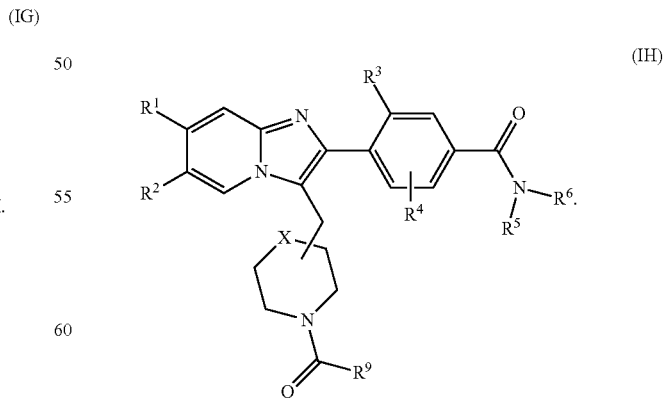

(IH)

In some embodiments, $R^7$ is $C_1$-$C_4$-alkyl, and $R^8$ is hydrogen. In some such embodiments, the compound corresponds in structure to Formula II:

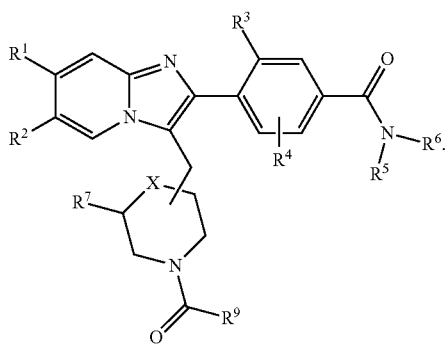

(II)

In other such embodiments, the compound corresponds in structure to Formula IJ:

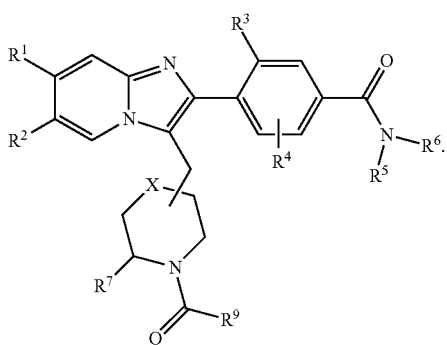

(IJ)

In some embodiments, $R^7$ is methyl, and $R^8$ is hydrogen.

In some embodiments, each of $R^7$ and $R^8$ is $C_1$-$C_4$-alkyl. In some such embodiments, $R^7$ and $R^8$ are bonded to the same carbon. For example, in some embodiments, the compound corresponds in structure to Formula IK:

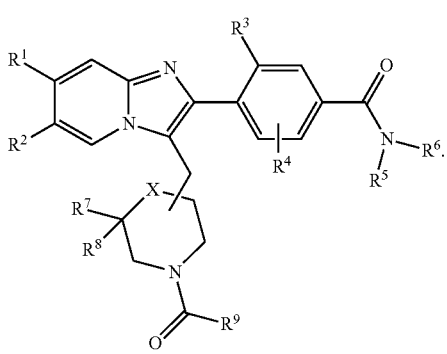

(IK)

In other embodiments, the compound corresponds in structure to Formula IL:

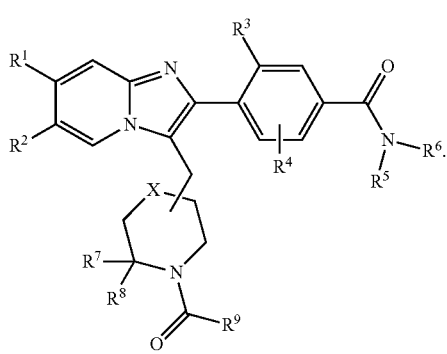

(IL)

In some embodiments, each of $R^7$ and $R^8$ is methyl.

$R^9$ is selected from the group consisting of $C_1$-$C_6$-alkyl, $C_3$-$C_6$-cycloalkyl, $C_1$-$C_6$-alkyl-$C_3$-$C_6$-cycloalkyl, halo-$C_1$-$C_6$-alkyl, $C_1$-$C_6$-alkoxy, halo-$C_1$-$C_6$-alkoxy, and $C_1$-$C_6$-alkoxy-$C_1$-$C_6$-alkyl.

In some embodiments, $R^9$ is $C_1$-$C_6$-alkyl.
In some embodiments, $R^9$ is methyl.
In some embodiments, $R^9$ is ethyl.
In some embodiments, $R^9$ is isopropyl.
In some embodiments, $R^9$ is halo-$C_1$-$C_6$-alkyl.
In some embodiments, $R^9$ is monofluoroisopropyl.
In some embodiments, $R^9$ is $C_1$-$C_6$-alkoxy.
In some embodiments, $R^9$ is methoxy.
In some embodiments, $R^9$ is t-butoxy.
In some embodiments, $R^9$ is $C_3$-$C_6$-cycloalkyl.
In some embodiments, $R^9$ is cyclopropyl.
In some embodiments, $R^9$ is cyclobutyl.
In some embodiments, $R^9$ is cyclobutyl.
In some embodiments, $R^9$ is $C_1$-$C_6$-alkoxy-$C_1$-$C_6$-alkyl.
In some embodiments, $R^9$ is methoxymethyl.
In some embodiments, $R^9$ is $C_1$-$C_6$-alkyl-$C_3$-$C_6$-cycloalkyl. In some such embodiments, for example, $R^9$ is methylcylclopropyl.

X is selected from a bond, $CH_2$, and O.

In some embodiments, X is a bond. In such embodiments, the compound corresponds to Formula (IM):

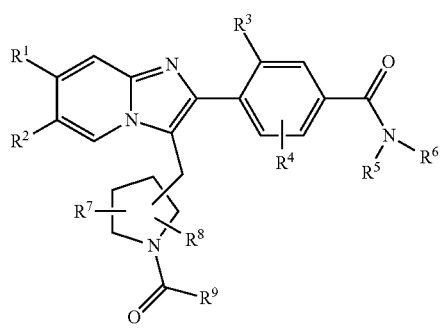

In some such embodiments, for example, the compound corresponds to Formula (IN):

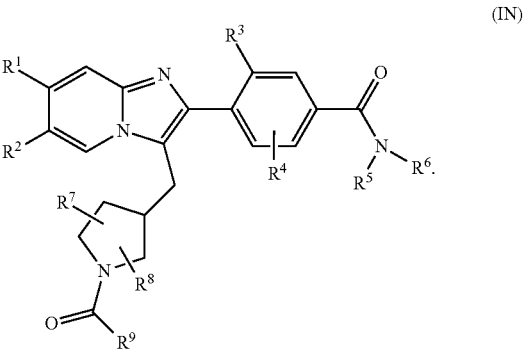

(IN)

In some embodiments, X is $CH_2$. In such embodiments, the compound corresponds to Formula (IO):

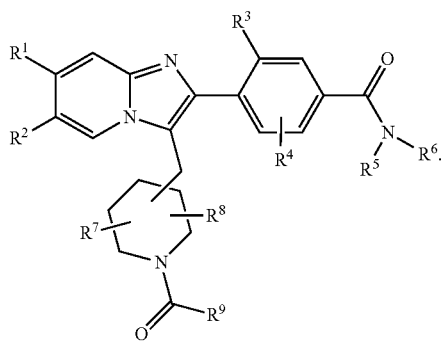

(IO)

In some such embodiments, for example, the compound corresponds to Formula (IP):

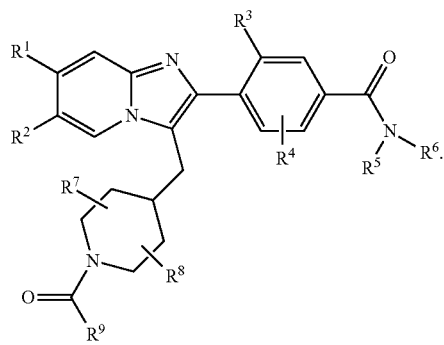

(IP)

In other embossments, the compound corresponds to Formula (IQ):

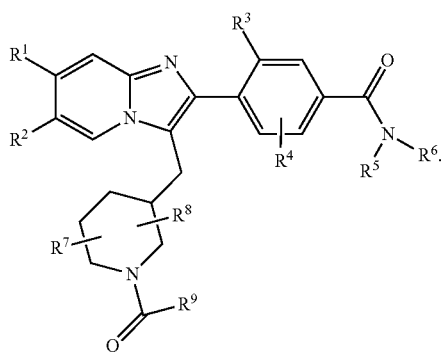

(IQ)

In some embodiments, X is O. In such embodiments, the compound corresponds to Formula (IR):

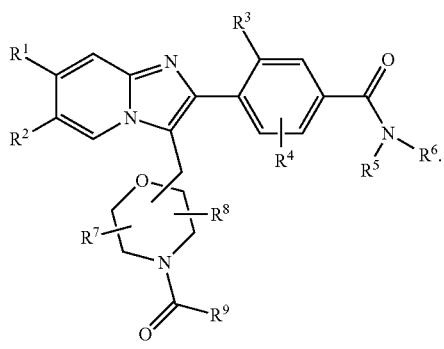

(IR)

In some such embodiments, the compound corresponds in structure to Formula (IS):

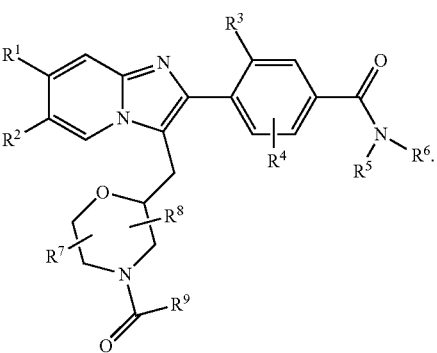

(IS)

In some embodiments of Formula (IS), the compound corresponds in structure to Formula (IT):

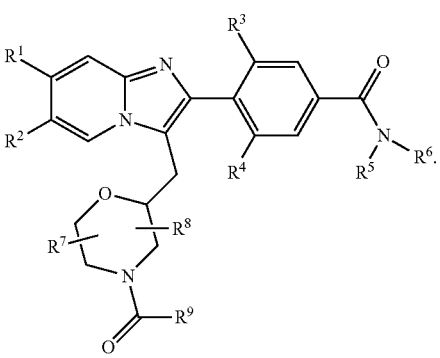

(IT)

In other embodiments of Formula (IS), the compound corresponds in structure to Formula (IU):

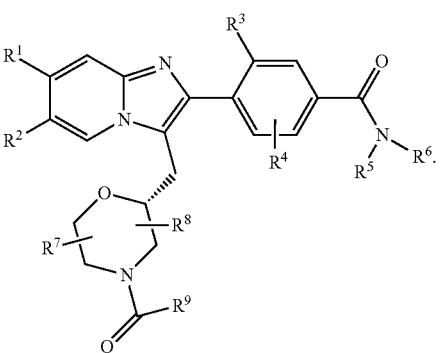

(IU)

In other embodiments of Formula (IS), the compound corresponds in structure to Formula (IV):

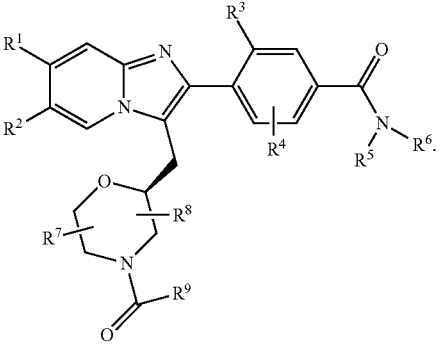

(IV)

In other embodiments, the compound corresponds in structure to Formula (IW):

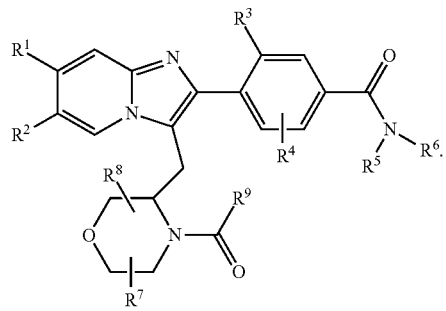

(IW)

In some such embodiments for Formula (IW), the compound corresponds in structure to Formula (IX):

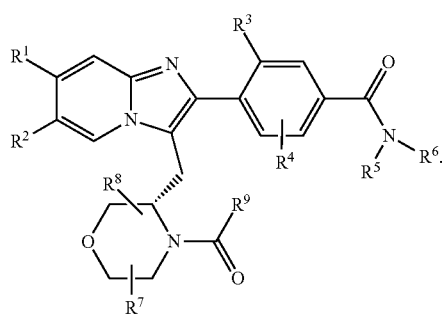

(IX)

In other embodiments for Formula (IW), the compound corresponds in structure to Formula (IY):

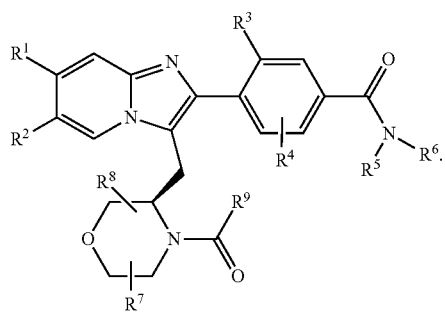

(IY)

Many of the compounds of this invention include at least one chiral carbon, i.e., the carbon of the morpholinyl that is linked through a methylene group to the imidazopyridine. To the extent a structure in this patent does not indicate the chirality, the structure is intended to encompass any single chiral isomer corresponding to that structure, as well as any mixture of chiral isomers (e.g., the racemate). Thus, for example, Formula I, which does not indicate the chirality, is intended to encompass any single isomer corresponding to the structure, as well as any mixture of chiral isomers. In some embodiments, a single chiral isomer is obtained by isolating it from a mixture of isomers (e.g., a racemate) using, for example, chiral chromatographic separation. In other embodiments, a single chiral isomer is obtained through direct synthesis from, for example, a chiral starting material.

When a structure shows the chirality of a carbon, it depicts the direction of one of the chiral carbon's substituents with a dark wedge or hashed wedge. Unless otherwise indicated, the carbon substituent pointing in the opposite direction is hydrogen. This notation is consistent with conventional organic chemistry nomenclature rules.

Contemplated salts of the compounds of this invention include both acid addition salts and base addition salts. A salt may be advantageous due to one or more of its chemical or physical properties, such as stability in differing temperatures and humidities, or a desirable solubility in water, oil, or other solvent. In some instances, a salt may be used to aid in the isolation or purification of the compound. In some embodiments (particularly where the salt is intended for administration to an animal, or is a reagent for use in making a compound or salt intended for administration to an animal), the salt is pharmaceutically acceptable.

In general, an acid addition salt can be prepared using various inorganic or organic acids. Such salts can typically be formed by, for example, mixing the compound with an acid (e.g., a stoichiometric amount of acid) using various methods known in the art. This mixing may occur in water, an organic solvent (e.g., ether, ethyl acetate, ethanol, isopropanol, or acetonitrile), or an aqueous/organic mixture. Examples of inorganic acids that typically may be used to form acid addition salts include hydrochloric, hydrobromic, hydroiodic, nitric, carbonic, sulfuric, and phosphoric acid. Examples of organic acids include, for example, aliphatic, cycloaliphatic, aromatic, araliphatic, heterocyclic, carboxylic, and sulfonic classes of organic acids. Specific examples of organic salts include cholate, sorbate, laurate, acetate, trifluoroacetate, formate, propionate, succinate, glycolate, gluconate, digluconate, lactate, malate, tartaric acid (and derivatives thereof, e.g., dibenzoyltartrate), citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate (and derivatives thereof), embonate (pamoate), ethanesulfonate, benzenesulfonate, pantothenate, 2-hydroxyethanesulfonate, sulfanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate. In some embodiments, the salt comprises a hydrochloride, hydrobromide, phosphate, acetate, fumarate, maleate, tartrate, citrate, methanesulphonate, or p-toluenesulphonate salt.

With respect to base-addition salts, it may be possible to make an alkali metal (such as sodium, potassium, or lithium) or an alkaline earth metal (such as a calcium) salt by treating a compound of this invention having a suitably acidic proton with an alkali metal or alkaline earth metal hydroxide or alkoxide (e.g., an ethoxide or methoxide) or a suitably basic organic amine (e.g., a choline or meglumine) in an aqueous medium.

The compounds of Formula I and salts thereof are intended to encompass any tautomer that may form. A "tautomer" is any other structural isomer that exists in equilibrium resulting from the migration of a hydrogen atom, e.g., amide-imidic acid tautomerism.

It is contemplated that an amine of a compound of Formula I or a salt thereof may form an N-oxide. Such an N-oxide is intended to be encompassed by the compounds of Formula I and salts thereof. An N-oxide can generally be formed by treating an amine with an oxidizing agent, such as hydrogen peroxide or a per-acid (e.g., a peroxycarboxylic acid). See, e.g., Advanced Organic Chemistry, by Jerry March, 4$^{th}$ Edition, Wiley Interscience. N-oxides also can be made by reacting the amine with m-chloroperoxybenzoic acid (MCPBA), for example, in an inert solvent, such as dichloromethane. See L. W. Deady, *Syn. Comm.*, 7, pp. 509-514 (1977).

It is contemplated that a compound of Formula I or salt thereof could form isolatable atropisomer in certain solvents at certain temperatures. The compounds of Formula I and salts thereof are intended to encompass any such atropisomers. Atropisomers can generally be isolated using, for example, chiral LC.

The compounds of Formula I and salts thereof are intended to encompass any isotopically-labeled (or "radiolabeled") derivatives of a compound of Formula I or salt thereof. Such a derivative is a derivative of a compound of Formula I or salt thereof wherein one or more atoms are replaced by an atom having an atomic mass or mass number different from the atomic mass or mass number typically found in nature. Examples of radionuclides that may be incorporated include $^2$H (also written as "D" for deuterium), $^3$H (also written as "T" for tritium), $^{11}$C, $^{13}$C, $^{14}$C, $^{13}$N, $^{15}$N, $^{15}$O, $^{17}$O, $^{18}$O, $^{18}$F, $^{36}$Cl, $^{82}$Br, $^{75}$Br, $^{76}$Br, $^{77}$Br, $^{123}$I, $^{124}$I, $^{125}$I, and $^{131}$I. The radionuclide that is used will depend on the specific application of that radio-labeled derivative. For example, for in vitro receptor labeling and competition assays, $^3$H or $^{14}$C are often useful. For radio-imaging applications, $^{11}$C or $^{18}$F are often useful. In some embodiments, the radionuclide is $^3$H. In some embodiments, the radionuclide is $^{14}$C. In some embodiments, the radionuclide is $^{11}$C. And in some embodiments, the radionuclide is $^{18}$F.

The compounds of Formula I and salts thereof are intended to cover all solid state forms of the compounds of Formula I and salts thereof. The compounds of Formula I and salts thereof also are intended to encompass all solvated (e.g., hydrated) and unsolvated forms of the compounds of Formula I and salts thereof.

The compounds of Formula I and salts thereof also are intended to encompass coupling partners in which a compound of Formula I or a salt thereof is linked to a coupling partner by, for example, being chemically coupled with the compound or salt or physically associated with it. Examples of coupling partners include a label or reporter molecule, a supporting substrate, a carrier or transport molecule, an effector, a drug, an antibody, or an inhibitor. Coupling partners can be covalently linked to a compound of Formula I or salt thereof via an appropriate functional group on the compound, such as a hydroxyl, carboxyl, or amino group. Other derivatives include formulating a compound of Formula I or a salt thereof with liposomes.

This invention provides, in part, methods to treat various disorders in animals, particularly mammals. Mammals include, for example, humans. Mammals also include, for example, companion animals (e.g., dogs, cats, and horses), livestock animals (e.g., cattle and swine); lab animals (e.g., mice and rats); and wild, zoo, and circus animals (e.g., bears, lions, tigers, apes, and monkeys).

As shown below in Example 48, compounds of this invention have been observed to modulate, and, in particular, act as antagonist against, P2X3. Accordingly, it is believed that the compounds and salts of this invention can be used to modulate P2X3 and/or P2X2/3 to treat various conditions mediated by (or otherwise associated with) P2X3 and/or P2X2/3. In some embodiments, the compounds and salts of this invention exhibit one or more of the following characteristics: desirable potency, desirable efficacy, desirable stability on the shelf, desirable tolerability for a range of patients, and desirable safety.

It is contemplated that a compound or salt of this invention may be used to treat, for example, pain. Such pain may be, for example, chronic pain, neuropathic pain, acute pain, back pain, cancer pain, pain caused by rheumatoid arthritis, migraine, and visceral pain.

It also is contemplated that a compound or salt of this invention may be used to treat a urinary tract disorder. Such disorders include, for example, over-active bladder (also known as urinary incontinence), pelvic hypersensitivity, and urethritis.

It also is contemplated that a compound or salt of this invention may be used to treat a gastrointestinal disorder. Such disorders include, for example, constipation and functional gastrointestinal disorders (e.g., irritable bowel syndrome or functional dyspepsia).

It also is contemplated that a compound or salt of this invention may be used to treat cancer.

It also is contemplated that a compound or salt of this invention may be used to treat a cardiovascular disorder or for cardioprotection following myocardial infarction.

It also is contemplated that a compound or salt of this invention may be useful as an immunomodulator, especially for treating an autoimmune disease (e.g., arthritis); for a skin graft, organ transplant, or similar surgical need; for a collagen disease; for an allergy; or as an anti-tumor or antiviral agent.

It also is contemplated that a compound or salt of this invention may be used to treat multiple sclerosis, Parkinson's disease, and Huntington's chorea.

It also is contemplated that a compound or salt of this invention may be useful to treat depression, anxiety, a stress-related disorder (e.g., a post-traumatic stress disorder, panic disorder, social phobia, or obsessive compulsive disorder), premature ejaculation, a mental illness, traumatic brain injury, stroke, Alzheimer's disease, spinal injury, drug addiction (e.g., treatment of alcohol, nicotine, opioid, or other drug abuse), or a disorder of the sympathetic nervous system (e.g., hypertension).

It also is contemplated that a compound or salt of this invention may be used to treat diarrhea.

It also is contemplated that a compound or salt of this invention may be useful to treat a pulmonary disorder, such as, for example, asthma, a cough or lung edema.

It is contemplated that a compound of Formula I or a pharmaceutically acceptable salt thereof may be administered orally, buccally, vaginally, rectally, via inhalation, via insufflation, intranasally, sublingually, topically, or parenterally (e.g., intramuscularly, subcutaneously, intraperitoneally, intrathoracially, intravenously, epidurally, intrathecally, intracerebroventricularly, or by injection into the joints).

In some embodiments, a compound or salt of this invention is administered orally.

In some embodiments, a compound or salt of this invention is administered intravenously.

In some embodiments, a compound or salt of this invention is administered intramuscularly.

In some embodiments, a compound or salt of this invention is used to make a medicament (i.e., a pharmaceutical composition). In general, the pharmaceutical composition comprises a therapeutically effective amount of the compound or salt. Pharmaceutical compositions comprising a compound or salt of this invention can vary widely. Although it is contemplated that a compound or salt of this invention could be administered by itself (i.e., without any other active or inactive ingredient), the pharmaceutical composition normally will instead comprise one or more additional active ingredients and/or inert ingredients. The inert ingredients present in the pharmaceutical compositions of this invention are sometimes collectively referred to as "carriers, diluents, and excipients." Methods for making pharmaceutical compositions and the use of carriers, diluents, and excipients are well known in the art. See, e.g., for example, *Remington's Pharmaceutical Sciences*, Mack Publishing Company, Easton, Pa., 15th Edition, 1975.

Pharmaceutical compositions comprising a compound of Formula I or pharmaceutically acceptable salt thereof can vary widely. For example, it is contemplated that the compositions may be formulated for a variety of suitable routes and means of administration, including oral, rectal, nasal, topical, buccal, sublingual, vaginal, inhalation, insufflation, or parenteral administration. It is contemplated that such compositions may, for example, be in the form of solids, aqueous or oily solutions, suspensions, emulsions, creams, ointments, mists, gels, nasal sprays, suppositories, finely divided powders, and aerosols or nebulisers for inhalation. In some embodiments, the composition comprises a solid or liquid dosage form that may be administered orally.

Solid form compositions may include, for example, powders, tablets, dispersible granules, capsules, cachets, and suppositories. A solid carrier may comprise one or more substances. Such substances are generally inert. A carrier also may act as, for example, a diluent, flavoring agent, solubilizer, lubricant, preservative, stabilizer, suspending agent, binder, or disintegrating agent. It also may act as, for example, an encapsulating material. Examples of often suitable carriers include pharmaceutical grade mannitol, lactose, magnesium carbonate, magnesium stearate, talc, lactose, sugar (e.g., glucose and sucrose), pectin, dextrin, starch, tragacanth, cellulose, cellulose derivatives (e.g., methyl cellulose and sodium carboxymethyl cellulose), sodium saccharin, low-melting wax, and cocoa butter.

In powders, the carrier is typically a finely divided solid, which is in a mixture with the finely divided active component. In tablets, the active component is typically mixed with the carrier having the desirable binding properties in suitable proportions and compacted into the desired shape and size.

For preparing suppository compositions, a low-melting wax (e.g., a mixture of fatty acid glycerides and cocoa butter) is typically first melted, followed by dispersing the active ingredient therein by, for example, stirring. The molten homogeneous mixture is then poured into convenient-sized molds and allowed to cool and solidify. Examples of non-irritating excipients that may be present in suppository compositions include, for example, cocoa butter, glycerinated gelatin, hydrogenated vegetable oils, mixtures of polyethylene glycols of various molecular weights, and fatty acid esters of polyethylene glycol.

Liquid compositions can be prepared by, for example, dissolving or dispersing the compound or a salt of this invention in a carrier, such as, for example, water, water/propylene glycol solutions, saline aqueous dextrose, glycerol, or ethanol. In some embodiments, aqueous solutions for oral administration can be prepared by dissolving a compound or salt of this invention in water with a solubilizer (e.g., a polyethylene glycol). Colorants, flavoring agents, stabilizers, and thickening agents, for example, also may be added. In some embodiments, aqueous suspensions for oral use can be made by dispersing the compound or salt of this invention in a finely divided form in water, together with a viscous material, such as, for example, one or more natural synthetic gums, resins, methyl cellulose, sodium carboxymethyl cellulose, or other suspending agents. If desired, the liquid composition also may contain other non-toxic auxiliary inert ingredients, such as, for example, wetting or emulsifying agents, pH buffering agents and the like, for example, sodium acetate, sorbitan monolaurate, triethanolamine sodium acetate, sorbitan monolaurate, triethanolamine oleate, etc. Such compositions also may contain other ingredients, such as, for example, one or more pharmaceutical adjuvants.

In some embodiments, the pharmaceutical composition comprises from about 0.05% to about 99% (by weight) of a compound or salt of this invention. In some such embodiments, for example, the pharmaceutical composition comprises from about 0.10% to about 50% (by weight) of a compound or salt of this invention.

When a compound or salt of this invention is administered as a sole therapy for treating a disorder, a "therapeutically effective amount" is an amount sufficient to reduce or completely alleviate symptoms or other detrimental effects of the disorder; cure the disorder; reverse, completely stop, or slow the progress of the disorder; reduce the risk of the disorder getting worse; or delay or reduce the risk of onset of the disorder.

The optimum dosage and frequency of administration will depend on the particular condition being treated and its severity; the species of the patient; the age, size and weight, diet, and general physical condition of the particular patient; brain/body weight ratio; other medication the patient may be taking; the route of administration; the formulation; and various other factors known to physicians (in the context of human patients), veterinarians (in the context of non-human patients), and others skilled in the art.

It is contemplated that in some embodiments, the optimum amount of a compound or salt of this invention is at least about 10 pg/kg of body weight per day. In some embodiments, the optimum amount is no greater than about 100 mg/kg of body weight per day. In some embodiments, the optimum amount is from about 10 pg/kg to about 100 mg/kg of body weight per day. In some embodiments, the optimum amount is from about 0.01 to about 10 mg/kg of body weight per day. In some embodiments, the optimum amount is from about 2 to about 20 mg/kg of body weight per day. In some embodiments, the optimum amount is from about 2.5 to about 8 mg/kg of body weight per day. In still other embodiments, the optimum amount is from about 0.8 to about 2.5 mg/kg of body weight per day.

It is contemplated that the pharmaceutical compositions can be in one or more unit dosage forms. Accordingly, the composition may be divided into unit doses containing appropriate quantities of the active component. The unit dosage form can be, for example, a capsule, cachet, or tablet itself, or it can be the appropriate number of any of these in packaged forms. The unit dosage form alternatively can be a packaged preparation in which the package contains discrete quantities of the composition, such as, for example, packeted tablets, capsules, or powders in vials or ampoules. Unit dosage forms may be prepared by, for example, various methods well known in the art of pharmacy.

It is contemplated that a dosage can be given once daily or in divided doses, such as, for example, from 2 to 4 times per day. In some embodiments, the dose is conventionally formulated in an oral dosage form by compounding from about 5 to about 250 mg per unit of dosage with, for example, one or more inert or active ingredients using accepted pharmaceutical practices.

In some embodiments, a compound or salt of this invention is administered concurrently, simultaneously, sequentially, or separately with one or more other pharmaceutically active compounds. In some such embodiments, the other pharmaceutically active compound(s) is/are selected from the following:

(i) Antidepressants, which are contemplated to include, for example, one or more of agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, mirtazeprine, nortriptyline, nefazodone, paroxetine, phenelzine, protriptyline, ramelteon, reboxetine, robalzotan, selegiline, sertraline, sibutramine, thionisoxetine, tranylcypromaine, trazodone, trimipramine, venlafaxine and equivalents and pharmaceutically active isomer(s) and metabolite(s) thereof (ii) Antipsychotics, which are contemplated to include, for example, one or more of quetiapine and pharmaceutically active isomer(s) and metabolite(s) thereof; and amisulpride, aripiprazole, asenapine, benzisoxidil, bifeprunox, carbamazepine, clozapine, chlorpromazine, debenzapine, dibenzapine, divalproex, droperidol, duloxetine, eszopiclone, fluphenazine, haloperidol, iloperidone, lamotrigine, lithium, loxapine, mesoridazine, molindone, olanzapine, paliperidone, perlapine, perphenazine, phenothiazine, phenylbutylpiperidine, pimozide, prochlorperazine, risperidone, sertindole, sulpiride, suproclone, suriclone, thioridazine, thiothixene, trifluoperazine, trimetozine, valproate, valproic acid, zopiclone, zotepine, ziprasidone, and equivalents thereof (iii) Anxiolytics, which are contemplated to include, for example, one or more of alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, suriclone, tracazolate, trepipam, temazepam, triazolam, uldazepam, zolazepam and equivalents and pharmaceutically active isomer(s) and metabolite(s) thereof (iv) Anticonvulsants, which are contemplated to include, for example, one or more of carbamazepine, oxcarbazepine, valproate, lamotrogine, gabapentin, topiramate, phenytoin, ethoxuximide, and equivalents and pharmaceutically active isomer(s) and metabolite(s) thereof (v) Alzheimer's therapies, which are contemplated to include, for example, donepezil, galantamine, memantine, rivastigmine, tacrine and equivalents and pharmaceutically active isomer(s) and metabolite(s) thereof (vi) Parkinson's therapies and agents for the treatment of extrapyramidal symtpoms, which are contemplated to include, for example, one or more of levodopa, carbidopa, amantadine, pramipexole, ropinirole, pergolide, cabergoline, apomorphine, bromocriptine, MAOB inhibitors (e.g., selegine and rasagiline), COMT inhibitors (e.g., entacapone and tolcapone), alpha-2 inhibitors, anticholinergics (e.g., benztropine, biperiden, orphenadrine, procyclidine, and trihexyphenidyl), dopamine reuptake inhibitors, NMDA antagonists, Nicotine agonists, Dopamine agonists, and inhibitors of neuronal nitric oxide synthase, and equivalents and pharmaceutically active isomer(s) and metabolite(s) thereof (vii) Stroke therapies, which are contemplated to include, for example, one or more of abciximab, activase, disufenton sodium, citicoline, crobenetine, desmoteplase, repinotan, traxoprodil, and equivalents and pharmaceutically active isomer(s) and metabolite(s) thereof (viii) Urinary incontinence therapies, which are contemplated to include, for example, one or more of darafenacin, dicyclomine, falvoxate, imipramine, desipramine, oxybutynin, propiverine, propanthedine, robalzotan, solifenacin, alfazosin, doxazosin, terazosin, tolterodine, and equivalents and pharmaceutically active isomer(s) and metabolite(s) thereof (ix) Insomnia therapies, which are contemplated to include, for example, one or more of allobarbital, alonimid, amobarbital, benzoctamine, butabarbital, capuride, chloral, cloperidone, clorethate, dexclamol, estazolam, eszopicline, ethchlorvynol, etomidate, flurazepam, glutethimide, halazepam, hydroxyzine, mecloqualone, melatonin, mephobarbital, methaqualone, midaflur, midazolam, nisobamate, pagoclone, pentobarbital, perlapine, phenobarbital, propofol, quazepam, ramelteon, roletamide, suproclone, temazepam, triazolam, triclofos, secobarbital, zaleplon, zolpidem, zopiclone, and equivalents and pharmaceutically active isomer(s) and metabolite(s) thereof (x) Mood stabilizers, which are contemplated to include, for example, one or more of carbamazepine, divalproex, gabapentin, lamotrigine, lithium, olanzapine, quetiapine, valproate, valproic acid, verapamil, and equivalents and pharmaceutically active isomer(s) and metabolite(s) thereof (xi) Medications for treating obesity, such as, for example, orlistat, sibutramine, rimonabant, and equivalents and pharmaceutically active isomer(s) and metabolite(s) thereof (xii) Agents for treating ADHD, which are contemplated to include, for example, one or more of amphetamine, methamphetamine, dextroamphetamine, atomoxetine, methylphenidate, dexmethylphenidate, modafinil, and equivalents and pharmaceutically active isomer(s) and metabolite(s) thereof (xiii) Agents used to treat substance abuse disorders, dependence, and withdrawal, which are contemplated to include, for example, one or more of nicotine replacement therapies (e.g., gum, patches, and nasal spray); nicotinergic receptor agonists, partial agonists, and antagonists, (e.g., varenicline); acomprosate; bupropion; clonidine; disulfiram; methadone; naloxone; naltrexone; and equivalents and pharmaceutically active isomer(s) and metabolite(s) thereof.

In some embodiments, the other pharmaceutically active ingredient(s) comprises an atypical antipsychotic agent. Atypical antipsychotic agents include, for example, olanzapine (marketed as Zyprexa), aripiprazole (marketed as Abilify), risperidone (marketed as Risperdal), quetiapine (marketed as Seroquel), clozapine (marketed as Clozaril), ziprasidone (marketed as Geodon), and olanzapine/fluoxetine (marketed as Symbyax).

In some embodiments, the other pharmaceutically active ingredient(s) comprises a selective serotonin reuptake inhibitor (or "serotonin-specific reuptake inhibitor" or SSRI"). Such agents include, for example, fluoxetine (marketed as, for example, Prozac), paroxetine (marketed as, for example, Paxil), citalopram (marketed as, for example, Celexa), dapoxetine, mesembrine, excitalopram (marketed as, for example, Lexapro), fluvoxamine (marketed as, for example, Luvox), zimelidine (marketed as, for example, Zelmid), and sertraline (marketed as, for example, Zoloft).

In some embodiments, a compound or salt of this invention is administered as part of a combination therapy with radiotherapy.

In some embodiments, a compound or salt of this invention is administered as a combination therapy with chemotherapy. Such chemotherapy may include one or more of the following categories of anti-tumour agents:

(i) Antiproliferative/antineoplastic drugs, which are contemplated to include, for example, alkylating agents, such as cis-platin, oxaliplatin, carboplatin, cyclophosphamide, nitrogen mustard, melphalan, chlorambucil, busulphan, temozolamide, and nitrosoureas; antimetabolites, such as gemcitabine and antifolates (e.g., fluoropyrimidines (like 5-fluorouracil and tegafur), raltitrexed, methotrexate, cytosine arabinoside, and hydroxyurea); antitumour antibiotics, such as anthracyclines (e.g., adriamycin, bleomycin, doxorubicin, daunomycin, epirubicin, idarubicin, mitomycin-C, dactinomycin and mithramycin); antimitotic agents, such as vinca alkaloids (e.g., vincristine, vinblastine, vindesine, and vinorelbine), taxoids (e.g., taxol and taxotere), and polokinase inhibitors; and topoisomerase inhibitors, such as epipodophyllotoxins (e.g., etoposide and teniposide), amsacrine, topotecan, and camptothecin.

(ii) Cytostatic agents, which are contemplated to include, for example, antioestrogens, such as tamoxifen, fulvestrant, toremifene, raloxifene, droloxifene, and iodoxyfene; anti-androgens, such as bicalutamide, flutamide, nilutamide, and cyproterone acetate; LHRH antagonists; LHRH agonists, such as goserelin, leuprorelin, and buserelin; progestogens, such as megestrol acetate; aromatase inhibitors, such as anastrozole, letrozole, vorazole, and exemestane; and 5α-reductase inhibitors, such as finasteride.

(iii) Anti-invasion agents, which are contemplated to include, for example, c-Src kinase family inhibitors, such as 4-(6-chloro-2,3-methylenedioxyanilino)-7-[2-(4-methylpiperazin-1-yl)ethoxy]-5-tetrahydropyran-4-yloxyquinazoline (AZD0530, Int'l Patent Appl. Publ. WO01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825, *J. Med. Chem.*, vol. 47, pp. 6658-6661 (2004)), and bosutinib (SKI-606); metalloproteinase inhibitors, such as marimastat; inhibitors of urokinase plasminogen activator receptor function; and antibodies to heparanase.

(iv) Inhibitors of growth factor function, which are contemplated to include, for example, growth factor antibodies; growth factor receptor antibodies, such as the anti-erbB2 antibody trastuzumab (Herceptin™), the anti-EGFR antibody panitumumab, the anti-erbB1 antibody cetuximab (Erbitux, C225), and growth factor or growth factor receptor antibodies disclosed by Stern et al., *Critical reviews in oncology/haematology*, vol. 54, pp. 11-29 (2005); tyrosine kinase inhibitors, such as inhibitors of the epidermal growth factor family (e.g., EGFR family tyrosine kinase inhibitors like N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774), and 6-acrylamido-N-(3-chloro-4-fluorophenyl)-7-(3-morpholinopropoxy)-quinazolin-4-amine (CI 1033)) and erbB2 tyrosine kinase inhibitors (e.g., lapatinib); inhibitors of the hepatocyte growth factor family; inhibitors of the insulin growth factor family; inhibitors of the platelet-derived growth factor family, such as imatinib and nilotinib (AMN107); inhibitors of serine/threonine kinases, such as Ras/Raf signalling inhibitors (e.g., farnesyl transferase inhibitors like sorafenib (BAY 43-9006), tipifarnib (R115777), and lonafarnib (SCH66336)); inhibitors of cell signalling through MEK and/or AKT kinases; c-kit inhibitors; abl kinase inhibitors, PI3 kinase inhibitors; Plt3 kinase inhibitors; CSF-1R kinase inhibitors; IGF receptor (insulin-like growth factor) kinase inhibitors); aurora kinase inhibitors, such as AZD1152, PH739358, VX-680, MLN8054, R763, MP235, MP529, VX-528, and AX39459; and cyclin dependent kinase inhibitors, such as CDK2 and CDK4 inhibitors.

(v) Antiangiogenic agents, which are contemplated to include, for example, those that inhibit the effects of vascular endothelial growth factor, such as anti-vascular endothelial cell growth factor antibody bevacizumab (Avastin™) and a VEGF receptor tyrosine kinase inhibitor (e.g., vandetanib (ZD6474), vatalanib (PTK787), sunitinib (SU11248), axitinib (AG-013736), pazopanib (GW 786034), and 4-(4-fluoro-2-methylindol-5-yloxy)-6-methoxy-7-(3-pyrrolidin-1-ylpropoxy)quinazoline (AZD2171, Example 240 in Intl. Patent Appl. Publ. WO 00/47212); compounds disclosed in Int'l Patent Appl. Publ. WO97/22596, WO 97/30035, WO 97/32856, and WO 98/13354; and compounds that work by other mechanisms, such as linomide, inhibitors of integrin αvβ3 function, and angiostatin.

(vi) Vascular damaging agents, which are contemplated to include, for example, combretastatin A4 and compounds disclosed in Int'l Patent Appl. Publ. WO 99/02166, WO 00/40529, WO 00/41669, WO 01/92224, WO 02/04434, and WO 02/08213.

(vii) Endothelin receptor antagonists, which are contemplated to include, for example, zibotentan (ZD4054) and atrasentan.

(viii) Antisense therapies, which are contemplated to include, for example, those that are directed to the targets listed above, such as ISIS 2503 (an anti-ras antisense).

(ix) Gene therapy approaches, which are contemplated to include, for example, approaches to replace aberrant genes, such as aberrant p53, BRCA1, or BRCA2; GDEPT (gene-directed enzyme pro-drug therapy) approaches, such as those using cytosine deaminase, thymidine kinase, or a bacterial nitroreductase enzyme; and approaches to increase patient tolerance to chemotherapy or radiotherapy, such as multi-drug resistance gene therapy.

(x) Immunotherapy approaches, which are contemplated to include, for example, ex-vivo and in-vivo approaches to increase the immunogenicity of patient tumour cells, such as transfection with cytokines (e.g., interleukin 2, interleukin 4, or granulocyte-macrophage colony stimulating factor); approaches to decrease T-cell anergy; approaches using transfected immune cells, such as cytokine-transfected dendritic cells; approaches using cytokine-transfected tumour cell lines; and approaches using anti-idiotypic antibodies.

It also is contemplated that a compound or salt of this invention may be useful as an analgesic agent for use during general anesthesia or monitored anesthesia care. Combinations of agents with different properties are often used to achieve a balance of effects needed to maintain the anesthetic state (e.g., amnesia, analgesia, muscle relaxation, and sedation). Such a combination may include, for example, one or more inhaled anesthetics, hypnotics, anxiolytics, neuromuscular blockers, and/or opioids.

In some embodiments in which a combination therapy is used, the amount of the compound or salt of this invention and the amount of the other pharmaceutically active agent(s)

are, when combined, therapeutically effective to treat a targeted disorder in the animal patient. In this context, the combined amounts are "therapeutically effective amount" if they are, when combined, sufficient to reduce or completely alleviate symptoms or other detrimental effects of the disorder; cure the disorder; reverse, completely stop, or slow the progress of the disorder; reduce the risk of the disorder getting worse; or delay or reduce the risk of onset of the disorder. Typically, such amounts may be determined by one skilled in the art by, for example, starting with the dosage range described in this patent for the compound or salt of this invention and an approved or otherwise published dosage range(s) of the other pharmaceutically active compound(s).

When used in a combination therapy, it is contemplated that the compound or salt of this invention and the other active ingredients may be administered in a single composition, completely separate compositions, or a combination thereof. It also is contemplated that the active ingredients may be administered concurrently, simultaneously, sequentially, or separately. The particular composition(s) and dosing frequency(ies) of the combination therapy will depend on a variety of factors, including, for example, the route of administration, the condition being treated, the species of the patient, any potential interactions between the active ingredients when combined into a single composition, any interactions between the active ingredients when they are administered to the animal patient, and various other factors known to physicians (in the context of human patients), veterinarians (in the context of non-human patients), and others skilled in the art.

This invention also is directed, in part, to a kit comprising a compound of Formula I or a salt thereof. In some embodiments, the kit further comprises one or more additional components, such as, for example: (a) an apparatus for administering the compound of Formula I or a salt thereof (b) instructions for administering the compound of Formula I or a salt thereof; (c) a carrier, diluent, or excipient (e.g., a re-suspending agent); and (d) an additional active ingredient, which may be in the same and/or different dosage forms as the compound of Formula I or salt thereof. In some embodiments (particularly when the kit is intended for use in administering the compound of Formula I or salt thereof to an animal patient), the salt is a pharmaceutically acceptable salt.

EXAMPLES

The following examples are merely illustrative of embodiments of the invention, and not limiting to the remainder of this disclosure in any way.

In some instances in the following examples, compound structures are associated with compound names. In general, such names were generated from the structures using AutoNom 2000 within ISIS/Draw, ChemDraw 9.0.7, ISIS/Draw 2.5SP4, or ChemDraw 11.0.2. AutoNom (Automatic Nomenclature) and ChemDraw contain programs that assign systematic IUPAC (International Union of Pure and Applied Chemistry) chemical names to drawn structures at the press of a button. In some instances, however, the chemical names were manually revised to ensure compliance with IUPAC naming conventions. If there are any differences between a structure and name for a compound, the compound should be identified by the structure unless the context indicates otherwise.

Compound Preparation

Examples 1-47 below illustrate the preparation of a variety of different compounds of this invention and intermediates for making such compounds. It is expected that one skilled in the art of organic synthesis, after reading these examples alone or in combination with the general knowledge in the art, can adapt and apply the methods to make any compound encompassed by this invention. The general knowledge in the art includes, for example:

A) Conventional procedures for using protective groups and examples of suitable protective groups, which are described in, for example, *Protective Groups in Organic Synthesis*, T. W. Green, P. G. M. Wuts, Wiley-Interscience, New York (1999).

B) References discussing various organic synthesis reactions, include textbooks of organic chemistry, such as, for example, *Advanced Organic Chemistry, March 4th ed*, McGraw Hill (1992); and *Organic Synthesis*, Smith, McGraw Hill, (1994). They also include, for example, R. C. Larock, *Comprehensive Organic Transformations, 2nd ed*, Wiley-VCH: New York (1999); F. A. Carey; R. J. Sundberg, *Advanced Organic Chemistry, 2nd ed.*, Plenum Press: New York (1984); L. S. Hegedus, *Transition Metals in the Synthesis of Complex Organic Molecules, 2nd ed.*, University Science Books: Mill Valley, Calif. (1994); L. A. Paquette, Ed., *The Encyclopedia of Reagents for Organic Synthesis*, John Wiley: New York (1994); A. R. Katritzky, O. Meth-Cohn, CW. Rees, Eds., *Comprehensive Organic Functional Group Transformations*, Pergamon Press: Oxford, UK (1995); G. Wilkinson; F. G A. Stone; E. W. Abel, Eds., *Comprehensive Organometallic Chemistry*, Pergamon Press: Oxford, UK (1982); B. M. Trost; I. Fleming, *Comprehensive Organic Synthesis*, Pergamon Press: Oxford, UK (1991); A. R. Katritzky, CW. Rees Eds., *Comprehensive Heterocyclic Chemistry*, Pergamon Press: Oxford, UK (1984); A. R. Katritzky; CW. Rees, E. F. V. Scriven, Eds., *Comprehensive Heterocyclic Chemistry II*, Pergamon Press: Oxford, UK (1996); C. Hansen; P. G. Sammes; J. B. Taylor, Eds., *Comprehensive Medicinal Chemistry:* Pergamon Press: Oxford, UK (1990). In addition, recurring reviews of synthetic methodology and related topics include: *Organic Reactions*, John Wiley: New York; *Organic Syntheses*; John Wiley: New York; *The Total Synthesis of Natural Products*, John Wiley: New York; *The Organic Chemistry of Drug Synthesis*, John Wiley: New York; *Annual Reports in Organic Synthesis*, Academic Press: San Diego Calif.; and *Methoden der Organischen Chemie (Houben-Weyl)*, Thieme: Stuttgart, Germany.

C) References discussing heterocyclic chemistry include, for example, example, *Heterocyclic Chemistry*, J. A. Joule, K. Mills, G. F. Smith, 3rd ed., Cheapman and Hall, p. 189-225 (1995); and *Heterocyclic Chemistry*, T. L. Gilchrist, $2^{nd}$ ed. Longman Scientific and Technical, p. 248-282 (1992).

D) Databases of synthetic transformations, including Chemical Abstracts, which may be searched using either CAS Online or SciFinder; and Handbuch der Organischen Chemie (Beilstein), which may be searched using SpotFire.

All starting materials in the following compound preparation examples are commercially available or described in the literature. Air and moisture-sensitive liquids and solutions were transferred via syringe or cannula, and introduced into reaction vessels through rubber septa. Commercial grade reagents and solvents were used without further purification. The terms "concentration under reduced pressure" and "evaporated under reduce pressure" or "concentrated in vacuo" refer to use of a Buchi rotary evaporator at approximately 15 mm of Hg.

Microwave heating was performed either on a CEM Discover LabMate or on a Biotage Initiator System at the indicated temperature in the recommended microwave tubes.

Column chromatography (flash chromatography) was performed using 32-63 micron, 60 Å, silica gel prepacked cartridges (on a Biotage or ISCO system), or a glass column and air pressure. Preparative HPLC or LCMS (high pH or low pH) was performed using, for example, a Waters X-bridge Prep $C_{18}$ OBD (column size: 30×50 mm; particle size: 5 μm; mobile phase A: water 10 mM $NH_4HCO_3$ (pH 10) or water with 0.1% TFA; and mobile phase B: MeCN). Supercritical-fluid chromatography (SFC) was performed using a MiniGram SFC instrument from Mettler Toledo with a normal-phase ChiralCel OD-H or OJ-H column or a ChiralPak AS-H or AD-H or IC column (column size: 10×250 mm; particle size: 5 mm; flow rate: 10 mL/min) or ChiralPak IA or Lux Cellulose-2 or Lux Amylose-2 (column size: 4.6×250 mm; particle size: 5 mm; flow rate: 3.5 mL/min); Eluent: $CO_2$, with MeOH or i-PrOH or EtOH+ 0.1% dimethylethylamine (DMEA) or 1:1 isopropanol:acetonitrile+0.1% DMEA as a modifier; temperature: 35° C.; back pressure: 100 Bar; and UV detection at wavelength 215-254 nm.

Mass spectra were recorder using either Single-Quad mass spectrometers equipped with an electrospray ion source (ES) operated in a positive or negative ion mode or a Triple-Quad mass spectrometer configured with an atmospheric pressure chemical ionisation (APCI) ion source operated in positive and negative ion mode. The mass spectrometers were scanned between m/z 100-1000 with a scan time of 0.3 sec.

$^1$H NMR spectra were recorded on Varian NMR Spectrometer at 300 MHz, 400 MHz or alternatively on a Bruker Avance 500 NMR Spectrometer at 500 MHz.

Unless otherwise specified, HRMS analyses were performed on an Agilent 1100 HPLC with an Agilent MSD-TOF mass spectrometer and an Agilent 1100 Diode Array Detector using a Zorbax C-18 column (column size: 30×4.6 mm; particle size: 1.8 μm, gradient: 5-95% B in 4.5 min; flow rate: 3.5 mL/min; temperature: 70° C., eluents A: 0.05% TFA in $H_2O$; and eluent B: 0.05% TFA in $CH_3CN$).

Example 1

Preparation of 2,5-difluoro-4-formyl-N-methylbenzamide

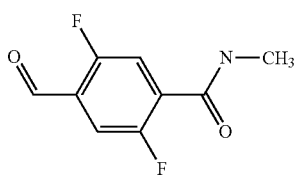

Part A. tert-butyl 4-bromo-2,5-difluorobenzoate

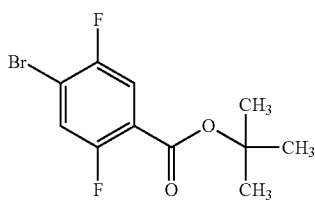 [SMILES: CC(C)(C)OC(=O)c1cc(F)c(Br)cc1F]

A solution of n-butylmagnesium chloride (2 M in THF) (19.9 mL, 39.7 mmol) was added to a solution of n-butyl-lithium (2.5 M in hexanes) (31.8 mL, 79.4 mmol) in anhydrous toluene (40 mL) at −10° C. The rate of addition was adjusted to keep the internal temperature at less than −5° C. The resulting mixture was stirred at −10° C. for 0.5 hr. Then a solution of 1,4-dibromo-2,5-difluorobenzene (25.4 g, 93.4 mmol) in dry toluene (80 mL) was added at such a rate as to maintain the internal temperature below −5° C. Afterward, the mixture was stirred at −10° C. for 2 hr. Next, a solution of di-tert-butyl dicarbonate (25.9 g, 0.12 mol) in toluene (40 mL) was added at such a rate as to maintain the internal temperature below −5° C. The mixture was then gradually warmed from −10° C. to 10° C. over a period of 2.5 hr. A 10% aqueous solution of citric acid (175 mL) was then added, and the phases were separated. The organic layer was washed 10% aqueous solution of citric acid (175 mL), dried over magnesium sulfate, filtered, and concentrated under reduced pressure to provide tert-butyl 4-bromo-2,5-difluorobenzoate that was used directly in the next step.

Part B. 4-bromo-2,5-difluorobenzoic acid

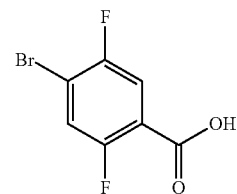 [SMILES: O=C(O)c1cc(F)c(Br)cc1F]

Trifluoromethanesulfonic acid (125 mL) was added to a solution of tert-butyl 4-bromo-2,5-difluorobenzoate (27.4 g, 93.4 mmol) in dichloromethane (125 mL) at 0° C. The resulting mixture was stirred at room temperature 3 hr, and then concentrated under reduced pressure. Half-saturated brine (100 mL) was then added to the residue, and the mixture was extracted with dichloromethane (2×90 mL). The organic layers were combined and the product was extracted with a 1 N aqueous solution of sodium hydroxide (1×90 mL and 1×50 mL). The combined aqueous layers were then acidified using a 3 N aqueous solution of hydrochloric acid (80 mL), and the product was extracted with EtOAc (3×100 mL). The combined organic layers were over magnesium sulfate, filtered, and concentrated under reduced pressure to provide 4-bromo-2,5-difluorobenzoic acid (13.1 g, 59%) as a solid. $^1$H NMR (300 MHz, DMSO-$d_6$) δ ppm 7.78 (dd, J=8.63, 6.23 Hz, 1H), 7.90 (dd, J=9.72, 5.58 Hz, 1H), 13.72 (br s, 1H).

Part C. 4-bromo-2,5-difluoro-N-methylbenzamide

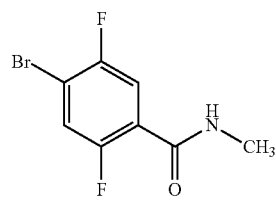

Methylamine hydrochloride (3.7 g, 54.9 mmol) and 1-hydroxybenzotriazole (5.99 g, 44.3 mmol) were added to a solution of 4-bromo-2,5-difluorobenzoic acid (10 g, 42.2 mmol) in N,N-dimethylformamide (70 mL). At 0° C., triethylamine (8.8 mL, 63.3 mmol) and N-(3-dimethylaminopropyl)-N'-ethylcarbodiimide hydrochloride (10.5 g, 54.9 mmol) were then added. The resulting mixture was stirred from 0° C. to room temperature for 16 hr. Water (140 mL) was then added, and the product was extracted with EtOAc (3×100 mL). The combined organic layers were washed with brine, dried over magnesium sulfate, filtered, and concentrated under reduced pressure. The residue was purified by silical gel flash chromatography eluting with 10-60% EtOAc in hexanes to give 4-bromo-2,5-difluoro-N-methylbenzamide (9.97 g, 95%) as a solid. ¹H NMR (300 MHz, CDCl₃) δ ppm 3.03 (d, J=4.73 Hz, 3H), 6.70 (br s, 1H), 7.38 (dd, J=10.37, 5.23 Hz, 1H), 7.88 (dd, J=8.65, 6.69 Hz, 1H).

Part D. 4-Cyano-2,5-difluoro-N-methylbenzamide

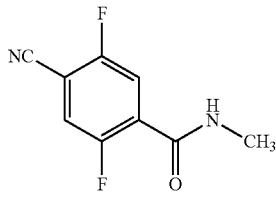

Zinc cyanide (2.81 g, 23.9 mmol), zinc dust (0.26 g, 3.99 mmol), tris(dibenzylideneacetone)dipalladium(0) (0.73 g, 0.80 mmol), 1,1'-bis(diphenylphosphino)ferrocene (0.88 g, 1.60 mmol) and sodium acetate (0.13 g, 1.60 mmol) were added to a solution of 4-bromo-2,5-difluoro-N-methylbenzamide (9.97 g, 39.9 mmol) in N,N-dimethylformamide (150 mL). N₂ was bubbled into the resulting mixture 5 min and then it was stirred at 100° C. for a period of 2 hr. The resulting mixture was cooled to room temperature and diluted with EtOAc (150 mL). The mixture was filtered on a diatomaceous earth pad, which subsequently was rinsed with EtOAc (2×25 mL). The filtrate was washed with water (300 mL) and the aqueous layer was back-extracted with EtOAc (2×50 mL) and the combined organic layers were dried with MgSO₄, filtered, and concentrated under reduced pressure. The crude residue was purified by silical gel flash chromatography eluting with 10-50% EtOAc in hexanes to give 4-cyano-2,5-difluoro-N-methylbenzamide (6.95 g, contains traces of N,N-dimethylformamide) as an solid. ¹H NMR (300 MHz, CDCl₃) δ ppm 3.05 (d, J=4.81 Hz, 3H), 6.78 (br s, 1H), 7.43 (dd, J=10.00, 4.78 Hz, 1H), 7.97 (dd, J=8.79, 5.85 Hz, 1H).

Part E. Preparation of 2,5-difluoro-4-formyl-N-methylbenzamide

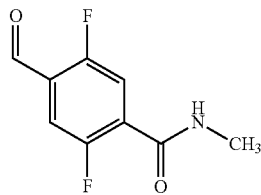

Raney nickel (50% in water) (6.38 g) was added to a solution of 4-cyano-2,5-difluoro-N-methylbenzamide (6.95 g, 35.4 mmol) in formic acid (94 mL) and water (32 mL). The mixture was stirred at 120° C. for 6 hr and then at room temperature for 16 hr. The resulting mixture was diluted with methanol (140 mL). Silica gel was added and the slurry was vigorously stirred 0.25 hr and then filtered on a diatomaceous earth pad. The pad was rinsed with methanol and the filtrate was concentrated under reduced pressure. The residue was purified by silical gel flash chromatography eluting with 10-60% EtOAc in hexanes to provide 2,5-difluoro-4-formyl-N-methylbenzamide (5.25 g, 74%) as a pale yellow solid. ¹H NMR (300 MHz, CDCl₃) δ ppm 3.06 (d, J=4.84 Hz, 3H), 6.83 (br s, 1H), 7.62 (dd, J=10.84, 5.20 Hz, 1H), 7.97 (dd, J=10.27, 5.62 Hz, 1H), 10.34 (d, J=2.98 Hz, 1H); MS (ESI) m/z 200.09 [M+H]⁺.

Example 2

Preparation of 3,5-difluoro-4-formyl-N-methylbenzamide

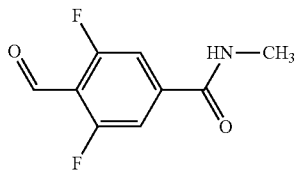

Part A. Preparation of 3,5-difluoro-4-formylbenzoic acid

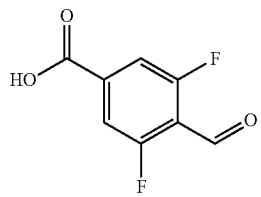 [SMILES: O=Cc1c(F)cc(C(=O)O)cc1F]

To a solution of 3,5-difluorobenzoic acid (291 g, 1.84 mol) in 2-methyltetrahydrofuran (4.35 L) was added TMEDA (604 mL, 4.03 mol) at room temperature. The resulting solution was cooled to −78° C. Afterward, n-BuLi (2.5 M in hexane) (1.77 L, 4.43 mol) was added drop-wise, during which the temperature of the mixture remained at less than −65° C. The mixture was then stirred at −78° C. for 1.5 hr. Anhydrous MeOCHO (239 mL, 3.88 mol) was added dropwise at a rate that allowed the temperature to be maintained at less than −65° C. The resulting solution was allowed to warm at room temperature, and then maintained a room temperature while being stirred for 18 hr. The mixture was then cooled to 0-5° C., and excess base was quenched with 6M aqueous HCl (2.2 L, 13.2 mol). The phases were then separated, and the aqueous layer was extracted 3 times with 2-methyltetrahydrofuran (3×500 mL). The combined organic phases were washed with saturated brine, dried over MgSO₄, filtered, and concentrated under vacuum. The residue was dissolved in ethyl acetate (350 mL) at reflux, and cooled to room temperature. Hexanes (480 mL) were then added, and the resulting mixture was further cooled to −15° C. The solid was collected by filtration, rinsed with hexanes, and dried under mechanical vacuum to form the title compound (122 g, 35%) as a solid. ¹H NMR (300 MHz, DMSO-d₆) δ ppm 7.63-7.70 (m, 2H), 10.23 (s, 1H); MS m/z (ESI) 187.17 [M+H]⁺.

Part B. Preparation of methyl 3,5-difluoro-4-formylbenzoate

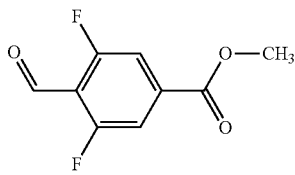

K$_2$CO$_3$ (14 g, 0.10 mol) and CH$_3$I (4.6 mL, 74.5 mmol) were added to a solution of 3,5-difluoro-4-formylbenzoic acid (12.6 g, 67.7 mmol) in DMF (135 mL). The resulting mixture was stirred at room temperature for 3 hr. Water (200 mL) was then added, and the mixture was extracted with EtOAc (3×150 mL). The combined organic layers were washed with brine, dried with MgSO$_4$, filtered, and concentrated under reduced pressure. The crude residue was purified by silica gel flash chromatography (0 to 20% EtOAc in hexanes) to form methyl 3,5-difluoro-4-formylbenzoate (6 g, 44%) as an oil that solidified upon standing. The solid was triturated in hexanes, filtered, and dried in vacuo to form pure methyl 3,5-difluoro-4-formylbenzoate (4.5 g, 33%) as a solid. $^1$H NMR (300 MHz, CDCl$_3$) δ ppm 3.97 (s, 3H), 7.62-7.68 (m, 2H), 10.39 (s, 1H); MS (ESI) m/z 201.30 [M+H]$^+$.

Part C. Preparation of 3,5-difluoro-4-formyl-N-methylbenzamide

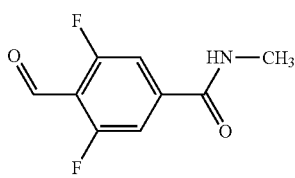

To an ice-cold solution of 3,5-difluoro-4-formylbenzoic acid (120 g, 645 mmol) in dichloromethane (1.5 L) and N,N-dimethylformamide (2.0 g, 27 mmol) was added oxalyl chloride (90 g, 709 mmol) drop-wise at a rate that allowed the mixture to not exceed an internal temperature of 10° C. The resulting mixture was stirred at the same temperature for 0.5 hr, warmed to room temperature, and stirred for an additional 1.5 hr. The solution was then cooled to 0° C., and aqueous methylamine (40%, 168 mL, 1.94 mol) was added drop-wise at a rate that allowed the mixture to not exceed an internal temperature of 7° C. Afterward, the mixture was quenched with aqueous HCl (2M, 335 mL, 670 mmol) and warmed to room temperature. The organic layer was separated, washed with brine (500 mL), dried over MgSO$_4$, filtered, and concentrated under vacuum. The resulting residual solid was taken in MTBE (500 mL), and the resulting mixture was heated to reflux for 0.5 hr, cooled to room temperature, and stirred for 18 hr. Afterward, the mixture was cooled to 0° C., filtered, rinsed with pentane, and dried under vacuum to form the title compound (103 g, 80%) as a solid. $^1$H NMR (300 MHz, CDCl$_3$) δ ppm 3.03 (d, J=4.86 Hz, 3H), 6.37 (br s, 1H), 7.36-7.42 (m, 2H), 10.36 (s, 1H); MS m/z 200.06 [M+H]$^+$ (ESI).

Example 3

Preparation of 4-formyl-N,3-dimethylbenzamide

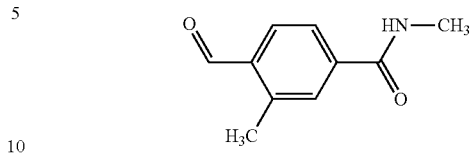

4-Bromo-3-methylbenzoic acid (10 g, 46.5 mmol) was suspended in dry THF (400 mL), purged with N$_2$, and cooled to 0° C. NaH (60% in oil) (1.95 g, 48.8 mmol) was added, and the resulting mixture was stirred at room temperature for 20 min. Afterward, the mixture was cooled to −78° C. tert-Butyllithium (1.7 M in pentane, 64 mL, 97.7 mmol) was then added at a rate that allowed the internal temperature to be maintained at less than −74° C. After the addition was complete, dry DMF (7.2 mL, 93 mmol) was added. The resulting mixture was stirred at −78° C. for 1 hr and then allowed to warm up to room temperature. After 1.5 hr, the excess base was quenched using 1 M HCl aqueous solution until the mixture had an acidic pH. The mixture was then extracted with EtOAc (3×200 mL), and the combined organic extracts were dried over MgSO$_4$, filtered, and concentrated under reduced pressure to afford 4-formyl-3-methyl benzoic acid. The acid was dissolved in DMF (30 mL), and MeNH$_2$—HCl (4.08 g, 60.5 mmol) and HOBt (6.91 g, 51.2 mmol) were added. The resulting mixture was cooled to 0° C., and then Et$_3$N (26 mL, 0.19 mol) was added, followed by EDC-HCl (11.6 g, 60.5 mmol). The mixture was stirred at room temperature for 16 hr, and then filtered on a silica gel pad, which was subsequently rinsed with EtOAc. The filtrate was concentrated under reduced pressure, and the residue was purified by silica gel flash column chromatography (Hex/EtOAc 1:1 to 1:2) to provide the title compound (4.5 g, 55%) as a solid. $^1$H NMR (300 MHz, CDCl$_3$) δ 2.43 (s, 3H), 3.00 (d, J=4.9 Hz, 3H), 6.12 (m, 1H), 7.39 (dd, J=8.2, 2.3 Hz, 1H), 7.57 (d, J=8.2 Hz, 1H), 7.64 (d, J=2.1 Hz, 1H).

Example 4

Alternative preparation of 4-formyl-N,3-dimethylbenzamide

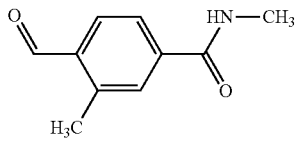

Part A. Preparation of 4-cyano-N,3-dimethylbenzamide

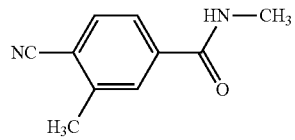

A mixture of 4-bromo-N-ethyl-3-methylnenzamide (3.76 g, 16.5 mmol, can be synthesized according to the following reference Oxford, A. W.; et al EP 533266 (1993)), K$_4$[Fe (CN)$_6$]-3H$_2$O (2.09 g, 4.94 mmol), Na$_2$CO$_3$ (1.05 g, 9.89 mmol), Pd(OAc)$_2$ (75 mg, 0.33 mmol), 1,4-diazabicyclo [2.2.2]octane (74 mg, 0.66 mmol), and DMA (20 mL) was maintained under $N_2$ atmosphere at 126-130° C. for 7.5 hr. Afterward, the mixture was cooled to room temperature, diluted with EtOAc, stirred for 20 min, and filtered through diatomaceous earth. The filtrate was concentrated under reduce pressure, and the residue (5.52 g) was stirred in a mixture of $Et_2O$ (5 mL) and hexanes (10 mL). Afterward, the solid was collected by filtration, and washed with $Et_2O$ to form the title compound (2.53 g). The mother liquor was concentrated under reduce pressure, and the residue was stirred in a mixture of $Et_2O$ (2 mL) and hexanes (4 mL) to form an additional amount of the compound (0.265 g) as a solid. Both batches were combined (2.80 g, 97%). $^1$H NMR (300 MHz, $CDCl_3$) δ ppm 2.59 (s, 3H), 3.03 (d, J=4.9 Hz, 3H), 6.17 (br s, 1H), 7.61 (dd, J=8.2, 1.5 Hz, 1H), 7.66 (d, J=8.0 Hz, 1H), 7.73 (s, 1H).

Part B. Preparation of
4-formyl-N,3-dimethylbenzamide

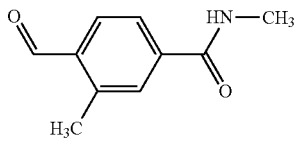

To a mixture of Raney Nickel 2800® (wet, 2.02 g) in 75% formic acid (40 mL) was added 4-cyano-N,3-dimethylbenzamide (1.94 g, 11.1 mmol). The resulting mixture was maintained at 100° C. for 3 hr, and then cooled, filtered through diatomaceous earth, and washed with EtOAc and MeOH. The filtrate was concentrated under reduced pressure, and the residue was purified by silica gel flash column chromatography (EtOAc 100%) to afford the title compound (1.94 g, 69%) as a solid.

Example 5

Preparation of N-ethyl-4-formyl-3-methylbenzamide

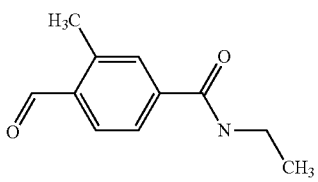

Ethanamine (0.041 g, 0.91 mmol) was added to 4-formyl-3-methylbenzoic acid (0.15 g, 0.91 mmol) in THF (10 ml) under $N_2$. The resulting suspension was stirred for 30 min then 4-(4,6-dimethoxy-1,3,5-triazin-2-yl)-4-methylmorpholin-4-ium (0.243 g, 1.01 mmol) was added and the suspension stirred for an additional 18 hr. The resulting mixture was concentrated under reduced pressure and the residue was dissolved in EtOAc (20 mL) and washed sequentially with water and brine. The organic layer was dried over $MgSO_4$, filtered, and concentrated under reduced pressure. The residue was purified by flash silica chromatography, eluting with a gradient 0-10% of MeOH in $CH_2Cl_2$ to yield N-ethyl-4-formyl-3-methylbenzamide (0.206 g) which contained ~10-20% of an impurity. The material was used without further purification. LCMS (ES+) m/z calc. for $C_{11}H_{14}NO_2$ $_{[M+H]}^+$ 192.23. found 192.27.

Example 6

Preparation of
2-fluoro-4-formyl-N,5-dimethylbenzamide

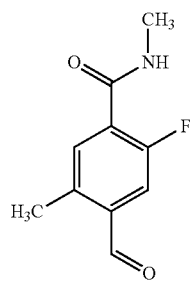

Part B. Part A. Preparation of
4-bromo-5-fluoro-2-methylbenzaldehyde

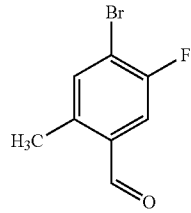

A solution of 5-bromo-4-fluoro-2-iodotoluene (5 g, 15.9 mmol) in Et2O (15 mL) was added dropwise to a solution of n-BuLi (2.5 M in hexane) (7.3 mL, 15.9 mmol) in Et2O (10 mL) at −100° C., during which the temperature of the mixture remained less than −95° C. After 15 min, anhydrous DMF (1.35 mL, 17.5 mmol) was added dropwise. The resulting mixture was warmed from −100° C. to room temperature over 2.5 hr while stirring. Afterward, 1 N HCl (50 mL) aqueous solution was added to adjust the pH to 1. The resulting mixture was extracted with EtOAc (2×50 mL). The combined organic layers were washed with brine, dried over MgSO4, filtered, and concentrated in vacuo. The residue was purified by silica gel flash chromatography (0-10% EtOAc in hexanes) to obtain 4-bromo-5-fluoro-2-methylbenzaldehyde (2.9 g, 84%) as a solid. 1H NMR (300 MHz, $CDCl_3$): δ ppm 2.63 (s, 3H), 7.50 (d, J=6.5 Hz, 1H), 7.54 (d, J=8.4 Hz, 1H), 10.20 (d, J=1.8 Hz, 1H).

Part B. Preparation of methyl
2-fluoro-4-formyl-5-methyl benzoate

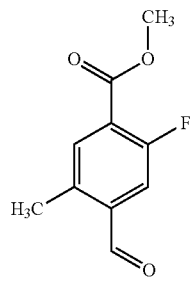

$Et_3N$ (3.5 ml, 25 mmol) was added to a solution of 4-bromo-5-fluoro-2-methylbenzaldehyde (1.08 g, 5.00 mmol) in DMF (20 mL) and MeOH (20 mL). CO was bubbled through the resulting solution for 10 min, and then $PdCl_2(Ph_3P)_2$ (0.35 g, 0.50 mmol) was added. Afterward, CO was bubbled through the solution for an additional 10 min, and then the mixture was heated at 70° C. for 18 hr under a CO atmosphere. The solution was cooled to room temperature, and concentrated under reduced pressure. The residue was diluted with EtOAc (100 mL), washed with a saturated aqueous solution of NaHCO₃ (30 mL), washed with brine (30 mL), dried over Na₂SO₄, filtered, and evaporated under reduced pressure. The residue was purified by silica gel flash column chromatography (10-20% EtOAc in hexanes) to form the title compound as a solid (0.403 g, 41%). $^1$H NMR (400 MHz, CDCl₃) δ ppm 2.67 (s, 3H), 3.97 (s, 3H), 7.57 (d, J=10.4 Hz, 1H), 7.83 (d, J=6.4 Hz, 1H), 10.29 (d, J=1.6 Hz, 1H).

Part C. Preparation of 2-fluoro-4-formyl-N,5-dimethylbenzamide

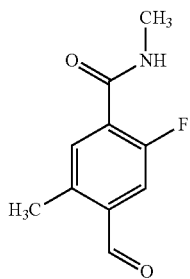

A mixture of methyl 2-fluoro-4-formyl-5-methylbenzoate (0.35 g, 1.65 mmol) in DMF (5 mL) and methanamine 40% wt in water (4.96 mL, 57.64 mmol) was stirred at 50° C. for 5 hr. The resulting mixture was concentrated under reduced pressure and the residue purified by flash chromatography on silica gel, eluting with a mixture of ethyl acetate (40-100%) and heptane to provide 2-fluoro-4-formyl-N,5-dimethylbenzamide (0.297 g, 92%) as solid. MS m/z (ESI) 195.91 [M+H]+.

Example 7

Preparation of (S)-tert-Butyl 2-ethynylmorpholine-4-carboxylate

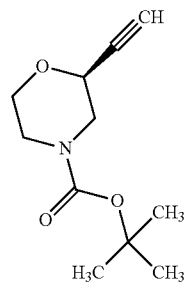

Part A. Preparation of tosyl azide

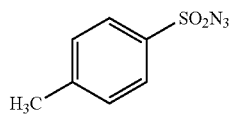

To a solution of sodium azide (37.5 g, 0.577 mol) in water (100 mL) was added ethanol (200 mL) at 20° C. To this solution was added a warm solution (40-45° C.) of tosyl chloride (100.0 g, 0.525 mol) in ethanol (500 mL) over 10 min. The resulting suspension was stirred at 20-25° C. for 2.5 hr. The ethanol was evaporated under reduced pressure and the residue was taken-up in water (600 mL). The oily product was separated and the aqueous layer was extracted with dichloromethane (150 mL). The combined organic phases were washed with water (2×100 mL), dried over sodium sulfate and evaporated under reduced pressure to give tosyl azide (98.0 g, 95% yield) as an oil. $^1$H NMR (400 MHz, CDCl₃) δ ppm 2.49 (s, 3H), 7.43 (d, J=8.30 Hz, 2H), 7.85 (d, J=8.30 Hz, 2H). Reference: *Org. Synth. Coll.* Vol. V, p 179.

Part B. Preparation of dimethyl (1-diazo-2-oxopropyl)phosphonate

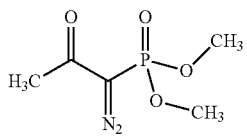

To a solution of dimethyl (2-oxopropyl)phosphonate (91.7 g, 0.552 mol) in acetonitrile (920 mL) was added potassium carbonate (91.6 g, 0.662 mol). The suspension was stirred at 40° C. for 1 hr. A solution of tosyl azide (114.4 g, 0.58 mol) in acetonitrile (460 mL) was then added drop wise over 45 min. The temperature was maintained between 18° C. and 24° C. during the addition. The resulting mixture was stirred for an additional 2 hr at 20-25° C. and was then filtered over diatomaceous earth. The filer cake was rinsed with acetonitrile (2×100 mL) and the combined filtrates were evaporated under reduced pressure. The residue was purified by chromatography (silica, eluting with a mixture of ethyl acetate/heptanes) to yield dimethyl (1-diazo-2-oxopropyl)phosphonate (90.5 g, 85%) as an oil. $^1$H NMR (400 MHz, CDCl₃) δ ppm 2.26 (s, 3H), 3.82 (s, 3H), 3.85 (s, 3H).

Part C. Preparation of tert-butyl (2R)-2-formylmorpholine-4-carboxylate

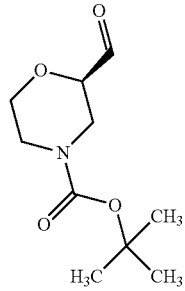

A solution of tert-butyl (2R)-2-(hydroxymethyl)morpholine-4-carboxylate (91.0 g, 0.418 mol), TEMPO (0.654 g, 0.004 mol), sodium bromide in water (0.5 M, 84 mL, 0.04 mol) and dichloromethane (910 mL) was cooled to 0-5° C. The pH of a solution of sodium hypochlorite (1.66 M, 308 mL, 0.52 mol) was adjusted to pH=9.3 the addition of sodium hydrogencarbonate (21 g, 0.21 mol), and the resulting solution was added drop wise over 30 min to the resulting mixture. The temperature was kept between 0 and 5° C. during the addition using an ice bath for cooling. The biphasic mixture was then stirred for an additional 30 min at 0-5° C. The temperature was adjusted to 20° C. and water (450 mL) was added. The phases were separated and the aqueous phase was extracted with dichloromethane (2×180 mL). The combined organic phases were washed with water (2×180 mL), then dried over sodium sulfate and evaporated under reduced pressure to give tert-butyl (2R)-2-formylmorpholine-4-carboxylate (63.02 g, 70%) as an orange viscous oil. ¹H NMR (400 MHz, CDCl₃) δ ppm 1.47 (s, 9H), 2.47-3.13 (m, 2H), 3.37-3.72 (m, 2H), 3.72-4.19 (m, 3H), 9.65 (s, 1H).

Part D. Preparation of (S)-tert-butyl 2-ethynylmorpholine-4-carboxylate

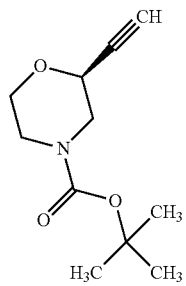

To a solution of dimethyl (1-diazo-2-oxopropyl)phosphonate (64.7 g, 0.337 mol) in a mixture of acetonitrile (526 mL) and methanol (105 mL) was added potassium carbonate (80.9 g, 0.585 mol). The suspension was stirred at 18-20° C. for 15 min. A solution of tert-butyl (2R)-2-formylmorpholine-4-carboxylate (63.0 g, 0.293 mol) in a mixture of acetonitrile (53 mL) and methanol (10 mL) was then added drop wise over 1 hr while maintaining the temperature between 18 and 23° C. The resulting mixture was stirred for 2 hr at 20° C. after the end of the addition and was then held overnight. The resulting suspension was filtered and the filtrate was evaporated under reduced pressure. The resulting oil was added slowly to water (950 mL), and the precipitate was collected by filtration, and the filter cake was washed with water (120 mL). The residue was purified by chromatography on silica gel (eluting with 10% ethyl acetate in heptanes) to give (S)-tert-butyl 2-ethynylmorpholine-4-carboxylate (45.25 g, 64% yield) as a solid. ¹H NMR (400 MHz, CDCl₃) δ ppm 1.47 (s, 9H), 2.49 (s, 1H), 3.20-3.32 (m, 2H), 3.49-3.61 (m, 2H), 3.70-3.90 (m, 1H), 3.90-3.99 (m, 1H), 4.21-4.28 (m, 1H); chiral HPLC (Chiracel OB-H 0.46×250 mm, hexanes 93%-ethanol 3%, 30° C., 0.6 mL/min, isocratic 30 min) 97.0% desired enantiomer.

Example 8

(R)-tert-Butyl 2-ethynylmorpholine-4-carboxylate

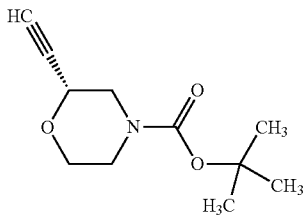

This compound was prepared using procedures similar to those described in Example 6. ¹H NMR (300 MHz, CDCl₃) δ ppm 1.45 (s, 9H), 2.47 (d, J=1.81 Hz, 1H), 3.17-3.37 (m, 2H), 3.45-3.62 (m, 2H), 3.70-3.87 (m, 1H), 3.88-3.98 (m, 1H), 4.20-4.26 (m, 1H); MS (ESI) m/z 112.17 [M-Boc+H]⁺.

Example 9

Preparation of (2R,5R)-tert-butyl 2-(hydroxymethyl)-5-methylmorpholine-4-carboxylate

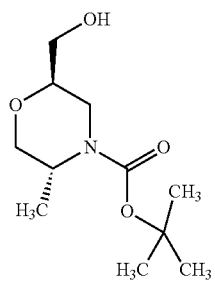 [SMILES: C[C@@H]1CO[C@@H](CO)CN1C(=O)OC(C)(C)C]

Part A. Preparation of (R)-2-(benzylamino)propan-1-ol

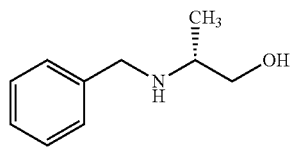

Benzaldehyde (10.0 g, 94.2 mmol) and (D)-alaninol (7.08 g, 94.2 mmol) were diluted in dichloroethane (100 mL). The resulting mixture was cooled to 0° C. Acetic acid (5.39 mL, 94.2 mmol) was added, followed 10 min later by NaBH(OAc)₃ (9.47 g, 44.7 mmol). After stirring for 18 hr at room temperature, aqueous Na₂CO₃ was added to adjust the pH to 9, and This compound was extracted with CH₂Cl₂. The combined organic phases were dried over MgSO₄ and concentrated under reduced pressure. The residue was purified by flash chromatography on silica gel, eluting with mixtures of 100% CH₂Cl₂ to 10/89/1 MeOH/CH₂Cl₂/NH₄OH to afford the title product (5.30 g, 34%) as an oil. ¹H NMR (300 MHz, CDCl₃) δ ppm 1.08 (d, J=6.3 Hz, 3H), 2.04-2.30 (m, 2H), 2.79-2.89 (m, 1H), 3.28 (dd, J=10.5, 6.9 Hz, 1H), 3.59 (dd, J=10.5, 4.2 Hz, 1H), 3.73 (d, J=12.9 Hz, 1H), 3.86 (d, J=12.9 Hz, 1H), 7.24-7.36 (m, 5H).

Part B. Preparation of (2R,5R)-4-benzyl-5-methylmorpholin-2-yl)methanol

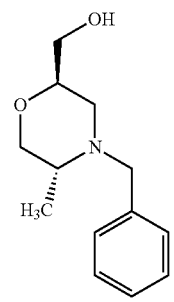 [SMILES: C[C@@H]1CO[C@@H](CO)CN1Cc1ccccc1]

(R)-2-(Benzylamino)propan-1-ol (5.30 g, 32.1 mmol) was dissolved in toluene (150 mL). (S)-Epichlorohydrin (3.76 mL, 48.1 mmol) was then added, followed by LiClO$_4$ (5.12 g, 48.1 mmol). The resulting mixture was stirred for 18 hr at room temperature. Sodium methoxide (which was prepared by adding NaOH (3.85 g, 96.2 mmol) to an ice-cooled solution of MeOH (60 mL) and stirring for 30 min) was added dropwise to the mixture. After stirring at room temperature for 18 hr, water was added. Toluene was removed under reduced pressure, and This compound was extracted with CH$_2$Cl$_2$. The organic phase was dried over MgSO$_4$, filtered, and concentrated under reduced pressure. The residue was purified by flash chromatography on silica gel, eluting with mixtures of Et$_2$O to 5% MeOH/Et$_2$O to afford the title compound (5.13 g, 72%) as an oil. $^1$H NMR (300 MHz, CDCl$_3$) δ ppm 1.08 (d, J=6.0 Hz, 3H), 1.90-2.03 (m, 2H), 2.36-2.44 (m, 1H), 2.57 (dd, J=11.7, 2.1 Hz, 1H), 3.05 (d, J=13.2 Hz, 1H), 3.31-3.64 (m, 4H), 3.77 (dd, J=11.7, 3.3 Hz, 1H), 4.14 (d, J=13.2 Hz, 1H), 7.23-7.34 (m, 5H).

Part C. Preparation of (2R,5R)-tert-butyl 2-(hydroxymethyl)-5-methylmorpholine-4-carboxylate

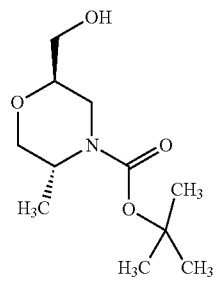 [SMILES: C[C@@H]1CO[C@@H](CO)CN1C(=O)OC(C)(C)C]

(2R,5R)-4-Benzyl-5-methylmorpholin-2-yl)methanol (5.10 g, 23.0 mmol) was dissolved in MeOH, and N$_2$ was bubbled through the resulting solution. Boc$_2$O (5.03 g, 23.0 mmol) was then added, followed by Pd(OH)$_2$ (2.55 g). After stirring for 18 hr under 1.01 bar H$_2$, the mixture was diluted with CH$_2$Cl$_2$ and filtered through a pad of diatomaceous earth. The filtrate was concentrated under reduced pressure, and the residue was purified by flash chromatography on silica gel, eluting with mixtures of 70% to 80% of EtOAc and hexanes to produce the title compound (3.20 g, 60%) as an oil. $^1$H NMR (300 MHz, DMSO-d$_6$) δ ppm 1.12 (d, J=6.3 Hz, 3H), 1.39 (s, 9H), 3.19-3.58 (m, 5H), 3.60-3.74 (m, 2H), 3.81-3.90 (m, 1H), 4.69 (dd, J=6.0, 4.5 Hz, 1H). MS (ESI) m/z 132.3 [M+H-Boc]$^+$.

Example 10

Preparation of (2R,5S)-tert-butyl 2-(hydroxymethyl)-5-methylmorpholine-4-carboxylate

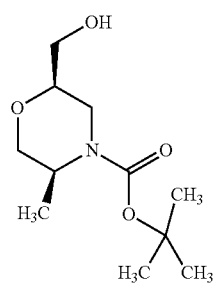 [SMILES: C[C@H]1CO[C@@H](CO)CN1C(=O)OC(C)(C)C]

This compound was prepared using procedures similar to those described in Example 8. $^1$H NMR (300 MHz, CDCl$_3$) δ ppm 1.22 (d, J=6.86 Hz, 3H), 1.46 (s, 9H), 1.89-1.95 (m, 1H), 2.83-3.00 (m, 1H), 3.38-4.04 (m, 7H).

Example 11 tert-butyl 3-ethynylpyrrolidine-1-carboxylate

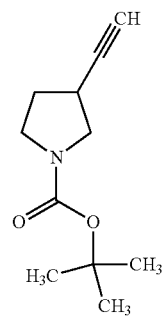

This compound was synthesized using procedures similar to those described in Example 6, part D and starting from commercially available starting material. $^1$H NMR (300 MHz, CDCl$_3$) δ ppm 1.45 (s, 9H), 1.85-2.00 (m, 1H), 2.08-2.20 (m, 2H), 2.87-3.00 (m, 1H), 3.21-3.38 (m, 2H), 3.40-3.69 (m, 2H); MS (ESI) m/z 96.15 [M-Boc+H]$^+$.

Example 12 tert-butyl 4-ethynyl-2-methylpyrrolidine-1-carboxylate

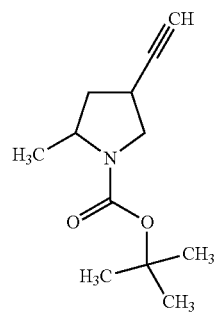

Part A. Preparation of 1-benzyl-5-methylpyrrolidin-2-one

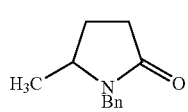

Sodium hydride (60% suspension in mineral oil) (2.54 g, 63.6 mmol) was added to a solution of 5-methylpyrrolidin-2-one (4.2 g, 42.4 mmol) in N,N-dimethylformamide (27 mL) at 0° C. Benzyl bromide (6.05 mL, 50.8 mmol) was then added and the resulting mixture was stirred for 16 h, while letting the temperature rise from 0° C. to room temperature. A saturated aqueous solution of ammonium chloride (50 mL) was then slowly added and the product was extracted with ethyl acetate (3×50 mL). The combined organic layers were washed with a 5% aqueous solution of sodium hydrogen carbonate (100 mL), dried with magnesium sulfate, filtered and concentrated under reduced pressure. The residue was purified by chromatography on a 100 g silica gel cartridge using a gradient of 5 to 75% of EtOAc in hexanes to provide 1-benzyl-5-methylpyrrolidin-2-one (6.88 g, 86%) as an oil. $^1$H NMR (300 MHz, CDCl$_3$): δ ppm 1.16 (d, J=6.25 Hz, 3H), 1.53-1.64 (m, 1H), 2.04-2.21 (m, 1H), 2.34-2.56 (m, 2H), 3.46-3.58 (m, 1H), 3.98 (d, J=15.02 Hz, 1H), 4.97 (d, J=15.02 Hz, 1H), 7.21-7.35 (m, 5H).

Part B. Preparation of methyl 1-benzyl-5-methyl-2-oxopyrrolidine-3-carboxylate

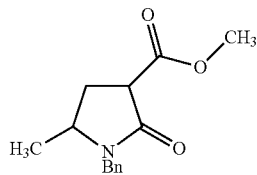

n-Butyllithium (2.5 M in hexanes) (29 mL, 72.7 mmol) was slowly added to a solution of diisopropylamine (10.7 mL, 76.3 mmol) in tetrahydrofuran (50 mL) cooled using an ice bath so to keep the internal temperature below 10° C. The resulting mixture was cooled to −78° C. and a solution of 1-benzyl-5-methylpyrrolidin-2-one (6.88 g, 36.4 mmol) in tetrahydrofuran (46 mL) was added at such a rate as to maintain the internal temperature below −65° C. After the end of the addition, the mixture was stirred at −78° C. 0.5 hr. Dimethyl carbonate (6.13 mL, 72.7 mmol) was then added, and the mixture was stirred at −78° C. 0.25 hr. The cold bath was then removed, and the mixture was gradually warmed to room temperature and stirred at this temperature 16 hr. A 1 N aqueous solution of hydrochloric acid (100 mL) was added and the product was extracted with ethyl acetate (3×100 mL). The combined organic layers were washed with water (150 mL) and then brine (150 mL). The organic layer was dried with magnesium sulfate, filtered and concentrated under reduced pressure. The crude residue was purified by silica gel flash using a gradient of 10 to 60% of EtOAc in hexanes to furnish methyl 1-benzyl-5-methyl-2-oxopyrrolidine-3-carboxylate (6.85 g, 76%) as an oil and as a mixture of diastereoisomers. $^1$H NMR (300 MHz, CDCl$_3$): δ ppm 1.16 and 1.25 (2 d, J=6.37 and 6.25 Hz, 3H), 1.79-1.89 (m, 0.5H), 1.97-2.08 (m, 0.5H), 2.34-2.54 (m, 1H), 3.45-3.74 (m, 2H), 3.79 and 3.81 (2 s, 3H), 4.01 (dd, J=14.99, 9.43 Hz, 1H), 4.99 (dd, J=15.01, 11.63 Hz, 1H), 7.21-7.36 (m, 5H).

Part C. Preparation of (1-benzyl-5-methylpyrrolidin-3-yl)methanol

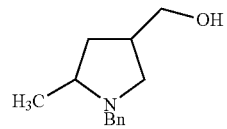

Lithium aluminum hydride (3.89 g, 0.10 mol) was carefully added to anhydrous tetrahydrofuran (100 mL) at 0° C.

A solution of methyl 1-benzyl-5-methyl-2-oxopyrrolidine-3-carboxylate (6.85 g, 27.7 mmol) in anhydrous tetrahydrofuran (39 mL) was then added. The resulting mixture was stirred at room temperature 16 hr, then was cooled to 0° C., and water (4 mL) was very slowly added, followed by a 15% aqueous solution of sodium hydroxide (4 mL) and again water (12 mL). The resulting suspension was stirred at 0° C. 1 hr and then magnesium sulfate was added. The suspension was stirred at 0° C. 0.25 hr and filtered on a pad of diatomaceous earth. The filter cake was washed with ethyl acetate and the filtrate was concentrated under reduced pressure to provide (1-benzyl-5-methylpyrrolidin-3-yl) methanol (5.53 g, 97%) as an oil. The resulting product used in the next step without further purification.

Part D. Preparation of (5-methylpyrrolidin-3-yl)methanol

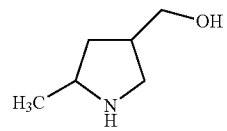

A solution of (1-benzyl-5-methylpyrrolidin-3-yl)methanol (5.53 g, 26.9 mmol) in ethanol (192 mL) was put under vacuum and backfilled with nitrogen three times. Palladium hydroxide on carbon (20 wt. %, 50% wet) (1.89 g) was added. Hydrogen was bubbled into the suspension 0.25 hr. The resulting mixture was stirred under 1.01 bar of hydrogen 16 hr at room temperature. The mixture was then filtered on a pad of diatomaceous earth. The filter cake was washed with ethanol and the filtrate was concentrated under reduced pressure to provide (5-methylpyrrolidin-3-yl)methanol (3.16 g, quant., mixture of diastereoisomers) as an oil. $^1$H NMR (300 MHz, CDCl$_3$): δ ppm 0.96-1.06 (m, 0.5H), 1.14 and 1.18 (2 d, J=6.35 and 6.19 Hz, 3H), 1.37-1.47 (m, 0.5H), 1.65-1.74 (m, 0.5H), 2.00-2.15 (m, 3H), 2.27-2.43 (m, 1H), 2.63 (dd, J=10.90, 6.50 Hz, 0.5H), 2.86-3.00 (m, 1H), 3.06-3.24 (m, 1H), 3.48-3.66 (m, 2H).

Part E. tert-butyl 4-(hydroxymethyl)-2-methylpyrrolidine-1-carboxylate

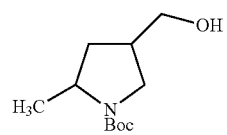

Potassium carbonate (19 g, 0.14 mol) and di-tert-butyl dicarbonate (5.99 g, 27.4 mmol) were added to a solution of (5-methylpyrrolidin-3-yl)methanol (3.16 g, 27.4 mmol) in tetrahydrofuran (30 mL) and water (30 mL) at 0° C. The resulting mixture was stirred at room temperature 16 hr and then water (50 mL) was added. The product was extracted with ethyl acetate (3×50 mL). The combined organic layers were washed with brine (100 mL), dried over magnesium sulfate, filtered and concentrated under reduced pressure. The residue was purified by chromatography on a 100 g silica gel cartridge using a gradient of 10 to 70% of EtOAc in hexanes to furnish tert-butyl 4-(hydroxymethyl)-2-methylpyrrolidine-1-carboxylate (4.38 g, 74%, mixture of diastereoisomers). ¹H NMR (300 MHz, CDCl₃): δ ppm 1.14-1.28 (m, 3H), 1.30-1.70 (m, 2H), 1.45 (s, 9H), 1.71-1.88 (m, 0.5H), 2.17-2.35 (m, 1H), 2.42-2.57 (m, 0.5H), 3.00 (dd, J=10.97, 8.94 Hz, 0.5H), 3.05-3.20 (m, 0.5H), 3.50 (dd, J=10.98, 7.64 Hz, 0.5H), 3.55-4.05 (m, 3.5H).

Part F. tert-butyl 4-formyl-2-methylpyrrolidine-1-carboxylate

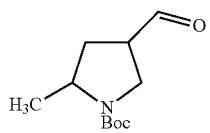

Dess-Martin periodinane (4.23 g, 10.2 mmol) was added to a suspension of tert-butyl 4-(hydroxymethyl)-2-methyl-pyrrolidine-1-carboxylate (2 g, 9.29 mmol) and sodium hydrogencarbonate (1.17 g, 13.9 mmol) in dichloromethane (23 mL) at 0° C. The resulting mixture was stirred at room temperature 2 hr and then a 10% aqueous solution of sodium thiosulfate (50 mL) and a 5% aqueous solution of sodium hydrogencarbonate (25 mL) were added. The resulting mixture was stirred at room temperature 16 hr. The phases were separated and the aqueous layer was extracted with dichloromethane (1×25 mL). The combined organic layers were dried with magnesium sulfate, filtered and concentrated under reduced pressure to provide tert-butyl 4-formyl-2-methylpyrrolidine-1-carboxylate (2.09 g, quant., mixture of diastereoisomers) as an oil. ¹H NMR (300 MHz, CDCl₃): δ ppm 1.13-1.22 (m, 3H), 1.46 (s, 9H), 1.71-1.81 (m, 0.5H), 1.86-1.96 (m, 0.5H), 2.15-2.40 (m, 1H), 2.88-2.98 (m, 0.5H), 3.00-3.13 (m, 0.5H), 3.48-3.58 (m, 0.5H), 3.60-3.75 (m, 1.5H), 3.85-4.05 (m, 1H) 9.65 and 9.73 (2 d, J=2.14 and 1.51 Hz, 1H).

Part H. tert-butyl 4-ethynyl-2-methylpyrrolidine-1-carboxylate

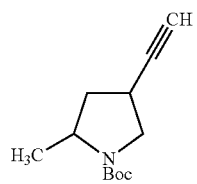

Potassium carbonate (2.6 g, 18.8 mmol) was added to a solution of tert-butyl 4-formyl-2-methylpyrrolidine-1-carboxylate (2.0 g, 9.38 mol) in acetonitrile (25 mL) and methanol (5 mL). Dimethyl (1-diazo-2-oxopropyl)phosphonate (2.16 g, 11.3 mmol) was then added dropwise. The suspension was stirred at room temperature for 16 hr and then was concentrated under reduced pressure. A 5% aqueous solution of sodium hydrogencarbonate (25 mL) was added to the crude residue. The product was extracted with ethyl acetate (3×25 mL). The combined organic phases were dried with magnesium sulfate, filtered and concentrated under reduced pressure. The crude material was purified by silica gel chromatography using a gradient of 0 to 30% of EtOAc in heptanes to yield tert-butyl 4-ethynyl-2-methyl-pyrrolidine-1-carboxylate (1.31 g, 67%, mixture of diastereoisomers) as an oil. ¹H NMR (300 MHz, CDCl₃): δ ppm 1.16 (d, J=6.21 Hz, 1.5H), 1.31 (br s, 1.5H), 1.46 (s, 9H), 1.60-1.72 (m, 0.5H), 1.85 (ddd, J=12.25, 6.41, 2.53 Hz, 0.5H), 2.03-2.18 (m, 0.5H), 2.10 (dd, J=5.13, 2.38 Hz, 1H), 2.36-2.45 (m, 0.5H), 2.76-2.88 (m, 0.5H), 2.96-3.08 (m, 0.5H), 3.24 (dd, J=10.85, 8.70 Hz, 0.5H), 3.28-3.40 (m, 0.5H), 3.59-3.67 (m, 0.5H), 3.74-4.06 (m, 1.5H); MS (ESI) m/z calcd for C₇H₁₂N 110.10 [M-Boc+H]⁺. found 110.11.

Example 13

(2S,5R)-tert-butyl 2-ethynyl-5-methylmorpholine-4-carboxylate

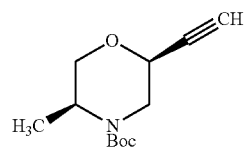 [SMILES: C#C[C@H]1CN(C(=O)OC(C)(C)C)[C@@H](C)CO1]

This compound was prepared using procedures similar to those described in Example 6, part D. ¹H NMR (300 MHz, CDCl₃) δ ppm 1.24 (d, J=6.64 Hz, 3H), 1.46 (s, 9H), 2.50 (s, 1H), 3.09 (t, J=11.82 Hz, 1H), 3.66 (q, J=12.23 Hz, 2H), 3.85-3.99 (m, 1H), 4.08 (d, J=7.82 Hz, 2H); MS (ESI) m/z 126.19 [M-Boc+H]⁺.

Example 14

(2S,5S)-tert-butyl 2-ethynyl-5-methylmorpholine-4-carboxylate

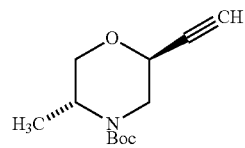 [SMILES: C#C[C@H]1CN(C(=O)OC(C)(C)C)[C@H](C)CO1]

This compound was prepared using procedures similar to those described in Example 6, part D. ¹H NMR (300 MHz, CDCl₃) δ ppm 1.24 (d, J=7.01 Hz, 3H), 1.47 (s, 9H), 2.42 (s, 1H), 3.29-3.46 (m, 2H), 3.88 (d, J=13.21 Hz, 1H), 4.11-4.23 (m, 2H), 4.55 (s, 1H); MS (ESI) m/z 126.21 [M-Boc+H]+.

Example 15

Preparation of (S)-methyl-2-((2-(2,6-difluoro-4-(methylcarbamoyl)phenyl)-7-methylimidazo[1,2-a]pyridin-3-yl)methyl)morpholine-4-carboxylate

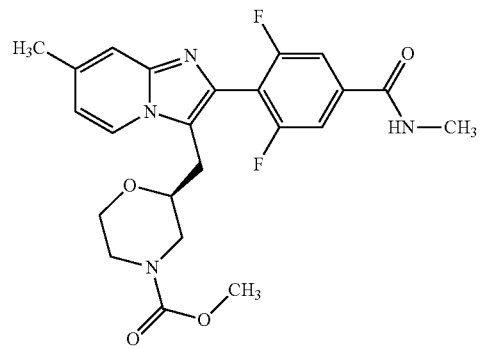

Part A. Preparation of (S)-tert-butyl 2-((2-(2,6-difluoro-4-(methylcarbamoyl)phenyl)-7-methylimidazo[1,2-a]pyridin-3-yl)methyl)morpholine-4-carboxylate. Also, illustrates General Cyclization Conditions 1

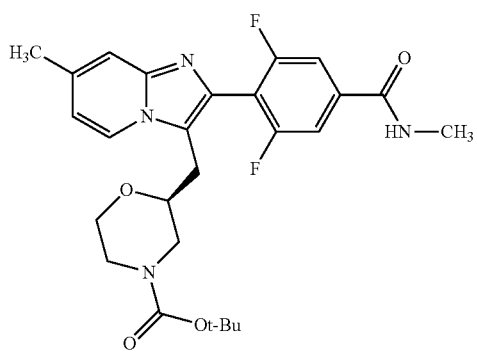

A mixture of 4-methylpyridin-2-amine (5.41 g, 0.050 mol), 3,5-difluoro-4-formyl-N-methylbenzamide (9.96 g, 0.050 mol), (S)-tert-butyl 2-ethynylmorpholine-4-carboxylate (10.57 g, 0.050 mol), copper(I) chloride (1.49 g, 0.015 mol), bis(trifluoromethylsulfonyloxy)copper (5.42 g, 0.015 mol) and toluene (120 mL) was charged to a 250 mL jacketed reactor under $N_2$. Heating was applied and the temperature reached 85° C. in 5 min. N,N-dimethylacetamide (1.0 mL) was then added and the resulting mixture was stirred at 85° C. for 5 hr. The resulting mixture was then cooled to 20° C. and held overnight at this temperature. The toluene layer was separated by decantation from a solid residue, and then was concentrated under reduced pressure. The resulting residue was mixed with the solid residue isolated from decantation, and the combined solids were dissolved dichloromethane (300 mL). A solution of sodium sulfide in water (18% w/w) was added to the organic solution and the mixture was stirred for 15 min. The mixture was then filtered over a pad of diatomaceous earth and the cake was washed with dichloromethane (2×160 mL). The layers were separated and the aqueous phase was extracted with dichloromethane (100 mL). The combined organic layers were concentrated under reduced pressure. The residue was dissolved with ethyl acetate (500 mL), combined with silica gel (50 g), stirred for 30 min and then filtered over a pad of diatomaceous earth. The solution was concentrated under reduced pressure and the residue dissolved with dichloromethane (300 mL). Silica gel (32.5 g) was added and the mixture was concentrated to dryness under reduced pressure. The pre-absorbed crude material was packed on a dry silica column (80 g) and was eluted with ethyl acetate-heptane 50-50 v/v to give 13.7 g of a residue material which was then triturated in a mixture of ethyl acetate-heptane 30-70 v/v. The solid was collected by filtration, the filter cake washed with ethyl acetate-heptane 30-70 v/v, and the resulting solid dried mechanical vacuum to yield (S)-tert-butyl 2-((2-(2,6-difluoro-4-(methylcarbamoyl)phenyl)-7-methylimidazo[1,2-a]pyridin-3-yl)methyl)morpholine-4-carboxylate as a white solid (11.0 g, 44%). $^1$H NMR (400 MHz, DMSO-$d_6$) δ ppm 1.35 (s, 9H), 2.36-2.81 (m, 5H), 2.85 (d, J=4.46 Hz, 3H), 3.06 (d, J=6.12 Hz, 2H), 3.24 (t, J=10.93 Hz, 1H), 3.43-3.50 (m, 1H), 3.56-3.72 (m, 3H), 6.85 (d, J=6.84 Hz, 1H), 7.37 (s, 1H), 7.68 (d, J=7.89 Hz, 2H), 8.44 (d, J=6.84 Hz, 1H), 8.72 (br. s, 1H); MS (ESI) m/z 501.16 [M+H]$^+$. For further discussion related to this method, see Chernyak, N, et al., "General and Efficient Copper-Catalyzed Three-Component Coupling Reaction towards Imidazoheterocycles. One-Pot Synthesis of Alpidem and Zolpidem," *Angewandte Chemie*, vol. 49 (15), pp. 2743-2746 (Int'l Ed. 2010).

Part B. Preparation of (S)-methyl-2-((2-(2,6-difluoro-4-(methylcarbamoyl)phenyl)-7-methylimidazo[1,2-a]pyridin-3-yl)methyl)morpholine-4-carboxylate

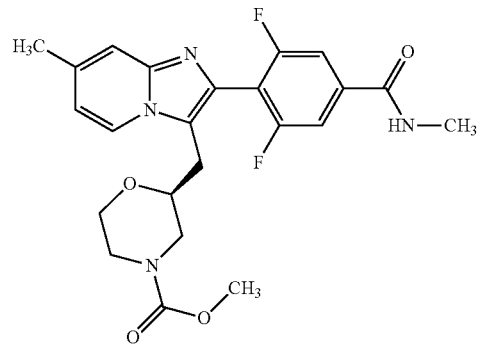

To a solution (S)-tert-butyl-2-((2-(2,6-difluoro-4-(methylcarbamoyl)phenyl)-7-methylimidazo[1,2-a]pyridin-3-yl)methyl)morpholine-4-carboxylate (41.0 g, 0.082 mol) in methanol (330 mL) was added a solution of 3 N hydrogen chloride in methanol (273 mL, 0.819 mol) over 15 min at 20-25° C. The resulting mixture was heated to 40-45° C. and stirred for 1 hr. The resulting mixture was then cooled to 20° C. and concentrated under reduced pressure. The residue was dissolved with dichloromethane (410 mL), and N,N-diisopropylethylamine (26.5 g, 0.205 mol) was added. Methyl chloroformate (9.3 g, 0.098 mol) was then added drop wise at 20° C. followed by additional N,N-diisopropylethylamine (5.3 g, 0.040 mol). After stirring for 16 h, the organic layer was washed with water (100 mL). The aqueous phase was extracted with dichloromethane (50 mL), the combined organic phases were then washed with aqueous potassium hydrogencarbonate 20% w/w and concentrated under reduced pressure. The residue was recrystallized from ethyl acetate (860 mL) with a hot filtration step to remove insoluble material. The precipitate was collected by filtration and the cake was rinsed with ethyl acetate (2×40 mL) and then dried under mechanical vacuum at 50° C. to yield the title compound as an ethyl acetate solvate (white solid, 31.8 g). Ethyl acetate was removed as follows: the material was dissolved in water (320 mL) by gradual addition of hydrochloric acid 3 N (22.5 mL) and the resulting solution was filtered over a filter paper to remove insoluble material. Ethyl acetate was removed by evaporation under reduced pressure until about 75 mL of mixed ethyl acetate-water had been collected in the receiver. Water (75 mL) was added to replace the volume distilled. The solution was transferred to a round bottom flask equipped with mechanical stirring and the pH was gradually adjusted to 8.5 by a slow addition of aqueous potassium hydrogencarbonate 20% w/w (135 mL). The resulting suspension was stirred overnight at 20-25° C. The product was collected by filtration and the cake was washed with water (30 mL) and then dried in a vacuum oven to yield (S)-methyl-2-((2-(2,6-difluoro-4-(methylcarbamoyl)phenyl)-7-methylimidazo[1,2-a]pyridin-3-yl)methyl)morpholine-4-carboxylate (25.25 g, 67%) as a solid. $^1$H NMR (400 MHz, DMSO-d$_6$) δ ppm 2.39 (s, 3H), 2.85 (s, 4H), 3.07 (br s, 2H), 3.25 (m, 1H), 3.45-3.79 (m, 8H), 6.85 (br s, 1H), 7.37 (br s, 1H), 7.68 (br s, 2H), 8.45 (br s, 1H), 8.72 (br s, 1H); HRMS m/z calcd for $C_{23}H_{25}F_2N_4O_4$ 459.1838 [M+H]$^+$. found 459.1844.

Example 15B

Preparation of (R)-tert-butyl 2-((7-methyl-2-(2-methyl-4-(methylcarbamoyl)phenyl)imidazo[1,2-a]pyridin-3-yl)methyl)morpholine-4-carboxylate. Illustrates General Cyclization Conditions 2

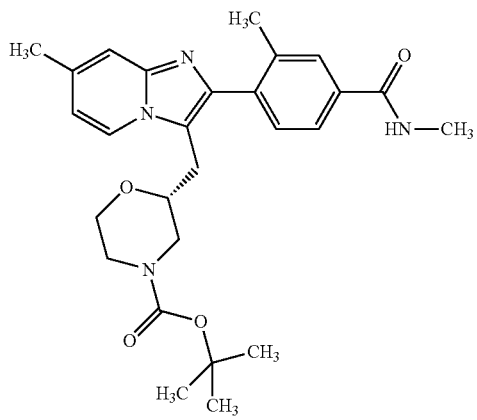

A 0.5-2.0 mL microwave vial was charged with 4-methylpyridin-2-amine (1 eq.), 4-formyl-N,3-dimethylbenzamide (1.05 eq.), (R)-tert-butyl 2-ethynylmorpholine-4-carboxylate (1 eq.), copper(I) chloride (0.05 eq.), bis(trifluoromethylsulfonyloxy)copper (0.05) and toluene (4 mL). The resulting mixture was purged for 5 min with N$_2$. The resulting mixture was stirred at 140° C. under microwave irradiation for 45 min. The resulting mixture was dissolved in EtOAc and was filtered using fluted filter paper. The filtrate was concentrated under reduced pressure and the residue was purified by silica gel flash chromatography eluting with 2% to 20% ethyl acetate in methanol to provide (R)-tert-butyl 2-((7-methyl-2-(2-methyl-4-(methylcarbamoyl)phenyl)imidazo[1,2-a]pyridin-3-yl)methyl)morpholine-4-carboxylate (30.3%) as an oil. $^1$H NMR (400 MHz, CD$_3$OD) δ ppm 1.32-1.48 (m, 10H), 2.24 (s, 3H), 2.39 (s, 3H), 2.46-2.59 (m, 1H), 2.70-2.91 (m, 1H), 2.95 (s, 3H), 2.98-3.10 (m, 2H), 3.43-3.58 (m, 1H), 3.60-3.79 (m, 3H), 6.88 (d, J=7.03 Hz, 1H), 7.04 (br. s., 1H), 7.40 (d, J=7.42 Hz, 1H), 7.70 (d, J=7.42 Hz, 1H), 7.79 (s, 1H), 8.37 (d, J=5.47 Hz, 1H). MS (ESI) m/z 479.18 [M+H]$^+$.

Example 15C

Preparation of (S)-tert-butyl 2-((7-methyl-2-(2-methyl-4-(methylcarbamoyl)phenyl)imidazo[1,2-a]pyridin-3-yl)methyl)morpholine-4-carboxylate. Also illustrates General Cyclization Conditions 3

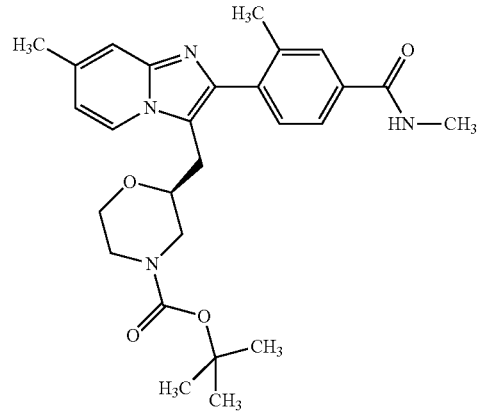

A mixture of 4-methylpyridin-2-amine (1 eq.), copper(I) chloride (0.05 eq.), bis(trifluoromethylsulfonyloxy)copper (0.05 eq.) and 4-formyl-N,3-dimethylbenzamide (1 eq.) under N$_2$ was stirred at room temperature for 5 min. Degassed toluene (2 mL), (S)-tert-butyl 2-ethynylmorpholine-4-carboxylate (1.5 eq.) were added, and the resulting mixture was stirred at 120° C. for 17 hr. The resulting mixture was cooled to rt, concentrated under reduced pressure and the residue was purified by silica gel flash chromatography eluting with 1% to 10% methanol in ethyl acetate to provide (S)-tert-butyl 2-((7-methyl-2-(2-methyl-4-(methylcarbamoyl)phenyl)imidazo[1,2-a]pyridin-3-yl)methyl)morpholine-4-carboxylate (174 mg, 56.2%) as an oil. MS (ESI) m/z 479.58 [M+H]$^+$.

Example 15D

Preparation of (R)-tert-butyl 2-((2-(2,6-difluoro-4-(methylcarbamoyl)phenyl)-7-methylimidazo[1,2-a]pyridin-3-yl)methyl)morpholine-4-carboxylate. Also illustrates General Cyclization Conditions 4

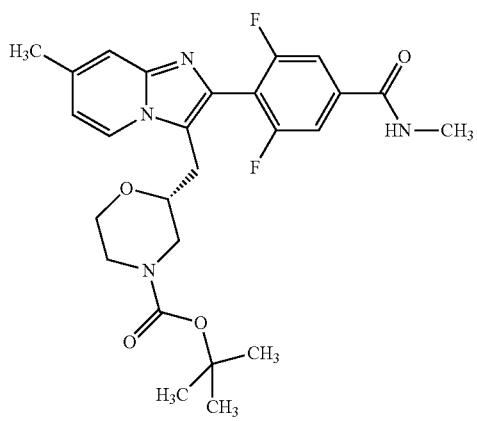

A mixture of 4-methylpyridin-2-amine (1 eq.), 3,5-difluoro-4-formyl-N-methylbenzamide (1 eq.), (R)-tert-butyl 2-ethynylmorpholine-4-carboxylate (1 eq.), copper(I) chloride (0.03 eq.) and bis(trifluoromethylsulfonyloxy)copper (0.03 eq.) under $N_2$ in toluene (4 mL) and DMA (0.1 mL) was stirred at room temperature for 5 min. The resulting mixture was stirred at 85° C. for 18 hr. The resulting mixture was cooled to rt, concentrated under reduced pressure and the residue was purified by silica gel flash chromatography eluting with 2% to 10% methanol in ethyl acetate to provide (R)-tert-butyl 2-((2-(2,6-difluoro-4-(methylcarbamoyl)phenyl)-7-methylimidazo[1,2-a]pyridin-3-yl)methyl)morpholine-4-carboxylate (65.5%) as an oil. MS (ESI) m/z 501.77 $[M+H]^+$.

Example 15E

Preparation of (2S,5S)-tert-Butyl 5-methyl-2-((7-methyl-2-(2-methyl-4-(methylcarbamoyl)phenyl)imidazo[1,2-a]pyridin-3-yl)methyl)morpholine-4-carboxylate. Also illustrates General Cyclization Conditions 5

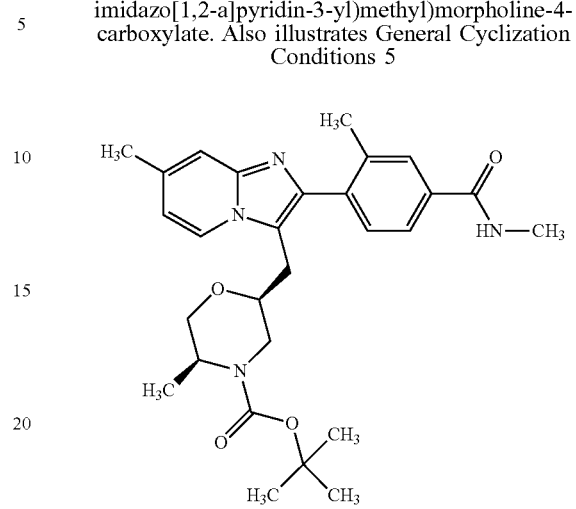

4-Methylpyridin-2-amine (0.14 g, 1.26 mmol), 4-formyl-N,3-dimethylbenzamide (0.22 g, 1.26 mmol), (2S,5S)-tert-butyl 2-ethynyl-5-methylmorpholine-4-carboxylate (0.28 g, 1.26 mmol), and copper(I) chloride (62 mg, 0.63 mmol) were added to a round-bottom flask. Toluene (10 mL) and N,N-dimethylacetamide (5 drops) were then added. The flask was put under vacuum and then back-filled with $N_2$ three times. The resulting mixture was stirred at 90° C. for 16 hr, and then cooled to room temperature. Afterward, ethanol and silica gel were added to the mixture, which was then concentrated under reduced pressure. The residue was purified by flash-chromatography on a 50 g silica gel cartridge eluting using 50% to 100% ethyl acetate in hexanes as eluent, followed by 0% to 20% methanol in ethyl acetate, to provide (2S,5S)-tert-butyl 5-methyl-2-((7-methyl-2-(2-methyl-4-(methylcarbamoyl)phenyl)imidazo[1,2-a]pyridin-3-yl)methyl)morpholine-4-carboxylate (0.37 g, 60%) as an oil which was used without further purification.

The compounds of Examples 16-44 in the following Table 1 were prepared using processes similar to those described in Examples 15, 15B, 15C, 15D, and 15E using corresponding starting materials and one of the general cyclization conditions as indicated below.

TABLE 1

EXAMPLES 18-46

| Ex | Compound Structure | Cyclization Procedure | LCMC (RT, m/z)[1] | $^1$H NMR |
|---|---|---|---|---|
| 16 | 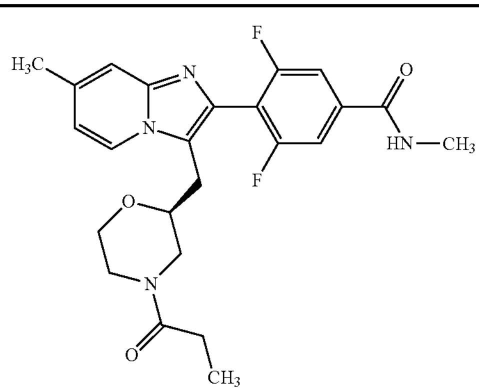 | 1 | HRMS (ESI) m/z calcd for $C_{24}H_{26}F_2N_4O_3$ 457.2046 $[M + H]^+$, found 457.2042. | $^1$H NMR (400 MHz, CD3OD) δ ppm 1.04 (dt, J = 9.77, 7.42 Hz, 3 H), 2.20-2.43 (m, 2 H), 2.45 (s, 3 H), 2.60-2.90 (m, 1H), 2.95 (s, 3 H), 3.05-3.18 (m, 3 H), 3.25-3.45 (m, 2H), 3.47-3.64 (m, 1 H), 3.70 (t, J = 12.11 Hz, 1 H), 3.75-3.85 (m, 1 H), 4.18-4.31 (m, 1 H), 6.87 (td, J = 4.69, 2.34 Hz, 1 H), 7.33 (s, 1 H), 7.59 (dd, J = 8.20, 5.86 Hz, 2 H), 8.36-8.46 (m, 1 H). |

TABLE 1-continued

EXAMPLES 18-46

| Ex | Compound Structure | Cyclization Procedure | LCMC (RT, m/z)[1] | $^1$H NMR |
|---|---|---|---|---|
| 17 | 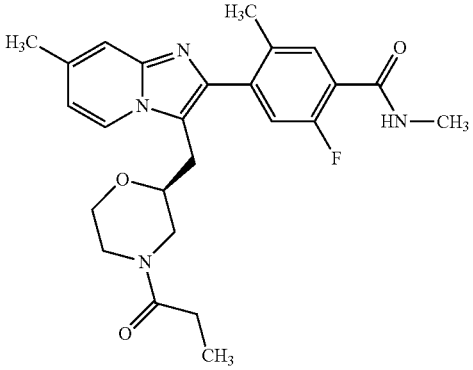 | 2 | HRMS m/z calcd for $C_{25}H_{30}FN_4O_3$ 453.2301 [M + H]+, found 453.2296. | $^1$H NMR (400 MHz, DMSO-$d_6$) δ ppm 0.88-0.99 (m, 3 H), 2.12-2.35 (m, 5 H), 2.38 (s, 3 H), 2.53-2.64 (m, 1 H), 2.79 (d, J = 4.30 Hz, 3 H), 2.92-3.13 (m, 2 H), 3.14-3.30 (m, 2 H), 3.40-3.65 (m, 2 H), 3.67-3.84 (m, 1 H), 4.02-4.21 (m, 1 H), 6.77-6.88 (m, 1 H), 7.23-7.40 (m, 2 H), 7.54 (d, J = 7.42 Hz, 1 H), 8.27 (br. s, 1 H), 8.43 (dd, J = 17.38, 7.23 Hz, 1 H). |
| 18 | 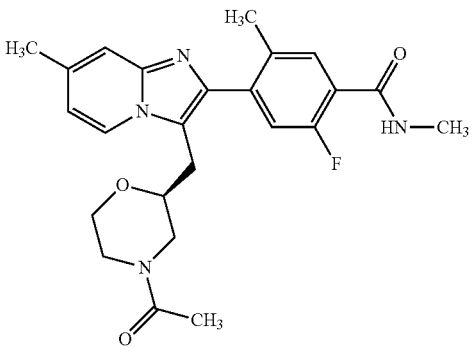 | 2 | HRMS m/z calcd for $C_{24}H_{28}FN_4O_3$ 439.214 [M + H]+, found 439.2143. | $^1$H NMR (400 MHz, CD$_3$OD) δ ppm 2.05 (2 s, 3 H), 2.25 (s, 3 H), 2.41 (dd, J = 12.89, 10.94 Hz, 1 H), 2.46 (s, 3 H), 2.70 (d, J = 3.52 Hz, 1 H), 3.03-3.10 (m, 3 H), 3.12-3.24 (m, 2 H), 3.34-3.45 (m, 1 H), 3.48-3.61 (m, 2 H), 3.62-3.86 (m, 1 H), 4.13-4.32 (m, 1 H), 6.87 (dt, J = 7.13, 1.90 Hz, 1 H), 7.16-7.29 (m, 1H), 7.29-7.36 (m, 1 H), 7.70 (dd, J = 7.62, 3.71 Hz, 1 H), 8.37 (dd, J = 15.23, 7.03 Hz, 1 H). |
| 19 | 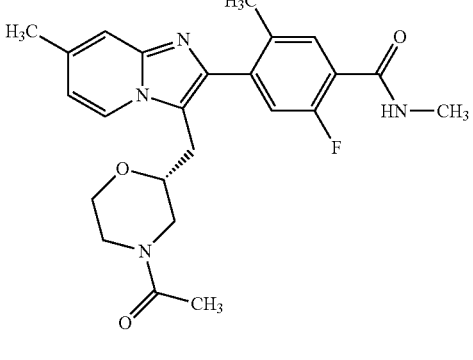 | 2 | HRMS m/z calcd for $C_{24}H_{28}FN_4O_3$ 439.214 [M + H]+, found 439.2142. | $^1$H NMR (400 MHz, CD$_3$OD) δ ppm 2.05 (2 s, 3 H), 2.25 (s, 3 H), 2.41 (dd, J = 12.89, 10.94 Hz, 1 H), 2.46 (s, 3 H), 2.70 (d, J = 3.52 Hz, 1 H), 3.03-3.10 (m, 3 H), 3.12-3.24 (m, 2 H), 3.34-3.45 (m, 1 H), 3.48-3.61 (m, 2 H), 3.62-3.86 (m, 1 H), 4.13-4.32 (m, 1 H), 6.87 (dt, J = 7.13, 1.90 Hz, 1 H), 7.16-7.29 (m, 1H), 7.29-7.36 (m, 1 H), 7.70 (dd, J = 7.62, 3.71 Hz, 1 H), 8.37 (dd, J = 15.23, 7.03 Hz, 1 H). |
| 20 | 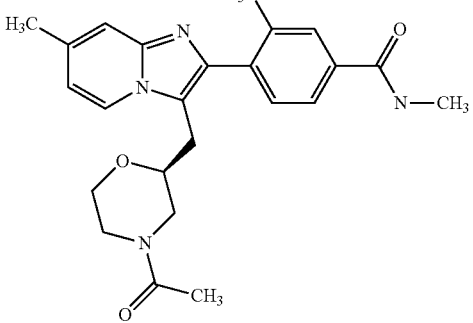 | 3 | HRMS m/z calcd for $C_{24}H_{29}N_4O_3$ 421.2234 [M + H]+, found 421.224. | $^1$H NMR (400 MHz, METHANOL-$d_4$) δ ppm 2.02 (2 s, 3 H), 2.30 (s, 3 H), 2.38 (dd, J = 13.09, 10.74 Hz, 1 H), 2.45 (s, 3 H), 2.60-2.74 (m, 1 H), 2.84-2.95 (m, 3 H), 3.03-3.10 (m, 2 H), 3.10-3.22 (m, 1 H), 3.59-3.70 (m, 2 H), 3.81 (dd, J = 11.91, 3.32 Hz, 1 H), 4.21 (d, J = 13.28 Hz, 1 H), 6.86 (d, J = 7.03 Hz, 1 H), 7.31 (s, 1 H), 7.40-7.51 (m, 1 H), 7.66-7.76 (m, 1 H), 7.79 (br. s, 1 H), 8.37 (dd, J = 12.11, 7.03 Hz, 1 H). |

SFC, chiral stationary phase: The product was analyzed by chiral SFC (UV detection) using isocratic method (mobile phase: 30% EtOH with 0.1% DMEA, supercritical CO$_2$) on Lux Amylose-2, 4.6 × 250 mm, 5 μm particle size, giving an enantiomeric purity of 100%, R$_t$ 8.24 min.

TABLE 1-continued

EXAMPLES 18-46

| Ex | Compound Structure | Cyclization Procedure | LCMC (RT, m/z)[1] | $^1$H NMR |
|---|---|---|---|---|
| 21 | *(structure)* The product was analyzed by chiral SFC (UV detection) using isocratic method (mobile phase: 35% iPrOH with 0.1% DMEA, supercritical $CO_2$) on Lux Amylose-2, 4.6 × 250 mm, 5 μm particle size, giving an enantiomeric purity of 100%, $R_t$ 10.24 min. | 3 | HRMS m/z calcd for $C_{24}H_{29}N_4O_4$ 437.2183 [M + H]$^+$, found 437.2177. | $^1$H NMR (400 MHz, DMSO-$d_6$) δ ppm 2.26 (s, 3 H), 2.37 (s, 3 H), 2.41-2.48 (m, 1 H), 2.80 (d, J = 4.30 Hz, 4 H), 3.02 (d, J = 6.64 Hz, 2 H), 3.25 (td, J = 11.72, 2.73 Hz, 1 H), 3.32 (s, 3 H), 3.44-3.53 (m, 1 H), 3.58-3.76 (m, 3 H), 6.80 (dd, J = 7.23, 1.76 Hz, 1 H), 7.33 (s, 1 H), 7.40 (d, J = 8.20 Hz, 1 H), 7.69 (dd, J = 7.81, 1.56 Hz, 1 H), 7.77 (s, 1 H), 8.39 (d, J = 7.03 Hz, 1 H), 8.46 (d, J = 4.69 Hz, 1 H). |
| 22 | *(structure)* The product was analyzed by chiral SFC (UV detection) using isocratic method (mobile phase: 35% iPrOH with 0.1% DMEA, supercritical $CO_2$) on Lux Amylose-2, 4.6 × 250 mm, 5 μm particle size, giving an enantiomeric purity of 95.244%, $R_t$ 13.96 min. | 3 | HRMS m/z calcd for $C_{24}H_{29}N_4O_4$ 437.2183 [M + H]$^+$, found 437.2177. | $^1$H NMR (400 MHz, DMSO-$d_6$) δ ppm 2.26 (s, 3 H), 2.37 (s, 3 H), 2.80 (d, J = 4.30 Hz, 4 H), 3.02 (d, J = 6.64 Hz, 2 H), 3.17-3.30 (m, 1 H), 3.42-3.58 (m, 5 H), 3.59-3.75 (m, 3 H), 6.80 (dd, J = 7.23, 1.76 Hz, 1 H), 7.33 (s, 1 H), 7.40 (d, J = 7.81 Hz, 1 H), 7.69 (dd, J = 7.81, 1.56 Hz, 1 H), 7.77 (s, 1 H), 8.39 (d, J = 7.03 Hz, 1 H), 8.46 (d, J = 4.30 Hz, 1 H) |
| 23 | *(structure)* | 3 | HRMS m/z calcd for $C_{23}H_{25}F_2N_4O_3$ 443.1889 [M + H]$^+$, found 443.1897. | $^1$H NMR (400 MHz, $CD_3OD$) δ ppm 2.06 (d, J = 1.56 Hz, 3 H), 2.39-2.77 (m, 4 H), 2.90-3.05 (m, 3 H), 3.10-3.25 (m, 3 H), 3.36-3.46 (m, 1 H), 3.54-3.89 (m, 3 H), 4.20-4.37 (m, 1 H), 6.86 (d, J = 7.03 Hz, 1 H), 7.34 (br. s., 1 H), 7.49-7.59 (m, 1 H), 7.59-7.67 (m, 1 H), 8.42 (dd, J = 14.06, 7.03 Hz, 1 H) |
| 24 | *(structure)* | 3 | HRMS m/z calcd for $C_{24}H_{28}FN_4O_4$ 455.2089 [M + H]$^+$, found 455.2092. | $^1$H NMR (400 MHz, $CD_3OD$) δ ppm 2.21 (s, 3 H), 2.42 (s, 3 H), 2.75-2.96 (m, 5 H), 3.02 (d, J = 6.25 Hz, 2 H), 3.34 (br. s., 1 H), 3.52 (br. s., 1 H), 3.62 (s, 3 H), 3.76 (d, J = 11.72 Hz, 3 H), 6.83 (d, J = 6.64 Hz, 1 H), 7.21 (d, J = 10.94 Hz, 1 H), 7.28 (s, 1 H), 7.66 (d, J = 7.03 Hz, 1 H), 8.31 (d, J = 7.03 Hz, 1 H) |

TABLE 1-continued

EXAMPLES 18-46

| Ex | Compound Structure | Cyclization Procedure | LCMC (RT, m/z)[1] | $^1$H NMR |
|---|---|---|---|---|
| 25 | 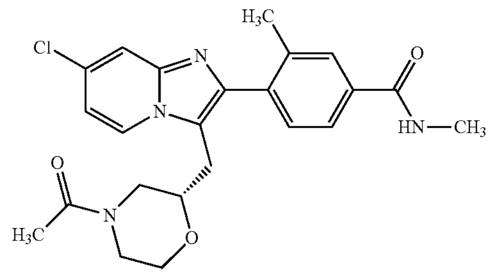 [SMILES: CNC(=O)c1ccc(-c2nc3cc(Cl)ccn3c2C[C@H]2CN(C(C)=O)CCO2)c(C)c1] | 3 | HRMS m/z calcd for $C_{23}H_{26}ClN_4O_3$ 441.1688 [M + H]$^+$, found 441.168. | $^1$H NMR (400 MHz, CD$_3$OD) δ ppm 1.99 (d, J = 13.67 Hz, 3 H), 2.26 (s, 3 H), 2.33-2.72 (m, 1 H), 2.81-2.98 (m, 4 H), 2.99-3.20 (m, 2 H), 3.31-3.42 (m, 1 H), 3.42-3.71 (m, 2 H), 3.71-3.86 (m, 1 H), 4.19 (d, J = 12.89 Hz, 1 H), 7.02 (d, J = 7.03 Hz, 1 H), 7.36-7.51 (m, 1 H), 7.58 (br. s., 1 H), 7.69 (d, J = 6.25 Hz, 1 H), 7.78 (br. s., 1 H), 8.44-8.59 (m, 1 H) |
| 26 | 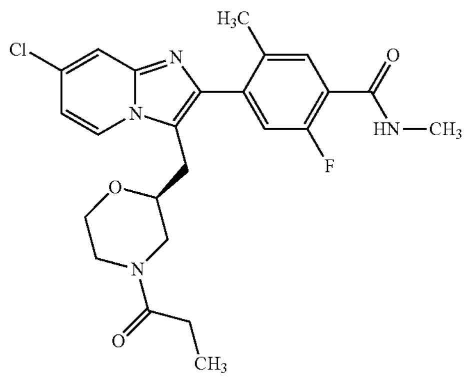 [SMILES: CCC(=O)N1CCO[C@@H](Cc2c(-c3cc(F)c(C(=O)NC)cc3C)nc3cc(Cl)ccn23)C1] | 3 | HRMS m/z calcd for $C_{24}H_{27}ClFN_4O_3$ 473.175 [M + H]$^+$, found 473.1753. | $^1$H NMR (400 MHz, CD$_3$OD) δ ppm 0.99-1.13 (m, 3 H), 2.24 (s, 3 H), 2.26-2.44 (m, 2 H), 2.94-2.98 (m, 4 H), 3.06-3.14 (m, 2 H), 3.35-3.42 (m, 1 H), 3.50-3.76 (m, 3 H), 3.75-3.86 (m, 1 H), 4.16-4.34 (m, 1 H), 6.98-7.10 (m, 1 H), 7.22-7.35 (m, 1 H), 7.59 (d, J = 1.95 Hz, 1 H), 7.70 (dd, J = 7.42, 3.52 Hz, 1 H), 8.45-8.57 (m, 1 H). |
| 27 | 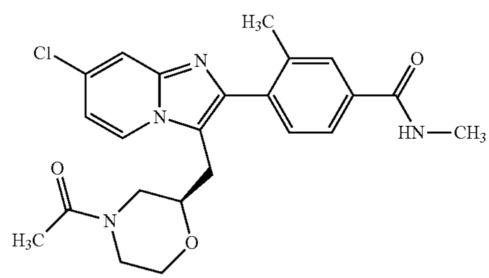 [SMILES: CNC(=O)c1ccc(-c2nc3cc(Cl)ccn3c2C[C@@H]2CN(C(C)=O)CCO2)c(C)c1] | 3 | HRMS m/z calcd for $C_{23}H_{26}ClN_4O_3$ 441.1688 [M + H]$^+$, found 441.1692. | $^1$H NMR (400 NHz, CD$_3$OD) δ ppm 1.99 (d, J = 14.45 Hz, 3 H), 2.26 (s, 3 H), 2.31-2.72 (m, 1 H), 2.82-2.95 (m, 3H), 3.00-3.20 (m, 3 H), 3.35 (td, J = 11.72, 2.34 Hz, 1 H), 3.44-3.69 (m, 2 H), 3.78 (dd, J = 11.52, 2.54 Hz, 1 H), 4.19 (d, J = 12.89 Hz, 1 H), 6.98 (d, J = 7.42 Hz, 1 H), 7.42 (dd, J = 11.72, 7.81 Hz, 1 H), 7.55 (s, 1 H), 7.65-7.73 (m, 1 H), 7.77 (br. s., 1 H), 8.43-8.52 (m, 1 H). |
| 28 | 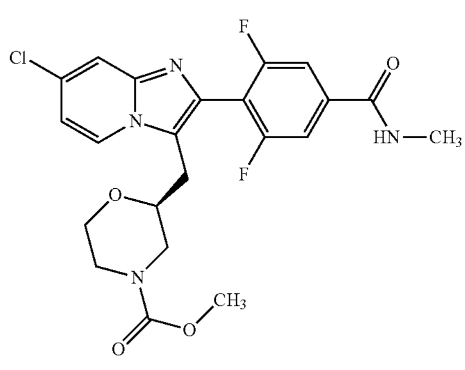 [SMILES: CNC(=O)c1cc(F)c(-c2nc3cc(Cl)ccn3c2C[C@H]2CN(C(=O)OC)CCO2)c(F)c1] | 3 | HRMS m/z calcd for $C_{22}H_{22}ClF_2N_4O_4$ 479.1292 [M + H]$^+$, found 479.1290. | $^1$H NMR (400 MHz, DMSO-d$_6$) δ ppm 2.79-2.84 (m, 3 H), 2.99-3.11 (m, 2 H), 3.14-3.24 (m, 2 H), 3.30-3.70 (m, 5 H), 3.71-3.85 (m, 2 H), 7.08 (dd, J = 7.42, 1.95 Hz, 1 H), 7.65 (d, J = 8.20 Hz, 2 H), 7.75-7.79 (m, 1 H), 8.58 (d, J = 7.42 Hz, 1 H), 8.72 (d, J = 4.30 Hz, 1 H). |

TABLE 1-continued

EXAMPLES 18-46

| Ex | Compound Structure | Cyclization Procedure | LCMC (RT, m/z)[1] | $^1$H NMR |
|---|---|---|---|---|
| 29 | 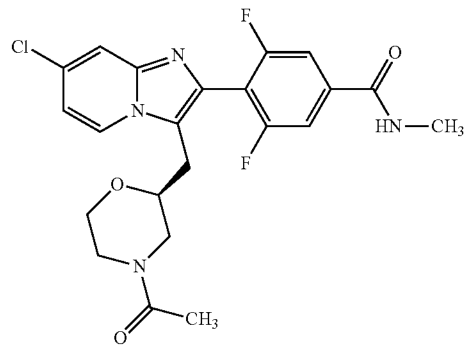 [SMILES: CNC(=O)c1cc(F)c(-c2nc3cc(Cl)ccn3c2C[C@H]2CN(C(C)=O)CCO2)c(F)c1] | 3 | HRMS m/z calcd for $C_{22}H_{22}ClF_2N_4O_3$ 463.1343 [M + H]$^+$, found 463.1348. | $^1$H NMR (400 MHz, DMSO-d$_6$) δ ppm 1.87 (d, J = 2.73 Hz, 3 H), 2.15-2.30 (m, 1 H), 2.77 (d, J = 4.69 Hz, 3 H), 2.96-3.08 (m, 2 H), 3.15-4.15 (m, 6H), 7.00-7.07 (m, 1 H), 7.61 (dd, J = 8.20, 2.73 Hz, 2 H), 7.70-7.74 (m, 1 H), 8.54 (t, J = 6.84 Hz, 1 H), 8.68 (d, J = 4.69 Hz, 1 H). |
| 30 | 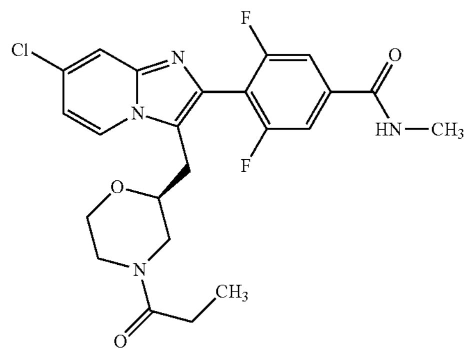 | 3 | HRMS m/z calcd for $C_{22}H_{24}ClF_2N_4O_3$ 477.1500 [M + H]$^+$, found 477.1503. | $^1$H NMR (400 MHz, DMSO-d$_6$) δ ppm 0.87 (t, J = 7.42 Hz, 3 H) 2.00-2.29 (m, 3 H) 2.74-2.80 (m, 3 H) 2.99-3.30 (m, 3 H) 3.50-3.80 (m, 4H), 4.05-4.21 (m, 1 H) 7.00-7.07 (m, 1 H) 7.61 (d, J = 7.81 Hz, 2 H) 7.72 (d, J = 1.56 Hz, 1 H) 8.54 (t, J = 6.84 Hz, 1 H) 8.68 (d, J = 4.30 Hz, 1 H). |
| 31 | 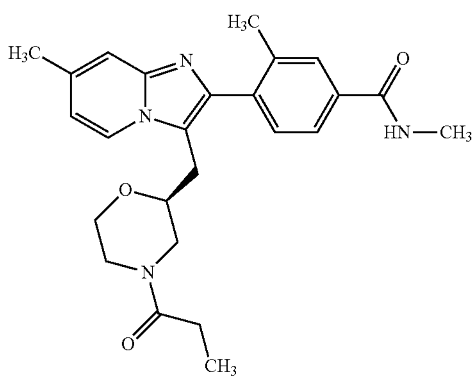 | 3 | HRMS m/z calcd for $C_{25}H_{31}N_4O_3$ 435.2391 [M + H]$^+$, found 435.2395. | $^1$H NMR (400 MHz, CD$_3$OD) δ ppm 1.04 (dt, J = 12.11, 7.62 Hz, 3 H), 2.18-2.42 (m, 5 H), 2.45 (s, 3 H), 2.65-2.70 (m, 1 H), 2.86 (dd, J = 13.09, 10.35 Hz, 1 H), 2.96 (s, 3 H), 3.02-3.20 (m, 2 H), 3.34-3.42 (m, 1 H), 3.46-3.62 (m, 1 H), 3.67 (t, J = 13.87 Hz, 1 H), 3.81 (dd, J = 11.91, 2.15 Hz, 1 H), 4.21 (d, J = 12.89 Hz, 1 H), 6.86 (d, J = 7.03 Hz, 1 H), 7.31 (s, 1 H), 7.39-7.51 (m, 1 H), 7.65-7.76 (m, 1 H), 7.79 (br. s., 1 H), 8.27-8.43 (m, 1 H). |
| 32 | 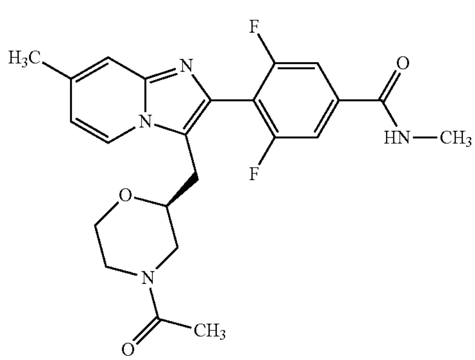 | 3 | HRMS m/z calcd for $C_{23}H_{25}F_2N_4O_3$ 443.1886 [M + H]$^+$, found 443.1889. | $^1$H NMR (400 MHz, DMSO-d$_6$) δ ppm 1.91 (d, J = 6.25 Hz, 3 H), 2.37 (s, 3 H), 2.81 (d, J = 4.7 Hz, 3 H), 2.95-3.07 (m, 2 H), 3.10-3.45 (m, 3 H),, 3.50-4.50 (m, 4 H), 6.80-6.89 (m, 1 H), 7.35 (s, 1 H), 7.63 (dd, J = 8.20, 3.12 Hz, 2 H), 8.37-8.46 (m, 1 H), 8.71 (d, J = 4.30 Hz, 1 H). |

TABLE 1-continued

EXAMPLES 18-46

| Ex | Compound Structure | Cyclization Procedure | LCMC (RT, m/z)[1] | $^1$H NMR |
|---|---|---|---|---|
| 33 | 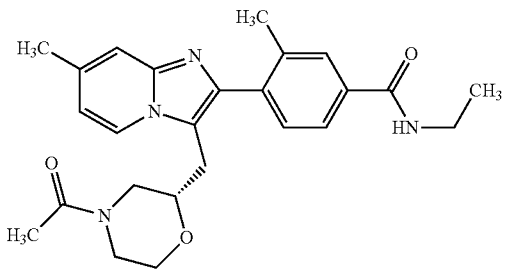 [SMILES: CCNC(=O)c1ccc(-c2nc3cc(C)ccn3c2C[C@H]2CN(C(C)=O)CCO2)c(C)c1] | 3 | HRMS m/z calcd for $C_{25}H_{31}N_4O_3$ 435.2391 $[M + H]^+$, found 435.2398. | $^1$H NMR (400 MHz, CD$_3$OD) δ ppm 1.22 (t, J = 7.23 Hz, 3 H), 1.98 (d, J = 16.80 Hz, 3 H), 2.26 (s, 3 H), 2.42 (s, 3 H), 2.59-2.91 (m, 1 H), 2.86-3.18 (m, 3 H), 3.31-3.53 (m, 4 H), 3.54-3.68 (m, 1 H), 3.78 (d, J = 11.72 Hz, 1 H), 4.17 (d, J = 12.89 Hz, 1 H), 6.82 (d, J = 7.03 Hz, 1 H), 7.28 (s, 1 H), 7.36-7.47 (m, 1 H), 7.63-7.72 (m, 1 H), 7.76 (br. s., 1 H), 8.33 (dd, J = 11.91, 7.23 Hz, 1 H) |
| 34 | 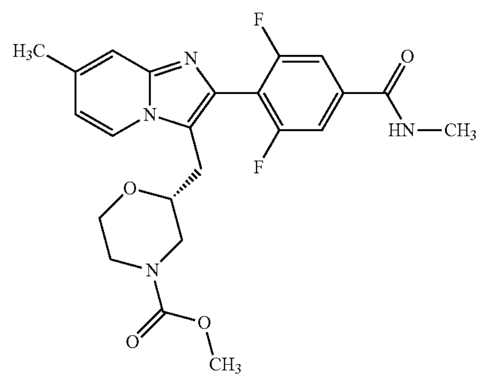 | 4 | HRMS m/z calcd for $C_{23}H_{25}F_2N_4O_4$ 459.1836 $[M + H]^+$, found 459.1838. | $^1$H NMR (400 MHz, CD$_3$OD) δ ppm 2.45 (s, 3 H), 2.53-2.69 (m, 1 H), 2.78-2.99 (m, 4 H), 3.01-3.18 (m, 2 H), 3.33-3.39 (m, 1 H), 3.50-3.62 (m, 1 H), 3.65 (s, 3 H), 3.72-3.87 (m, 3 H), 6.86 (dd, J = 7.03, 1.56 Hz, 1 H), 7.33 (s, 1 H), 7.59 (d, J = 8.20 Hz, 2 H), 8.40 (d, J = 7.03 Hz, 1 H). |
| 35 | 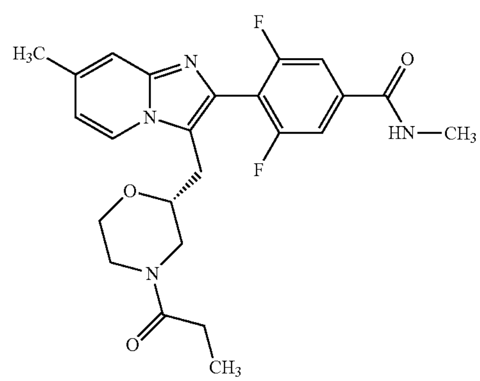 | 4 | HRMS m/z calcd for $C_{24}H_{27}F_2N_4O_3$ 457.2046 $[M + H]^+$, found 457.2043. | $^1$H NMR (400 MHz, DMSO-d$_6$) δ ppm 0.60 (t, J = 7.43 Hz, 3 H), 1.76-2.04 (m, 2 H), 2.06 (s, 3 H), 2.15-2.29 (m, 4 H), 2.35-2.47 (m, 0.5 H), 2.59-2.78 (m, 2 H), 2.99 (s, 3 H), 3.04-3.08 (s, 1 H), 3.25-3.46 (m, 0.5 H), 3.65-3.86 (m, 1 H), 6.52 (d, J = 6.64 Hz, 1 H), 7.03 (s, 1 H), 7.33 (d, J = 7.81 Hz, 2 H), 8.05-8.18 (m, 1 H), 8.36 (d, J = 4.69 Hz, 1 H) |

The product was analyzed by chiral SFC (UV detection) using isocratic method (mobile phase: 40% EtOH with 0.1% DMEA, supercritical CO$_2$) on ChiralPak IC-H, 10 × 250 mm, 5 μm particle size, giving an enantiomeric purity of 90.034%, R$_t$ 8.02 min.

| 36 | | 4 | MS (ESI) m/z 448.11 $[M + H]^+$, MS (ESI) m/z 470.09 $[M + Na]^+$. | $^1$H NMR (300 MHz, CDCl$_3$) δ ppm 2.29 (s, 3 H), 2.50-2.62 (m, 1 H), 2.80-2.97 (m, 1 H), 3.00 (d, J = 5.95 Hz, 2 H), 3.05 (d, J = 4.87 Hz, 3 H), 3.30-3.41 (m, 1 H), 3.46-3.56 (m, 1 H), 3.68 (s, 3 H), 3.70-3.95 (m, 3 H), 6.16-6.23 (m, 1 H), 6.98 (dd, J = 7.17, 1.64 Hz, 1 H), 7.33 (d, J = 7.83 Hz, 1 H), 7.64 (d, J = 8.08 Hz, 1 H), 7.74 (s, 1 H), 8.00-8.01 (m, 1 H), 8.38 (d, J = 7.21 Hz, 1 H) |

TABLE 1-continued

EXAMPLES 18-46

| Ex | Compound Structure | Cyclization Procedure | LCMC (RT, m/z)[1] | $^1$H NMR |
|---|---|---|---|---|
| 37 | 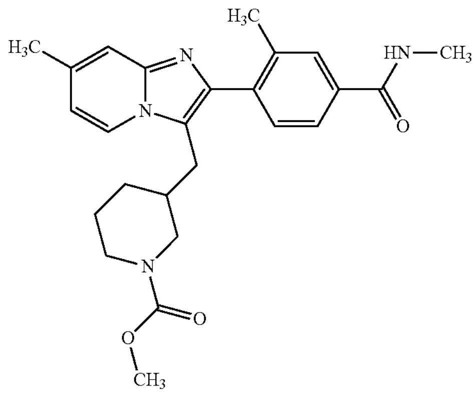 | 5 | MS (ESI) m/z 435.16 [M + H]+. | $^1$H NMR (300 MHz, CDCl$_3$) δ ppm 0.80-0.92 (m, 1 H), 1.18-1.32 (m, 2 H), 1.45-1.60 (m, 1 H), 1.65-1.80 (m, 1 H), 2.24-2.30 (m, 1 H), 2.32 (s, 3 H), 2.42 (s, 3 H), 2.57-2.81 (m, 3 H), 3.03 (d, J = 4.87 Hz, 3 H), 3.61 (s, 3 H), 3.80-4.05 (m, 2 H), 6.23-6.30 (m, 1 H), 6.70 (dd, J = 6.98, 1.35 Hz, 1 H), 7.34 (d, J = 7.90 Hz, 1 H), 7.37 (s, 1 H), 7.59 (dd, J = 7.90, 1.44 Hz, 1 H), 7.69 (d, J = 1.11 Hz, 1 H), 7.83 (d, J = 6.98 Hz, 1 H) |
| 38 | 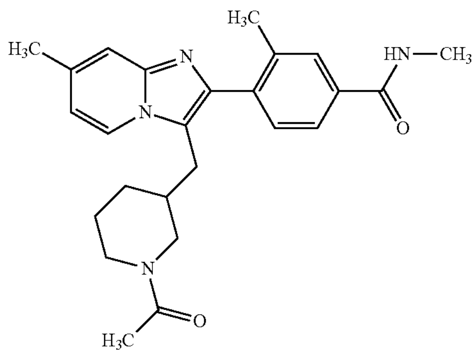 | 5 | MS (ESI) m/z calcd for C$_{25}$H$_{31}$N$_4$O$_2$ 419.24 [M + H]+, found 419.18. | $^1$H NMR (300 MHz, CDCl$_3$) δ ppm 0.78-0.90 (m, 1 H), 1.18-1.30 (m, 2 H), 1.47-1.54 (m, 1 H), 1.65-1.78 (m, 1 H), 1.83 and 2.02 (2 s, 3 H), 2.17-2.25 (m, 0.75 H), 2.33 (s, 3 H), 2.41-2.44 (m, 3 H), 2.62-2.91 (m, 2.25 H), 3.02-3.06 (m, 3 H), 3.35-3.50 (m, 1 H), 3.50-3.65 (m, 1 H), 4.28-4.45 (m, 1 H), 6.15-6.22 (m, 1 H), 6.67-6.75 (m, 1 H), 7.34-7.39 (m, 2 H), 7.57-7.61 (m, 1 H), 7.68-7.22 (m, 1 H), 7.81-7.85 (m, 1 H) |
| 39 | 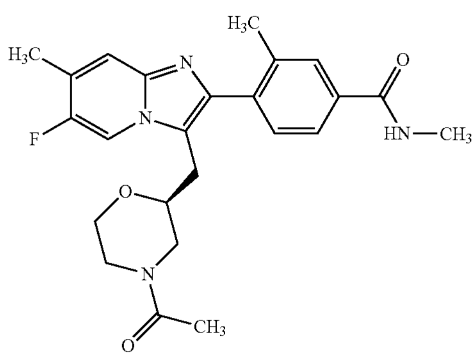 | 5 | MS (ESI) m/z 439.09 [M + H]+. | $^1$H NMR (300 MHz, CDCl$_3$) δ ppm 1.93 and 2.04 (2 s, 3 H), 2.27 (s, 3 H), 2.29-2.35 (m, 0.5 H), 2.39 (s, 3 H), 2.58-2.69 (m, 0.5 H), 2.77 (dd, J = 12.94, 10.69 Hz, 0.5 H), 2.93 (t, J = 5.62 Hz, 2 H), 3.01 (d, J = 4.73 Hz, 3 H), 3.12-3.22 (m, 0.5 H), 3.30-3.55 (m, 3 H), 3.82-3.90 (m, 1 H), 4.31 (t, J = 12.13 Hz, 1 H), 6.41-6.53 (m, 1 H), 7.30 (d, J = 7.87 Hz, 1 H), 7.36 (d, J = 7.05 Hz, 1 H), 7.59 (t, J = 8.26 Hz, 1 H), 7.70 (s, 1 H), 8.15 (dd, J = 17.69, 5.14 Hz, 1 H) |
| 40 | 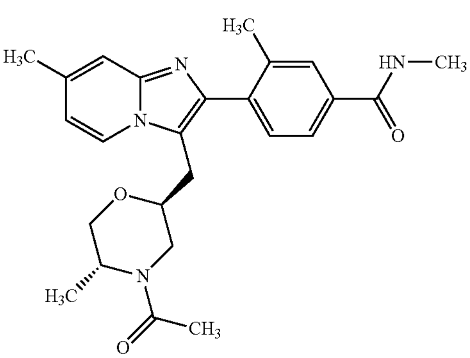 | 5 | MS (ESI) m/z 435.12 [M + H]+, MS (ESI) m/z 457.10 [M + Na]+. | $^1$H NMR (300 MHz, CDCl$_3$) δ ppm 1.09-1.26 (m, 3 H), 1.75-2.04 (m, 3 H), 2.32 (s, 3 H), 2.42 (s, 3 H), 2.98-3.09 (m, 1 H), 3.03 (d, J = 4.76 Hz, 3 H), 3.16-3.28 (m, 3 H), 3.40-3.77 (m, 3 H), 3.98 (br s, 1 H), 6.28 (d, J = 4.00 Hz, 1 H), 6.72 (d, J = 6.73 Hz, 1 H), 7.35-7.39 (m, 2 H), 7.58 (d, J = 7.86 Hz, 1 H), 7.71 (s, 1 H), 7.96 (d, J = 6.99 Hz, 1 H) |

TABLE 1-continued

EXAMPLES 18-46

| Ex | Compound Structure | Cyclization Procedure | LCMC (RT, m/z)[1] | $^1$H NMR |
|---|---|---|---|---|
| 41 | 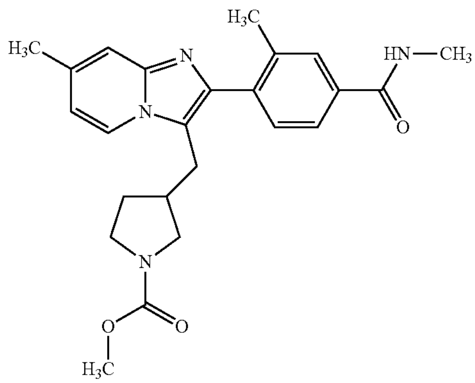 | 5 | MS (ESI) m/z 421.13 [M + H]+ | $^1$H NMR (300 MHz, CDCl$_3$) δ ppm 1.32-1.42 (m, 1 H), 1.72-1.84 (m, 1 H), 2.31 (s, 3 H), 2.39-2.44 (m, 1 H), 2.43 (s, 3 H), 2.77-2.85 (m, 1 H), 2.89 (d, J = 7.55 Hz, 2 H), 3.03 (d, J = 4.88 Hz, 3 H), 3.12-3.48 (m, 3 H), 3.61 (d, J = 3.54 Hz, 3 H), 6.31 (br s, 1 H), 6.71 (dd, J = 7.00, 1.63 Hz, 1 H), 7.31-7.38 (m, 2 H), 7.58 (d, J = 7.79 Hz, 1 H), 7,70 (s, 1 H), 7.85 (d, J = 6.95 Hz, 1 H) |
| 42 | 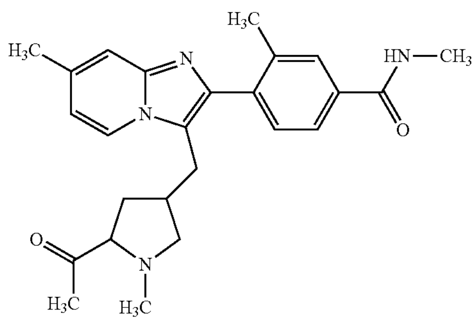 | 5 | MS (ESI) m/z 419.09 [M + H]+; MS (ESI) m/z 441.06 [M + Na]+. | $^1$H NMR (300 MHz, CDCl$_3$) δ ppm 1.02-1.19 (m, 3 H), 1.45-1.59 (m, 1 H), 1.58-1.77 (m, 1 H), 1.80, 1.86, 1.96 and 1.97 (4 s, 3 H), 2.02-2.16 (m, 0.5 H), 2.33 (s, 3 H), 2.44 (s, 3 H), 2.53-2.67 (m, 0.5 H), 2.72-2.88 (m, 0.5 H), 2.90-2.97 (m, 2 H), 2.98-3.06 (m, 3 H), 3.27-3.35 (m, 0.5 H), 3.50 (dd, J = 12.11, 7.70 Hz, 0.5 H), 3.72-3.80 (m, 0.5 H), 3.85-4.00 (m, 0.5 H), 4.05-4.13 (m, 0.5 H), 6.22-6.30 (m, 1 H), 6.69-6.76 (m, 1 H), 7.35 (d, J = 7.92 Hz, 1 H), 7.40 (s, 1 H), 7.57-7.64 (m, 1 H), 7.70-7.73 (m, 1 H), 7.81-7.89 (m, 1 H) |
| 43 | 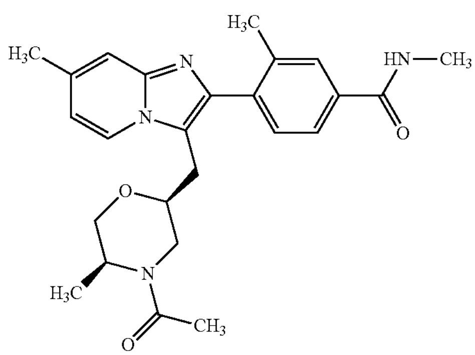 | 5 | MS (ESI) m/z 435.11 [M + H]+, f; MS (ESI) m/z 457.09 [M + Na]+ | $^1$H NMR (300 MHz, CDCl$_3$) δ ppm 1.10 and 1.25 (2 d, J = 6.89 and 6.81 Hz, 3 H), 1.88 and 2.04 (2 s, 3 H), 2.30 (s, 3 H), 2.41 and 2.42 (2 s, 3 H), 2.47-2.52 (m, 0.5 H), 2.84-3.16 (m, 5 H), 3.38-3.50 (m, 2 H), 3.61-2.74 (m, 1.5 H), 4.16 (dd, J = 13.63, 2.70 Hz, 0.5 H), 4.44-4.51 (m, 0.5 H), 6.33-6.44 (m, 1 H), 6.65-6.71 (m, 1 H), 7.32-7.36 (m, 1 H), 7.56-7.62 (m, 1 H), 7.68-7.71 (m, 1 H), 8.07 and 8.15 (2 d, J = 7.06 and 7.24 Hz, 1 H) |
| 44 | 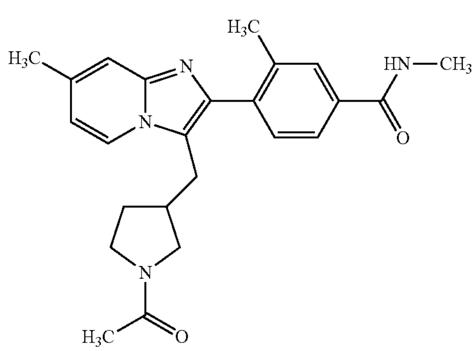 | 5 | MS (ESI) m/z 405.16 [M + H]+. | $^1$H NMR (300 MHz, CDCl$_3$) δ ppm 1.35-1.49 (m, 1 H), 1.76-1.92 (m, 1 H), 1.84 and 1.92 (2 s, 3 H), 2.32 (d, J = 2.07 Hz, 3 H), 2.36-2.55 (m, 1 H), 2.43 (s, 3 H), 2.79-2.98 (m, 3 H), 3.03 (d, J = 4.88 Hz, 3 H), 3.20-3.33 (m, 2 H), 3.41-3.57 (m, 1 H), 6.33 (br s, 1 H), 6.71-6.75 (m, 1 H), 7.35 (d, J = 7.85 Hz, 1 H), 7.37-7.41 (m, 1 H), 7.59 (dt, J = 7.96, 1.84 Hz, 1 H), 7.69-7.73 (m, 1 H), 7.86 (dd, J = 6.96, 3.14 Hz, 1 H) |

[1]These compounds were analyzed by analytical HPLC (UV, ELSD and MS) using a low pH method (mobile phase: A: H$_2$O with 0.05% TFA; B: CH$_3$CN with 0.05% TFA; Zorbax SB C18, Agilent reverse phase column; column size: 4.6 × 30 mm; particle size: 1.8 μm; 4.5 min. run with a gradient of 5-95% B in A).

Example 45

Preparation of methyl 4-((7-methyl-2-(2-methyl-4-(methylcarbamoyl)phenyl)imidazo[1,2-a]pyridin-3-yl)methyl)piperidine-1-carboxylate

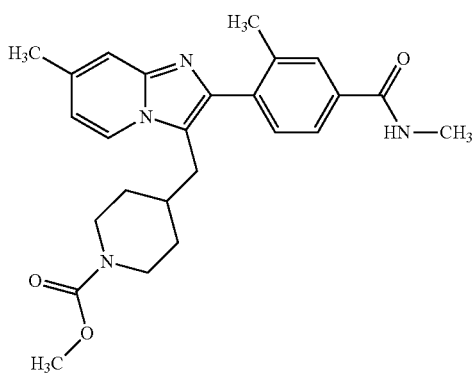

Part A. Preparation of methyl 4-(1-ethoxyvinyl)-3-methylbenzoate

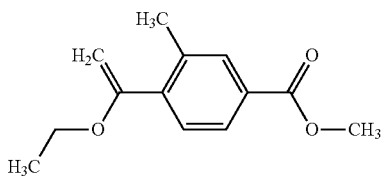 [SMILES: C=C(OCC)c1ccc(C(=O)OC)cc1C]

A mixture of methyl 4-bromo-3-methylbenzoate (5 g, 21.83 mmol), PdCl$_2$(dbpf) (0.356 g, 0.55 mmol) and tributyl (1-ethoxyvinyl)stannane (8.11 mL, 24.01 mmol) in 1,4-dioxane (20 mL) was heated at 150° C. during 15 min in a microwave reactor. The mixture was filtered on a pad of diatomaceous earth, which was subsequently washed with EtOAc (100 mL). Brine (60 mL) was added to the resulting mixture, and the phases were separated. The aqueous phase was extracted with EtOAc (3×60 mL). The combined organic extracts were dried over magnesium sulfate, filtered, and concentrated under reduced pressure. The residue was used without further purification in the next step. LCMS m/z 221.09 [M+H]$^+$ (ESI).

Part B. Preparation of methyl 4-(2-bromoacetyl)-3-methylbenzoate

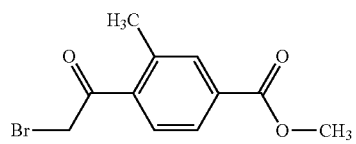

Methyl 4-(1-ethoxyvinyl)-3-methylbenzoate (4.81 g, 21.83 mmol) was dissolved in THF (30 mL) and water (15.00 mL) at 22° C. and 1-bromopyrrolidine-2,5-dione (3.89 g, 21.83 mmol) was added. The resulting mixture was stirred at 22° C. for 15 min. EtOAc (70 mL) and water (50 mL) were added to the resulting mixture, and the phases were separated. The aqueous phase was extracted with EtOAc (3×50 mL). The combined organic extracts were dried over magnesium sulfate, filtered, and concentrated under reduced pressure. The residue was purified by flash chromatography on silica gel, eluting with mixtures of EtOAc and heptane to afford methyl 4-(2-bromoacetyl)-3-methylbenzoate (4.51 g, 76%) as a solid. $^1$H NMR (400 MHz, CDCl$_3$) δ ppm 2.55 (s, 3H), 3.95 (s, 3H), 4.41 (s, 2H), 7.68 (d, 1H), 7.89-8.00 (m, 2H)

Part C. Preparation of methyl 3-methyl-4-(7-methylimidazo[1,2-a]pyridin-2-yl)benzoate

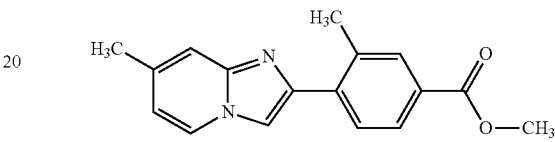

A mixture of 4-methylpyridin-2-amine (1.149 g, 10.63 mmol), methyl 4-(2-bromoacetyl)-3-methylbenzoate (2.4 g, 8.85 mmol) and sodium bicarbonate (1.487 g, 17.71 mmol) in ethanol (8 mL) was heated in a microwave reaction to 120° C. during 10 min. After cooling to rt, the precipitate was collected by filtration, washed with water and dried under reduced pressure to afford methyl 3-methyl-4-(7-methylimidazo[1,2-a]pyridin-2-yl)benzoate (1.49 g, 60%) as a solid. $^1$H NMR (400 MHz, CD$_3$OD) δ ppm 2.43 (s, 3H), 2.56 (s, 3H), 3.92 (s, 3H), 6.81 (d, J=6.64 Hz, 1H), 7.34 (s, 1H), 7.83-7.87 (m, 1H), 7.87-7.92 (m, 1H), 7.95 (s, 1H), 7.99 (s, 1H), 8.33 (d, J=7.03 Hz, 1H)
LCMS m/z 281.02 [M+H]$^+$ (ESI).

Part D. Preparation of N,3-dimethyl-4-(7-methylimidazo[1,2-a]pyridin-2-yl)benzamide

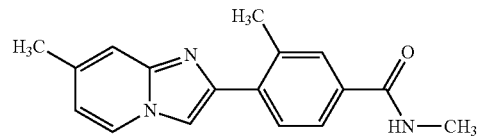

A mixture of methyl 3-methyl-4-(7-methylimidazo[1,2-a]pyridin-2-yl)benzoate (1.47 g, 5.24 mmol), 40% water solution of methanamine (10 ml, 116.17 mmol) was heated in a microwave reactor to 105° C. during 10 min. EtOAc (50 mL) was added to the resulting mixture, the mixture was were filtered, and the two phases separated. The aqueous phase was extracted with EtOAc (3×50 mL). The combined organic phases were dried over magnesium sulfate, filtered, and concentrated under reduced pressure. The residue was purified by flash chromatography on silica gel, eluting with mixtures of EtOAc and methanol, to afford N,3-dimethyl-4-(7-methylimidazo[1,2-a]pyridin-2-yl)benzamide (1.1 g, 75%) as a solid. 1H NMR (400 MHz, CD$_3$OD) δ ppm 2.43 (s, 3H), 2.56 (s, 3H), 2.94 (s, 3H), 6.80 (dd, J=7.03, 1.56 Hz, 1H), 7.34 (s, 1H), 7.67-7.74 (m, 1H), 7.76 (s, 1H), 7.82 (d, J=7.81 Hz, 1H), 7.97 (s, 1H), 8.33 (d, J=7.03 Hz, 1H) LCMS m/z 280.10 [M+H]$^+$ (ESI).

Part E. Preparation of 4-(3-bromo-7-methylimidazo[1,2-a]pyridin-2-yl)-N,3-dimethylbenzamide

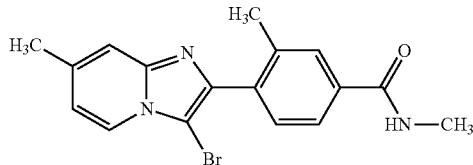

A solution of dibromine (0.051 mL, 0.99 mmol) in ethanol (1 mL) was added dropwise to a stirred solution of N,3-dimethyl-4-(7-methylimidazo[1,2-a]pyridin-2-yl)benzamide (184 mg, 0.66 mmol) in ethanol (1.000 mL) at room temperature. The resulting mixture was stirred 90 min, concentrated under reduced pressure and the residue was suspended in water. The aqueous mixture was made basic using NaHCO$_3$ and extracted with CH$_2$Cl$_2$. The organic phase was dried over MgSO$_4$, concentrated under reduced pressure and the residue was purified by silica gel flash chromatography (gradient 7-60% EtOAc in heptane) to give 4-(3-bromo-7-methylimidazo[1,2-a]pyridin-2-yl)-N,3-dimethylbenzamide (210 mg, 89%) as a solid. LCMS m/z 357.98, 359.97 [M+H]$^+$ (ESI).

Part F. Preparation of tert-butyl 4-((7-methyl-2-(2-methyl-4-(methylcarbamoyl)phenyl)imidazo[1,2-a]pyridin-3-yl)methylene)piperidine-1-carboxylate

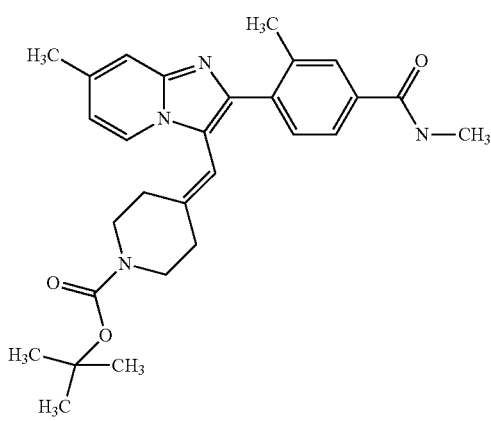 [SMILES: CNC(=O)c1ccc(-c2nc3cc(C)ccn3c2C=C2CCN(C(=O)OC(C)(C)C)CC2)c(C)c1]

To a mixture of PdCl$_2$(dbpf) (60.0 mg, 0.09 mmol) and tetrabutylammonium chloride (25.6 mg, 0.09 mmol) under N$_2$, 4-(3-bromo-7-methylimidazo[1,2-a]pyridin-2-yl)-N,3-dimethylbenzamide (330 mg, 0.92 mmol) and tert-butyl 4-methylenepiperidine-1-carboxylate (545 mg, 2.76 mmol) in DMA (10 mL) were added, and the resulting mixture was heated in a microwave reactor at 120° C. for 45 min. The resulting mixture was filtered over diatomaceous earth. The filtrate was concentrated under reduced pressure, then EtOAc (20 mL) and water (20 mL) were added. The phases were separated and the aqueous phase was extracted with EtOAc (3×20 mL). The combined organic phases were dried over magnesium sulfate, filtered, and concentrated under reduced pressure. The residue was used in the next step without further purification. LCMS m/z 475.30 [M+H]$^+$ (ESI).

Part G. Preparation of tert-butyl 4-((7-methyl-2-(2-methyl-4-(methylcarbamoyl)phenyl)imidazo[1,2-a]pyridin-3-yl)methyl)piperidine-1-carboxylate

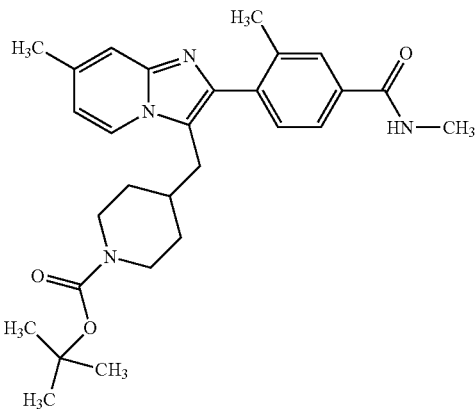 [SMILES: CNC(=O)c1ccc(-c2nc3cc(C)ccn3c2CC2CCN(C(=O)OC(C)(C)C)CC2)c(C)c1]

The pressure of the H-cube was set to 60 bar and the temperature to 60° C. with a 30 mm cartridge containing 10% Pd/C. A solution of tert-butyl 4-((7-methyl-2-(2-methyl-4-(methylcarbamoyl)phenyl)imidazo[1,2-a]pyridin-3-yl)methylene)piperidine-1-carboxylate in ethanol (5 mL) and ethyl acetate (5 mL) was pumped through the H-Cube at a rate of mL/min. After completion, the fractions were concentrated and the residue was used in the next step without further purification. MS m/z 477.30 [M+H]$^+$ (ESI).

Part H. Preparation of methyl 4-((7-methyl-2-(2-methyl-4-(methylcarbamoyl)phenyl)imidazo[1,2-a]pyridin-3-yl)methyl)piperidine-1-carboxylate

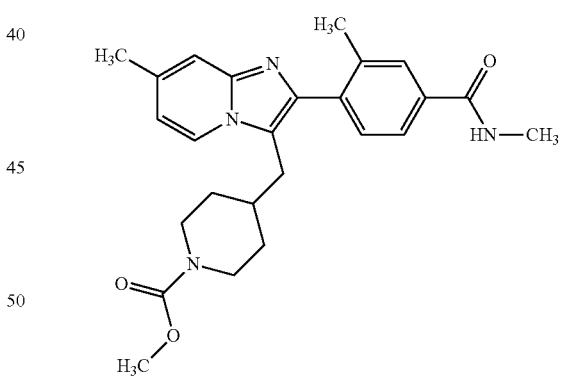

A mixture of tert-butyl 4-((7-methyl-2-(2-methyl-4-(methylcarbamoyl)phenyl)imidazo[1,2-a]pyridin-3-yl)methyl)piperidine-1-carboxylate compound containing N,3-dimethyl-4-(7-methylimidazo[1,2-a]pyridin-2-yl)benzamide (180 mg, 1:1 mixture) and HCl (0.022 mL, 0.71 mmol) in MeOH (2 mL) was heated at 70° C. for 1 hr. The resulting mixture was cooled to rt, concentrated under reduced pressure, and the residue was dissolved in dichloromethane (2.000 mL). Methyl chloroformate (0.028 mL, 0.36 mmol) and DIPEA (0.250 mL, 1.43 mmol) were added to the solution, and the resulting mixture was stirred at 0° C. for 1 hr. After concentration under reduced pressure, the residue was purified on preparative HPLC MS (Mobile phase: 30-50% B; A: H₂O with 10 mM NH₄CO₃ and 0.375% NH₄OH v/v, B: CH₃CN, 25 min run) on XBridge Prep C18 OBD, 30×150 mm, 5 nm, Waters reverse phase column, to afford methyl 4-((7-methyl-2-(2-methyl-4-(methylcarbamoyl)phenyl)imidazo[1,2-a]pyridin-3-yl)methyl)piperidine-1-carboxylate (11.00 mg, 10.63%) as a solid. ¹H NMR (400 MHz, METHANOL-d₄) δ ppm 0.81-1.03 (m, 2H), 1.49 (d, J=12.50 Hz, 2H), 1.71-1.89 (m, 1H), 2.30 (s, 3H), 2.45 (s, 3H), 2.66 (br. s., 2H), 2.84 (d, J=7.42 Hz, 2H), 2.94 (s, 3H), 3.61 (s, 3H), 3.92 (d, J=5.08 Hz, 2H), 6.88 (dd, J=7.23, 1.76 Hz, 1H), 7.32 (s, 1H), 7.40 (d, J=7.81 Hz, 1H), 7.70 (dd, J=7.81, 1.95 Hz, 1H), 7.79 (s, 1H), 8.25 (d, J=7.03 Hz, 1H). HRMS m/z calcd for $C_{25}H_{31}N_4O_3$ 435.2391 [M+H]⁺. found 435.2405.

Example 46

Preparation of 4-(3-((1-acetylpiperidin-4-yl)methyl)-7-methylimidazo[1,2-a]pyridin-2-yl)-N,3-dimethylbenzamide

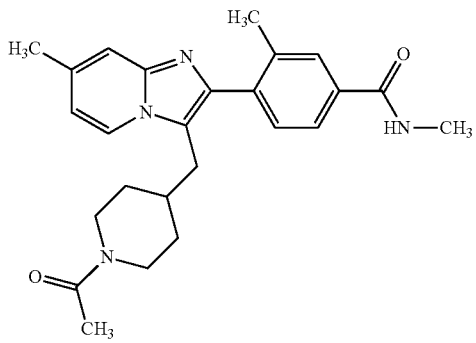

A mixture of tert-butyl 4-((7-methyl-2-(2-methyl-4-(methylcarbamoyl)phenyl)imidazo[1,2-a]pyridin-3-yl)methyl)piperidine-1-carboxylate compound containing N,3-dimethyl-4-(7-methylimidazo[1,2-a]pyridin-2-yl)benzamide (200 mg, 1:1 mixture) and hydrogen chloride (32.9 mg, 0.90 mmol) in MeOH (3.0 mL) was heated at 70° C. for 1 hr. After concentration, the residue was dissolved in CH₂Cl₂ (3.00 mL), followed by addition of pyridine (143 mg, 1.80 mmol) and acetic anhydride (30.7 mg, 0.30 mmol). The resulting mixture was stirred at 0° C. for 1 hr. After concentration, the crude was purified by flash chromatography on silica gel, eluting with mixtures of ethyl acetate and methanol, and then purification by preparative HPLC (UV collection) using a low pH method (Mobile phase: A-H2O with 0.05% TFA; B-CH3CN, on Luna C18, 50×250 mm, 15 um Phenomenex reverse phase column), 20 min run with a gradient of 10-20% B in A then purification by HPLC (MS collection) using a high pH method (Mobile phase: A-H2O with 10 mM NH5CO3 and 0.375% NH4OH v/v; B-MeOH, on Gemini-NX C18 110A, Axia, 30×150 mm, 5 um Phenomenex reverse phase column), 19.5 min. run with a gradient of 40-60% B in A then purification with a Mettler-Toledo Minigram Supercritical Fluid Chromatography instrument using the following conditions: Cyano Column, 10.0×250 mm, 6 μm particle size, 10.0 mL/min, mobile phase: 25% EtOH with 0.1% DMEA, supercritical CO₂, regulator set to 100 Bar, column temperature set to 35° C., UV 215 nm, providing 4-(3-((1-acetylpiperidin-4-yl)methyl)-7-methylimidazo[1,2-a]pyridin-2-yl)-N,3-dimethylbenzamide (7.00 mg, 16.68%) as a solid. ¹H NMR (400 MHz, methanol-d₄). δ ppm 0.82-1.09 (m, 2H), 1.35 (d, J=10.55 Hz, 1H), 1.46-1.66 (m, 2H), 1.87 (ddd, J=15.14, 7.52, 4.30 Hz, 1H), 2.00 (s, 3H), 2.30 (s, 3H), 2.40-2.52 (m, 4H), 2.83-3.02 (m, 5H), 3.74 (br. s, 1H), 4.33 (d, J=13.28 Hz, 1H), 6.89 (dd, J=7.03, 1.56 Hz, 1H), 7.33 (s, 1H), 7.41 (d, J=7.81 Hz, 1H), 7.71 (d, J=8.20 Hz, 1H), 7.79 (s, 1H), 8.27 (d, J=7.03 Hz, 1H); HRMS m/z calcd for $C_{25}H_{31}N_4O_2$ 419.2442 [M+H]⁺. found 419.2437.

Example 47

Preparation of (R)-4-(3-((4-acetylmorpholin-2-yl)methyl)-7-methylimidazo[1,2-a]pyridin-2-yl)-N,3-dimethylbenzamide

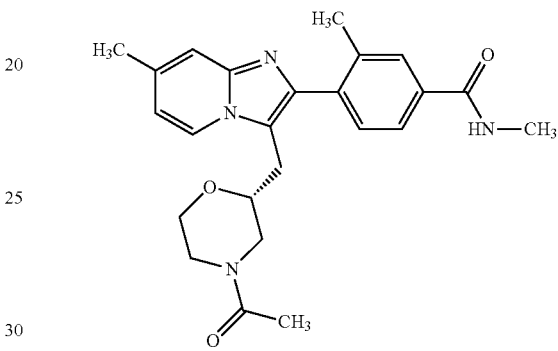

¹H NMR (400 MHz, CD₃OD) δ ppm 2.02 (2 s, 3H), 2.30 (s, 3H), 2.38 (dd, J=13.09, 10.74 Hz, 1H), 2.45 (s, 3H), 2.60-2.74 (m, 1H), 2.84-2.95 (m, 3H), 3.03-3.10 (m, 2H), 3.10-3.22 (m, 1H), 3.59-3.70 (m, 2H), 3.81 (dd, J=11.91, 3.32 Hz, 1H), 4.21 (d, J=13.28 Hz, 1H), 6.86 (d, J=7.03 Hz, 1H), 7.31 (s, 1H), 7.40-7.51 (m, 1H), 7.66-7.76 (m, 1H), 7.79 (br. s., 1H), 8.37 (dd, J=12.11, 7.03 Hz, 1H). HRMS m/z calcd for $C_{24}H_{29}N_4O_2$ 421.2234 [M+H]⁺. found 421.2237, R$_t$ 0.993 min. Applicants synthesized this compound using a relatively complicated process. If applicants were to re-synthesize this compound, they would instead use a process similar to that used to prepare the compound in Example 20.

Example 48

Biological Evaluation of Compounds as Antagonists at Human P2X3 Receptor In Vitro The antagonist properties of compounds in the present invention were assayed as inhibitors of intracellular calcium increase induced by activation of hP2X3 (human Purinergic P2X receptors subtype 3, accession number AB016608 for clone A and accession number NM 002559 for clone B), expressed in RLE cells (rat liver endothelium, ATCC. The RLE/hP2X3 cells were grown in William's medium 1× (Gibco, 12551-032), supplemented with 10% Fetal bovine serum (Wisent, 090850), 2 mM L-Glutamine (Wisent, 609-065-EL), and 600 μg/mL Geneticin G-418 (Wisent, 61234) in a humidified incubator (5% CO₂ and 37° C.).

Fluo-4 assay on FDSS7000 (Hamamatsu) was performed using cryopreserved RLE cells stably expressing hP2X3 plated in 384 well plates, 24 hr before the experiment at a density appropriate for obtaining the desired final confluence. After processing the cell plates with Fluo-4 and performing a subsequent incubation followed by washing steps, a double addition was carried out. The first addition included the test compounds diluted in HBSS buffer containing 2 mM $CaCl_2$ preincubated for 20 min before a second addition. The second addition included 2 uM of ATP. Calcium mobilization was measured with the FDSS7000 over a time lapse of 3 min, and fluorescent counts were exported for analysis. This resulted in a $pIC_{50}$, which was calculated in Activity base with ExcelFit. Hill coefficients and % inhibitions can also be determined.

$IC_{50}$'s obtained using the above methods are shown in Table 2.

TABLE 2

$IC_{50}$'s Observed for the Compounds of Examples 15-47

| Ex | Human P2X3 $IC_{50}$ (µM) |
|---|---|
| 15 | 0.003 |
| 16 | 0.003 |
| 17 | 0.006 |
| 18 | 0.007 |
| 19 | 0.158 |
| 20 | 0.004 |
| 21 | 0.007 |
| 22 | 0.045 |
| 23 | 0.018 |
| 24 | 0.010 |
| 25 | 0.007 |
| 26 | 0.011 |
| 27 | 0.111 |
| 28 | 0.006 |
| 29 | 0.005 |
| 30 | 0.006 |
| 31 | 0.005 |
| 32 | 0.003 |
| 33 | 0.007 |
| 34 | 0.030 |
| 35 | 0.016 |
| 36 | 0.114 |
| 37 | 0.011 |
| 38 | 0.010 |
| 39 | 0.010 |
| 40 | 0.074 |
| 41 | 0.084 |
| 42 | 0.059 |
| 43 | 0.008 |
| 44 | 0.103 |
| 45 | 0.026 |
| 46 | 0.066 |
| 47 | 0.087 |

Example 49

Biological Evaluation of Example 15 in an In Vivo Model of Inflammatory Pain

Figure 2:
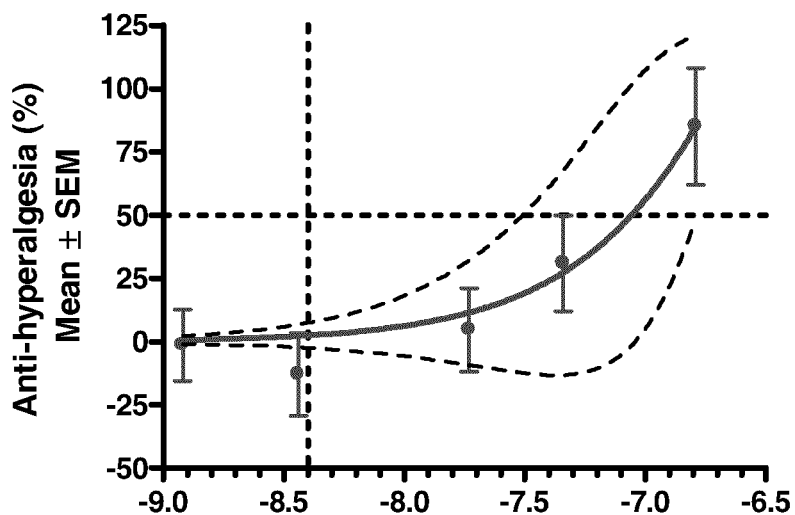
FIG. 2: Efficacy of Example 15 in rat FCA 96-hr model of inflammatory pain 30 minutes after p.o. dosing: mechanical hyperalgesia (MH). Log free $C_P$=Logarithm of molar free drug concentration in plasma.

One of the compounds of the present invention was evaluated in an in vivo model of inflammatory pain. Oral dosing of Example 15 (0.3-1-3-10-20 µmol/kg) produced a free plasma concentration dependent reversal of both heat and mechanical hyperalgesia endpoints in the rat FCA 96 hr paw model of inflammatory pain. The potency (EC50 free plasma concentration) of example 15 was 18 nM and 87 nM respectively in reversing the heat and mechanical hyperalgesia. The results are shown in FIGS. 1 and 2.

Methods for Characterization of Analgesic Effects of Example 15 in the FCA 96 hr Rat Model of Inflammatory Pain:

Male Sprague-Dawley rats (Charles River, St-Constant, Qc, CAN) weighing 200-225 g were utilized for the animal experiment studies. The animals were group-housed in polycarbonate, ventilated cages (filter top) in a controlled environment room (12-h light/dark cycle, 20.5-23.5° C., relative humidity: 40-70%) with food (14% Protein Rodent Maintenance Diet, Harlan Teklad, Madisson, Wis., USA) and water ad libitum.

Inflammation was induced by injection of a single 40 µl Freund's complete adjuvant (FCA) intra-plantar injection into the rat's left hindpaw. All experiments were conducted 96 h after FCA administration. Twenty-four hours prior to behavioral testing animals were brought to the laboratory for acclimatization to the new environment. Animals were sacrificed immediately after data acquisition.

Heat hyperalgesia (Plantar Test) was assessed using a Paw Thermal Stimulator to apply a controlled heat to the plantar surface of the affected paw. Rats were placed in individual plexiglass boxes with holes, on the glass surface of the device which was maintained at 30° C. They were allowed to habituate to their boxes for 15-30 minutes. A movable arm containing the heat source, with an angled mirror, was used to place the heat source directly under the injured paw without disturbing the animal. The heat source and timer were then turned on simultaneously; when the animal withdrew the hind paw the number of seconds was recorded. Each animal was tested twice, 5 minutes apart, to avoid sensitization, and the average value was taken. To avoid any tissue damage, a cut-off time of 20 s was used.

Mechanical hyperalgesia was assessed using the Ugo Basile analgesy meter (Ugo Basile, Comerio, Italy). Animals were gently restrained, and a steadily increasing pressure was applied to the dorsal surface of a hind paw via a probe with a dome-shaped tip (diameter of 1 mm). The pressure required to elicit paw withdrawal was determined. An assay cut off was set at 295 g. Two trials were conducted with 5 min intervals between each trial. Paw withdrawal thresholds were calculated as the mean of the two values. Animals were randomised and allocated to treatment groups to achieve a minimum statistical power of 80%. In all cases the experimenter was blind to the treatment received.

Satellite animals were used to monitor the free plasma concentration of example 15 at the doses and time points used in the nociceptive tests. Free plasma EC50 values in behavioral studies were determined from 4-point concentration-response curves using non-linear regression and a sigmoidal variable slope logistic model (Prism 4.03, GraphPad Software Inc., USA).

Unless otherwise indicated, the following definitions are to be used when reading this patent:

The chemical nomenclature used in this patent generally follows the examples and rules stated in *Nomenclature of Organic Chemistry, Sections A, B, C, D, E, F, and H*, Pergamon Press, Oxford, 1979.

The modifier "$C_m$-$C_n$" means that the modified group contains from m to n carbon atoms. For example, the term "$C_1$-$C_6$-alkyl" means an alkyl group containing from 1 to 6 carbon atoms.

The term "alkyl" means a straight or branched chain alkane (hydrocarbon) radical. Examples of alkyl groups include, for example, methyl, ethyl, propyl, butyl pentyl, and hexyl.

The term "cycloalkyl" refers to a fully saturated cyclic hydrocarbon group. Examples of cycloalkyls include, for example, cyclopropyl, cyclobutyl, cyclopentyl, and cyclohexyl.

The term "halogen" means chlorine, bromine, fluorine, or iodine.

The term "alkoxy" means —O-alkyl. Examples of alkoxys include, for example, methoxy, ethoxy, propoxy, and butoxy.

The term "optionally substituted" means that the modified group, structure, or molecule may be either: (1) substituted with a substituent at one or more substitutable positions, or (2) not substituted.

The term "pharmaceutically acceptable" is used to characterize a moiety (e.g., a salt, dosage form, carrier, diluent, or excipient) as being appropriate for use in accordance with sound medical judgment. In general, a pharmaceutically acceptable moiety has one or more benefits that outweigh any deleterious effect that the moiety may have. Deleterious effects may include, for example, excessive toxicity, irritation, allergic response, and other problems and complications.

"Ac" means acetyl.
"AcOH" means acetic acid.
"AIBN" means azobisisobutylonitrile.
"atm" means atmosphere.
"boc" means tert-butyl carbonyl.
"Bu" means butyl.
"d" means doublet.
"DCM" means dichloromethane.
"dd" means doublet of doublet.
"ddd" means doublet of doublet of doublet.
"DIPEA" means diisopropylethylamine.
"DMA" means dimethylacetamide.
"DMEA" means dimethylethylamine.
"DMF" means N,N-dimethyl formamide.
"DMSO-$d_6$" means dimethylsulfoxide-$d_6$.
"DMT-MM" means 4-(4,6-Dimethoxy-1,3,5-triazin-2-yl)-4-methylmorpholinium chloride.
"ESI" means electrospray ionization.
"Et" means ethyl.
"Et$_2$O" means diethyl ether.
"Et$_3$N" means triethylamine.
"EtOAc" means ethyl acetate.
"EtOH" means ethanol.
"Ex" means example.
"g" means gram.
"hr" means hour or hours.
"$^1$H NMR" means proton nuclear magnetic resonance.
"HATU" means O-(7-azabenzotriazol-1-yl)-N,N,N',N'-tetramethyluronium hexafluorophosphate.
"HOBT" means 1-hydroxybenzotriazole.
"HPLC" means high-performance liquid chromatography.
"HRMS" means high-resolution mass spectrometry.
"L" means liter.
"LCMS" means liquid chromatography/mass spectroscopy.
"m" means multiplet.
"M" means molar.
"mL" means milliliter.
"Me" means methyl.
"MeCN" means acetonitrile.
"MeOH" means methanol.
"mg" means milligram.
"MHz" means megahertz.
"min" means minute or minutes.
"mmol" means millimole.
"mol" means mole.
"MS" means mass spectrometry.
"MTBE" means methyl tert-butyl ether.
"N" means normal.
"NBS" means N-bromosuccinimide.
"Pd(OH)$_2$" means Palladium hydroxide.
"Ph" means phenyl.
"ppm" means parts per million.
"Pr" means propyl.
"q" means quartet.
"qt" means quintet.
"$R_t$" means retention time (HPLC).
"s" means singlet.
"SFC" means supercritical-fluid chromatography.
"t" means triplet.
"TFA" means trifluoroacetic acid.
"THF" means tetrahydrofuran.
"TLC" means thin layer chromatography.
"TMEDA" means N,N,N',N'-tetramethyl-1,2-ethylenediamine.
"UV" means ultraviolet.
"v/v" means volume per unit volume.
"vol" means volume.

References made in the singular may also include the plural. For example, "a" and "an" may refer to either one or more than one.

The words "comprise," "comprises," and "comprising" in this patent (including the claims) are to be interpreted inclusively rather than exclusively. This interpretation is intended to be the same as the interpretation that these words are given under United States patent law.

The above description of illustrative embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:
1. A compound of Formula I or a salt thereof, wherein:
Formula I is:

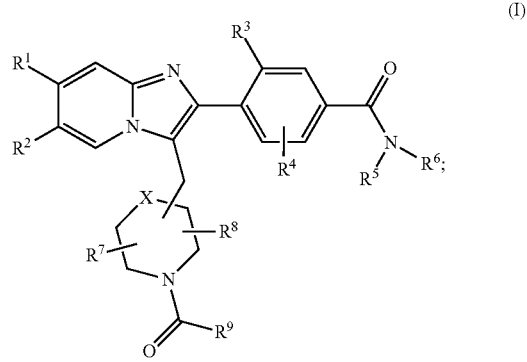

$R^1$ is selected from the group consisting of cyano, halogen, methyl, and ethyl;
$R^2$ is selected from the group consisting of hydrogen, halogen, methyl, and ethyl;
$R^3$ is selected from the group consisting of halogen, methyl, and ethyl;
$R^4$ is selected from the group consisting of hydrogen, halogen, methyl, ethyl, and methoxy;
as to $R^5$ and $R^6$:
  $R^5$ and $R^6$ are independently selected from the group consisting of hydrogen, $C_1$-$C_6$-alkyl, and hydroxy-$C_1$-$C_6$-alkyl; or R⁵ and R⁶, together with the nitrogen to which they are both attached, form a 5- or 6-member heterocycloalkyl, wherein:
the heterocycloalkyl is optionally substituted with one or more substituents independently selected from the group consisting of halogen, hydroxyl, and C₁-C₄-alkyl;
R⁷ and R⁸ are independently selected from the group consisting of hydrogen and C₁-C₄-alkyl;
R⁹ is selected from the group consisting of C₁-C₆-alkyl, C₃-C₆-cycloalkyl, C₁-C₆-alkyl-C₃-C₆-cycloalkyl, halo-C₁-C₆-alkyl, C₁-C₆-alkoxy, halo-C₁-C₆-alkoxy, and C₁-C₆-alkoxy-C₁-C₆-alkyl; and
X is selected from a bond, CH₂, and O.

2. The compound of claim 1, wherein R¹ is methyl and R² is hydrogen.

3. The compound of claim 1, wherein R³ and R⁴ are fluoro.

4. The compound of claim 1, wherein X is O.

5. The compound of claim 1, wherein the compound corresponds in structure to:

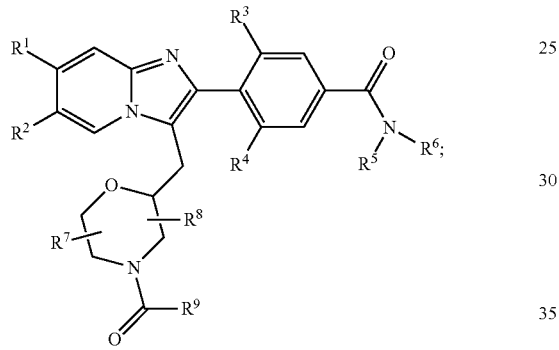

and
R⁴ is selected from the group consisting of halogen, methyl, and ethyl.

6. The compound of claim 1, wherein R⁵ is hydrogen and R⁶ is C₁-C₆-alkyl.

7. The compound of claim 6, wherein R⁶ is methyl.

8. The compound of claim 1, wherein R⁷ and R⁸ are hydrogen.

9. The compound of claim 1, wherein R⁹ is C₁-C₆-alkoxy.

10. The compound of claim 9, wherein R⁹ is methoxy.

11. The compound of claim 1, wherein the compound corresponds in structure to:

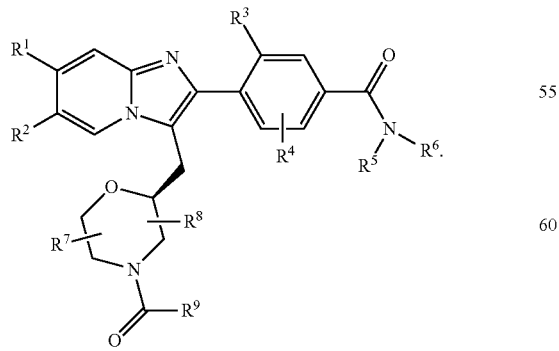

12. The compound of claim 1, wherein the compound corresponds in structure to:

(16-1)

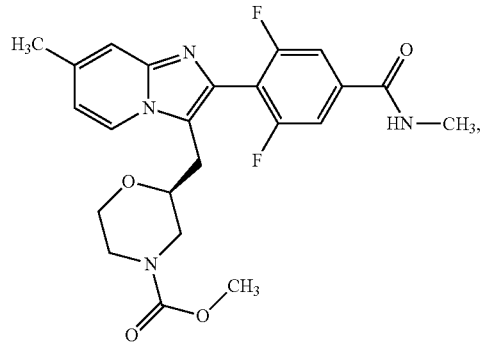

(16-2)

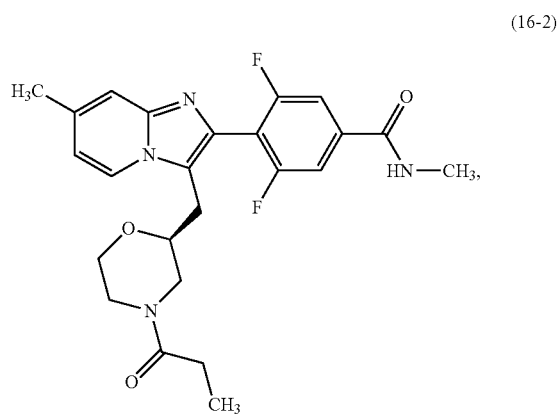

(16-3)

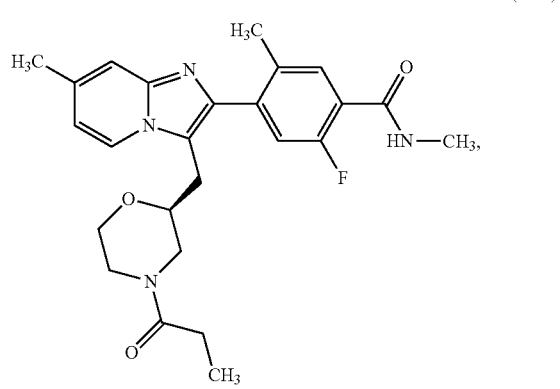

(16-4)

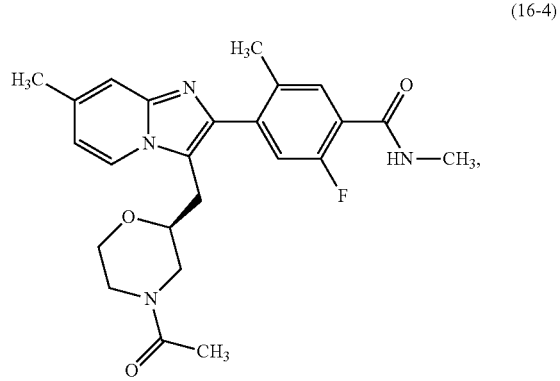 [SMILES: CNC(=O)c1cc(F)c(-c2nc3cc(C)ccn3c2C[C@H]2CN(C(=O)OC)CCO2)c(F)c1]

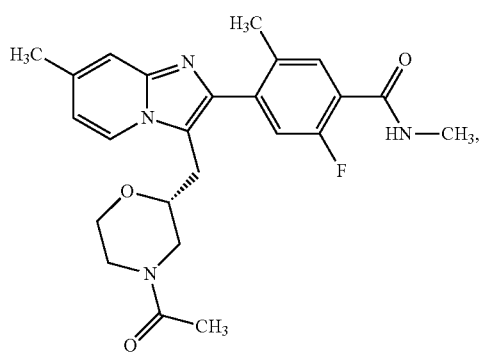
(16-5)
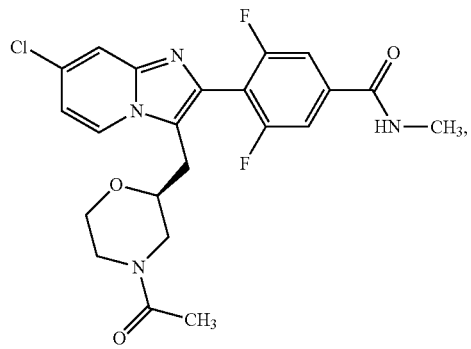
(16-15)
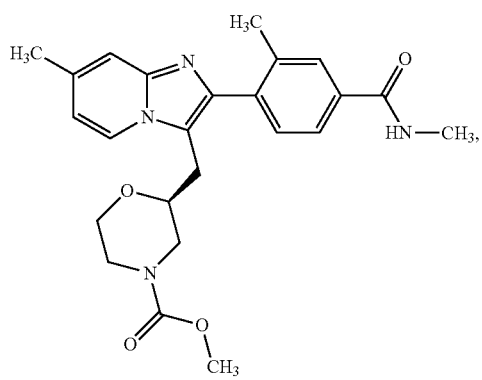
(16-6)
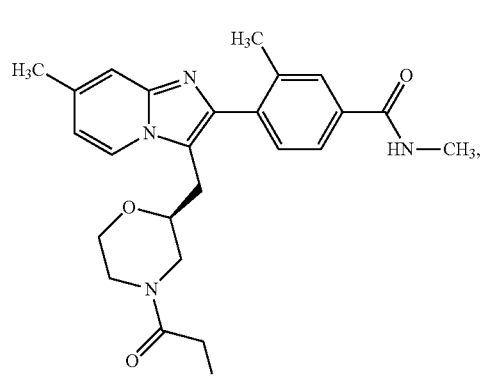
(16-16)
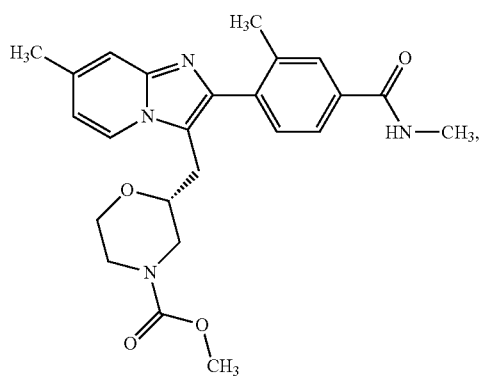
(16-7)
(16-17)
(16-8)
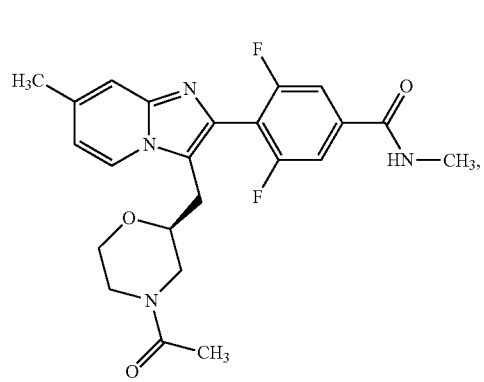
(16-18)

(16-19)
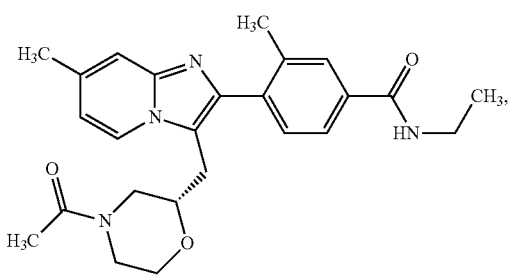
(16-20)
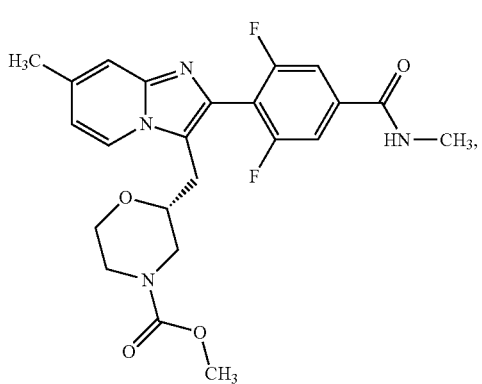
(16-9)
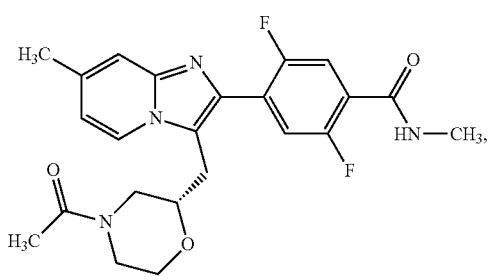
(16-10)
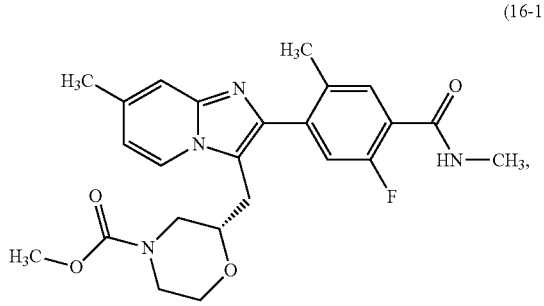
(16-11)
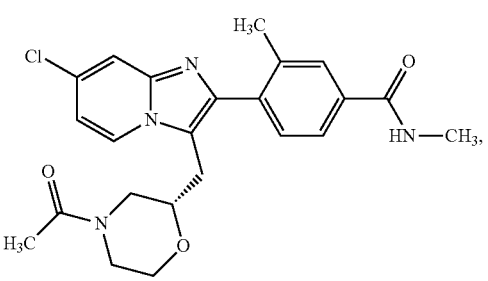
(16-12)
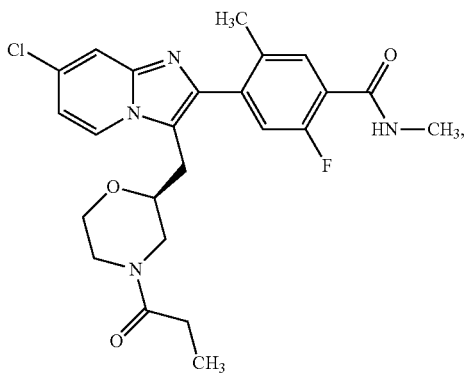
(16-13)
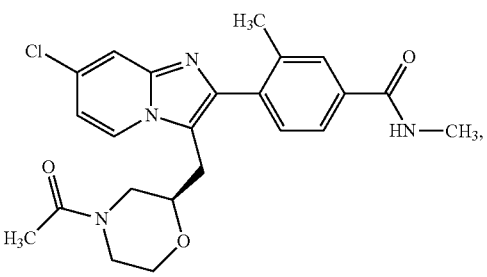
(16-14)
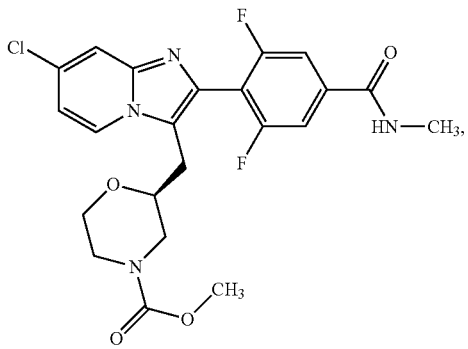
(16-21)
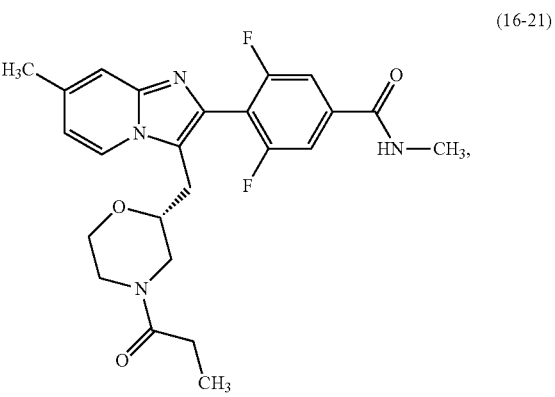 [SMILES: CCC(=O)N1CCO[C@H](Cc2c(-c3c(F)cc(C(=O)NC)cc3F)nc3cc(C)ccn23)C1]

(16-22)
(16-23)
(16-24)
(16-25)
(16-26)
(16-27)
(16-28)
(16-29)

(16-30) [structure]

(16-31) [structure]

(16-32) [structure] and (16-33) [structure]

13. A pharmaceutical composition, wherein the composition comprises:
the compound of claim 1; and
a carrier, diluent, or excipient.

14. The compound of claim 1, wherein the compound corresponds in structure to:

(16-1) [structure]

15. The compound of claim 1, wherein the compound corresponds in structure to:

(16-20) [structure]

16. The compound of claim 1, wherein the compound corresponds in structure to:

(16-2) [structure]

17. The compound of claim 1, wherein the compound corresponds in structure to:

(16-21)
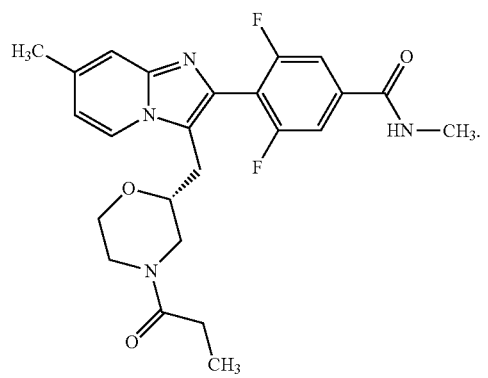
* * * * *